US012697210B2

(12) United States Patent
Titone

(10) Patent No.: US 12,697,210 B2
(45) Date of Patent: Aug. 4, 2026

(54) TRANSCATHETER TISSUE CUTTING SYSTEM

(71) Applicant: Edwards Lifesciences Corporation, Irvine, CA (US)

(72) Inventor: Ryan S. Titone, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 856 days.

(21) Appl. No.: 17/909,608

(22) PCT Filed: Feb. 17, 2021

(86) PCT No.: PCT/US2021/018383
§ 371 (c)(1),
(2) Date: Sep. 6, 2022

(87) PCT Pub. No.: WO2021/178135
PCT Pub. Date: Sep. 10, 2021

(65) Prior Publication Data
US 2023/0105063 A1 Apr. 6, 2023

Related U.S. Application Data

(60) Provisional application No. 62/984,554, filed on Mar. 3, 2020.

(51) Int. Cl.
*A61F 2/24* (2006.01)
*A61B 18/14* (2006.01)
*A61B 18/00* (2006.01)

(52) U.S. Cl.
CPC .......... *A61F 2/2427* (2013.01); *A61B 18/149* (2013.01); *A61B 18/1492* (2013.01);
(Continued)

(58) Field of Classification Search
None
See application file for complete search history.

(56) References Cited

U.S. PATENT DOCUMENTS 3,574,865 A 4/1971 Hamaker et al.
4,493,321 A 1/1985 Leather
(Continued)

FOREIGN PATENT DOCUMENTS

CN 102834072 A 12/2012
CN 109700508 A 5/2019
(Continued)

OTHER PUBLICATIONS

International Search Report and Written Opinion received for PCT Patent Application No. PCT/US21/20438, mailed on Jun. 7, 2021, 14 pages.
(Continued)

*Primary Examiner* — Linda C Dvorak
*Assistant Examiner* — Nicholas S Borsch
(74) *Attorney, Agent, or Firm* — Klarquist Sparkman LLP

(57) ABSTRACT

Systems and methods for cutting tissue using a transcatheter approach are disclosed. In some examples, the systems and methods are implemented as part of a delivery system that includes an implant with a support structure and a cutting element coupled to the support structure, such that the cutting element configured to cut tissue.

21 Claims, 28 Drawing Sheets

(52) U.S. Cl.
CPC .. *A61F 2/2418* (2013.01); *A61B 2018/00101*
(2013.01); *A61B 2018/00369* (2013.01); *A61B*
*2018/00601* (2013.01); *A61B 2018/1407*
(2013.01); *A61B 2018/1475* (2013.01)

(56) References Cited

U.S. PATENT DOCUMENTS

| | | | |
|---|---|---|---|
| 4,765,332 A | 8/1988 | Fischell et al. | |
| 5,026,383 A | 6/1991 | Nobles | |
| 5,069,679 A | 12/1991 | Taheri | |
| 5,078,716 A * | 1/1992 | Doll | A61B 18/14 |
| | | | 606/47 |
| 5,108,370 A | 4/1992 | Walinsky | |
| 5,232,446 A | 8/1993 | Arney | |
| 5,304,134 A | 4/1994 | Kraus et al. | |
| 5,470,313 A | 11/1995 | Crocker et al. | |
| 5,514,151 A | 5/1996 | Fogarty et al. | |
| 5,593,405 A * | 1/1997 | Osypka | A61L 29/02 |
| | | | 606/7 |
| 5,620,415 A | 4/1997 | Lucey et al. | |
| 5,658,302 A | 8/1997 | Wicherski et al. | |
| 5,853,408 A | 12/1998 | Muni | |
| 5,951,576 A | 9/1999 | Wakabayashi | |
| 5,964,778 A | 10/1999 | Fugoso et al. | |
| 5,989,287 A | 11/1999 | Yang et al. | |
| 6,027,510 A | 2/2000 | Alt | |
| 6,063,082 A | 5/2000 | DeVore et al. | |
| 6,106,530 A | 8/2000 | Harada | |
| 6,245,040 B1 | 6/2001 | Inderbitzen et al. | |
| 6,264,683 B1 | 7/2001 | Stack et al. | |
| 6,270,465 B1 | 8/2001 | Keith et al. | |
| 6,450,948 B1 | 9/2002 | Matsuura et al. | |
| 6,616,661 B2 | 9/2003 | Wellman et al. | |
| 6,746,463 B1 | 6/2004 | Schwartz | |
| 6,872,215 B2 | 3/2005 | Crocker et al. | |
| 6,939,359 B2 | 9/2005 | Tu et al. | |
| 6,942,681 B2 | 9/2005 | Johnson | |
| 7,331,972 B1 | 2/2008 | Cox | |
| 7,341,555 B2 | 3/2008 | Ootawara et al. | |
| 8,221,349 B2 | 7/2012 | Auyoung et al. | |
| 8,486,097 B2 | 7/2013 | Mark et al. | |
| 8,491,613 B2 | 7/2013 | Bliss et al. | |
| 8,491,614 B2 | 7/2013 | Lemaitre et al. | |
| 8,556,921 B2 | 10/2013 | Bliss et al. | |
| 8,979,925 B2 | 3/2015 | Chang et al. | |
| 9,107,666 B2 | 8/2015 | Manwaring et al. | |
| 9,119,716 B2 | 9/2015 | Lee et al. | |
| 9,402,986 B2 | 8/2016 | Bell et al. | |
| 10,441,416 B2 | 10/2019 | Oba et al. | |
| 11,648,337 B2 | 5/2023 | Wang et al. | |
| 2002/0082614 A1 | 6/2002 | Logan et al. | |
| 2003/0114794 A1 | 6/2003 | Duchamp | |
| 2003/0208195 A1 * | 11/2003 | Thompson | A61B 18/1492 |
| | | | 606/41 |
| 2004/0073165 A1 | 4/2004 | Musbach et al. | |
| 2004/0243211 A1 | 12/2004 | Colliou et al. | |
| 2004/0267280 A1 | 12/2004 | Nishide et al. | |
| 2005/0137690 A1 | 6/2005 | Salahieh et al. | |
| 2005/0137700 A1 | 6/2005 | Spence et al. | |
| 2006/0009832 A1 | 1/2006 | Fisher | |
| 2006/0074485 A1 | 4/2006 | Realyvasquez | |
| 2006/0095025 A1 | 5/2006 | Levine et al. | |
| 2006/0111704 A1 | 5/2006 | Brenneman et al. | |
| 2006/0259137 A1 | 11/2006 | Artof et al. | |
| 2006/0271081 A1 | 11/2006 | Realyvasquez | |
| 2007/0213663 A1 | 9/2007 | Wang | |
| 2008/0045937 A1 | 2/2008 | Whisenant et al. | |
| 2008/0125860 A1 | 5/2008 | Webler et al. | |
| 2009/0012557 A1 | 1/2009 | Osypka | |
| 2009/0030503 A1 * | 1/2009 | Ho | A61B 17/1204 |
| | | | 623/1.24 |
| 2009/0209955 A1 | 8/2009 | Forster et al. | |
| 2010/0105981 A1 | 4/2010 | Ho et al. | |
| 2010/0198040 A1 * | 8/2010 | Friedman | A61B 18/1492 |
| | | | 606/41 |

| | | | |
|---|---|---|---|
| 2010/0204662 A1 | 8/2010 | Orlov et al. | |
| 2011/0004157 A1 | 1/2011 | Dewaele et al. | |
| 2011/0190867 A1 | 8/2011 | Vonderwalde et al. | |
| 2011/0218620 A1 | 9/2011 | Meiri et al. | |
| 2011/0264179 A1 | 10/2011 | Eckerdal | |
| 2011/0283514 A1 | 11/2011 | Fogarty et al. | |
| 2012/0083809 A1 | 4/2012 | Drasler et al. | |
| 2012/0130173 A1 | 5/2012 | Lutze et al. | |
| 2012/0136385 A1 | 5/2012 | Cully | |
| 2012/0209377 A1 | 8/2012 | Machold et al. | |
| 2012/0234893 A1 | 9/2012 | Schuckmann et al. | |
| 2012/0239142 A1 | 9/2012 | Liu et al. | |
| 2012/0265156 A1 | 10/2012 | Devereux et al. | |
| 2012/0289987 A1 | 11/2012 | Wilson et al. | |
| 2013/0096606 A1 | 4/2013 | Bruchman et al. | |
| 2013/0116715 A1 | 5/2013 | Weber | |
| 2013/0289607 A1 | 10/2013 | Pedersen et al. | |
| 2013/0304036 A1 | 11/2013 | Kimmel et al. | |
| 2013/0310833 A1 | 11/2013 | Brown et al. | |
| 2014/0012252 A1 | 1/2014 | Bliss et al. | |
| 2014/0172003 A1 | 6/2014 | Goepfrich | |
| 2014/0276764 A1 * | 9/2014 | Shuman | A61B 18/1477 |
| | | | 606/41 |
| 2014/0296969 A1 | 10/2014 | Tegels et al. | |
| 2014/0330366 A1 | 11/2014 | Dehdashtian et al. | |
| 2014/0343660 A1 | 11/2014 | Shimoyama | |
| 2015/0148896 A1 | 5/2015 | Karapetian et al. | |
| 2015/0151080 A1 | 6/2015 | Verbeek | |
| 2015/0202410 A1 | 7/2015 | Odeh | |
| 2015/0230919 A1 | 8/2015 | Chau et al. | |
| 2015/0257883 A1 | 9/2015 | Basude et al. | |
| 2015/0351903 A1 | 12/2015 | Morriss et al. | |
| 2016/0166243 A1 | 6/2016 | Wilson et al. | |
| 2016/0206424 A1 | 7/2016 | Al-Jilaihawi et al. | |
| 2016/0235525 A1 * | 8/2016 | Rothstein | A61F 2/2418 |
| 2016/0270778 A1 | 9/2016 | Zergiebel | |
| 2016/0346084 A1 | 12/2016 | Taylor et al. | |
| 2017/0056068 A1 | 3/2017 | Hess et al. | |
| 2017/0165060 A1 | 6/2017 | Barongan | |
| 2017/0319333 A1 | 11/2017 | Tegels et al. | |
| 2017/0361073 A1 | 12/2017 | Stapleton | |
| 2018/0000509 A1 | 1/2018 | Wilson et al. | |
| 2018/0008268 A1 | 1/2018 | Khairkhahan | |
| 2018/0092677 A1 | 4/2018 | Peterson et al. | |
| 2018/0185153 A1 | 7/2018 | Bishop et al. | |
| 2018/0214267 A1 | 8/2018 | Lally et al. | |
| 2018/0214270 A1 | 8/2018 | Subramanian et al. | |
| 2019/0110893 A1 | 4/2019 | Haarer et al. | |
| 2019/0255285 A1 | 8/2019 | Freeseman et al. | |
| 2019/0298517 A1 | 10/2019 | Sanchez et al. | |
| 2019/0328420 A1 | 10/2019 | Khairkhahan et al. | |
| 2019/0344054 A1 | 11/2019 | Slattery et al. | |
| 2020/0038030 A1 | 2/2020 | Baril et al. | |
| 2020/0146690 A1 | 5/2020 | Rothstein et al. | |
| 2020/0289102 A1 | 9/2020 | Wilson et al. | |
| 2020/0297490 A1 | 9/2020 | Zhou et al. | |
| 2020/0337726 A1 | 10/2020 | Wilson et al. | |
| 2021/0046291 A1 | 2/2021 | Sardesai et al. | |
| 2021/0085456 A1 | 3/2021 | Skarsgard | |
| 2021/0298899 A1 | 9/2021 | Huddleston | |
| 2021/0346089 A1 | 11/2021 | Childs et al. | |
| 2021/0378648 A1 | 12/2021 | Thissen et al. | |
| 2021/0393334 A1 | 12/2021 | Wilson et al. | |
| 2022/0079738 A1 | 3/2022 | Schaefer et al. | |
| 2022/0087715 A1 | 3/2022 | Van Bladel et al. | |
| 2022/0168036 A1 | 6/2022 | Wei | |
| 2022/0183714 A1 | 6/2022 | Podmore et al. | |
| 2022/0323148 A1 | 10/2022 | Rothstein et al. | |
| 2023/0077068 A1 | 3/2023 | Tamir et al. | |
| 2023/0129792 A1 | 4/2023 | Hartman et al. | |
| 2023/0233349 A1 | 7/2023 | Desai et al. | |
| 2023/0248343 A1 | 8/2023 | Muse et al. | |

FOREIGN PATENT DOCUMENTS

| | | | |
|---|---|---|---|
| CN | 115024797 A | 9/2022 | |
| EP | 1132059 B1 | 3/2005 | |
| EP | 3542763 A1 | 9/2019 | |
| FR | 2903292 A1 | 1/2008 | |

(56)     References Cited

FOREIGN PATENT DOCUMENTS

| | | | |
|---|---|---|---|
| JP | 2008538937 A | 11/2008 | |
| JP | 2014534874 A | 12/2014 | |
| JP | 2019503232 A | 2/2019 | |
| NL | 1008178 C2 | 8/1999 | |
| WO | WO-2006057920 A2 | 6/2006 | |
| WO | WO-2008005405 A2 | 1/2008 | |
| WO | WO-2009155561 A2 | 12/2009 | |
| WO | WO-2012071095 A1 | 5/2012 | |
| WO | WO-2014114798 A1 | 7/2014 | |
| WO | WO-2017074719 A1 | 5/2017 | |
| WO | 2019/089135 A1 | 5/2019 | |
| WO | WO-2019183372 A1 * | 9/2019 | ............ A61B 18/14 |
| WO | WO-2020022842 A1 | 1/2020 | |
| WO | WO-2020053830 A1 | 3/2020 | |
| WO | WO-2021092576 A1 | 5/2021 | |
| WO | WO-2022066097 A1 | 3/2022 | |
| WO | WO-2022066631 A1 | 3/2022 | |
| WO | WO-2022154959 A1 | 7/2022 | |
| WO | WO-2022197680 A1 | 9/2022 | |
| WO | WO-2022231726 A1 | 11/2022 | |
| WO | WO-2023076667 A1 | 5/2023 | |
| WO | WO-2023139576 A1 | 7/2023 | |
| WO | WO-2024006230 A1 | 1/2024 | |
| WO | WO-2024191984 A1 | 9/2024 | |

OTHER PUBLICATIONS

Babaliaros. Intentional Percutaneous Laceration of the Anterior Mitral Leaflet to Prevent Outflow Obstruction During Transcatheter Mitral Valve Replacement: First-in-Human Experience. JACC Cardiovasc Interv. Apr. 24, 2017; 10(8): 798-809. doi:10.1016/j.jcin.2017.01.035. 24 pages.

International Search Report and Written Opinion received for PCT Patent Application No. PCT/US21/18383, mailed on May 20, 2021, 14 pages.

International Search Report and Written Opinion received for PCT Patent Application No. PCT/US21/20446, mailed on Jun. 18, 2021, 16 pages.

Kasel. International Lampoon: first European experience with laceration of the anterior mitral valve leaflet prior to transseptal transcatheter mitral valve implantation. EuroIntervention. Sep. 20, 2018; 14(7): 746-749. doi:10.4244/EIJ-D-18-00201. 7 pages.

Khan. Intentional Laceration of the Anterior Mitral Valve Leaflet to Prevent Left Ventricular Outflow Tract Obstruction During Transcatheter Mitral Valve Replacement: Pre-Clinical Findings. JACC Cardiovasc Interv. Sep. 12, 2016; 9(17): 1835-1843. doi:10.1016/j.jcin.2016.06.020. 15 pages.

* cited by examiner

TRANSCATHETER TISSUE CUTTING SYSTEM

CROSS-REFERENCE TO RELATED APPLICATION

This application is a national phase application of PCT Application No. PCT/US2021/018383, internationally filed on Feb. 17, 2021, which claims the benefit of Provisional Application No. 62/984,554, filed Mar. 3, 2020, which are incorporated herein by reference in their entireties for all purposes.

FIELD

The present disclosure relates generally to tissue cutting systems, and more specifically to tissue cutting systems forming part of a delivery system for an implant, such as a prosthetic valve, including associated devices, systems and methods.

BACKGROUND

Prosthetic valves have been developed to replace native valves or otherwise augment physiology. Prosthetic valves may employ flexible leaflets fabricated from biological tissue or synthetic materials. Many conventional prosthetic valve designs require delivery to a target region within a patient's anatomy via open-heart surgical techniques, though alternative approaches using transcatheter techniques have been developed and can offer advantages. Among other examples, a transcatheter prosthetic valve that is delivered endovascularly can help minimize patient trauma as compared to surgical procedures.

However, transcatheter techniques are not without their own challenges, including properly accessing treatment regions within the anatomy, properly positioning the prosthetic valve for deployment, and depending on the particular anatomy being repaired or augmented, unwanted impact from surrounding anatomy on prosthetic valve performance or unwanted impact from the prosthetic valve on the performance of the surrounding tissue, each of which can negatively impact patient health.

SUMMARY

According to a first example ("Example 1"), a delivery system includes a delivery device, an implant, optionally a prosthetic valve, having a support structure, the implant being releasably coupled to the delivery device, and a tissue cutting system coupled to the delivery device and the implant, the tissue cutting system including a cutting element configured to cut tissue.

According to another example ("Example 2"), delivery system of Example 1, wherein the cutting element forms a loop portion that extends radially outward relative to the delivery device, and optionally wherein the loop portion is configured to be adjusted in size by a user.

According another example ("Example 3"), further to the delivery system of Examples 1 or 2, wherein the cutting element includes a body that is operable to cut tissue and a protective cover, the protective cover rendering at least a portion of the body inoperable for cutting tissue.

According another example ("Example 4"), further to the delivery system of Examples 1 or 2, wherein the cutting element includes a body formed of conductive material.

According to another example ("Example 5"), further to the delivery system of any preceding claim, further comprising an outer sheath retractably disposed over at least a portion of the cutting element.

According to another example ("Example 6"), further to the delivery system of Example 5, the outer sheath comprises a thermally insulating material.

According to another example ("Example 7"), further to the delivery system of Example 5, the outer sheath comprises an electrically insulating material.

According to another example ("Example 8"), further to the delivery system of Example 5, the outer sheath comprises an abrasion-resistant material.

According to another example ("Example 9"), further to the delivery system of any preceding Example the support structure comprises a leaflet frame subcomponent and an anchor frame subcomponent.

According to another example ("Example 10"), further to the delivery system of Example 9, the support structure further comprises an interstage coupling the leaflet frame subcomponent and the anchor frame subcomponent.

According to another example ("Example 11"), further to the delivery system of Examples 8 or 9, the cutting element is coupled to a framework of the leaflet frame subcomponent or the anchor frame subcomponent.

According to another example ("Example 12"), further to the delivery system of Example 10, the cutting element is coupled to the interstage.

According to another example ("Example 13"), further to the delivery system of any preceding Example, the support structure is configured to be self-expanding.

According to another example ("Example 14"), further to the delivery system of any preceding Example, the cutting system includes a current source coupled to the cutting element.

According to another example ("Example 15"), further to the delivery system of any preceding Example, the support structure is configured to assume a collapsed, delivery configuration and an expanded, deployed configuration.

According to another example ("Example 16"), further to the delivery system of any preceding Example, the cutting element is configured to cut tissue when the implant is in a deployed configuration.

According to another example ("Example 17"), further to the delivery system of Example 16, the cutting element is configured to be uncoupled from the delivery system and/or the implant.

According to another example ("Example 18"), a method of delivering an implant, optionally a prosthetic valve, to a treatment site, includes positioning the implant at the treatment site with a delivery device; and cutting tissue, optionally a valve leaflet at the treatment site with the cutting element, the cutting element being coupled to the delivery device and the implant.

According to another example ("Example 19"), further to the method of Example 18, the cutting element defines a loop portion, the method further comprising adjusting a size of the loop portion prior to cutting the tissue.

According to another example ("Example 20"), further to the method of Examples 18 or 19, the method includes uncoupling the cutting element from the implant after the tissue is cut, and removing the cutting element from the treatment site.

According to another example ("Example 21"), further to the method of any one of claims 18-20, the method further includes deploying the implant at the treatment site, wherein the tissue is cut at least one of prior to, during, or following deploying the implant.

According to another example ("Example 22"), a method for treating a human patient with a diagnosed condition or disease associated with valve insufficiency or valve failure of a native valve, the method comprising implanting the implant of any of claims 1 to 17, the implant being a prosthetic valve, the prosthetic valve being implanted at or adjacent to a location associated with the native valve.

While multiple embodiments are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Figures 1A, 1B:
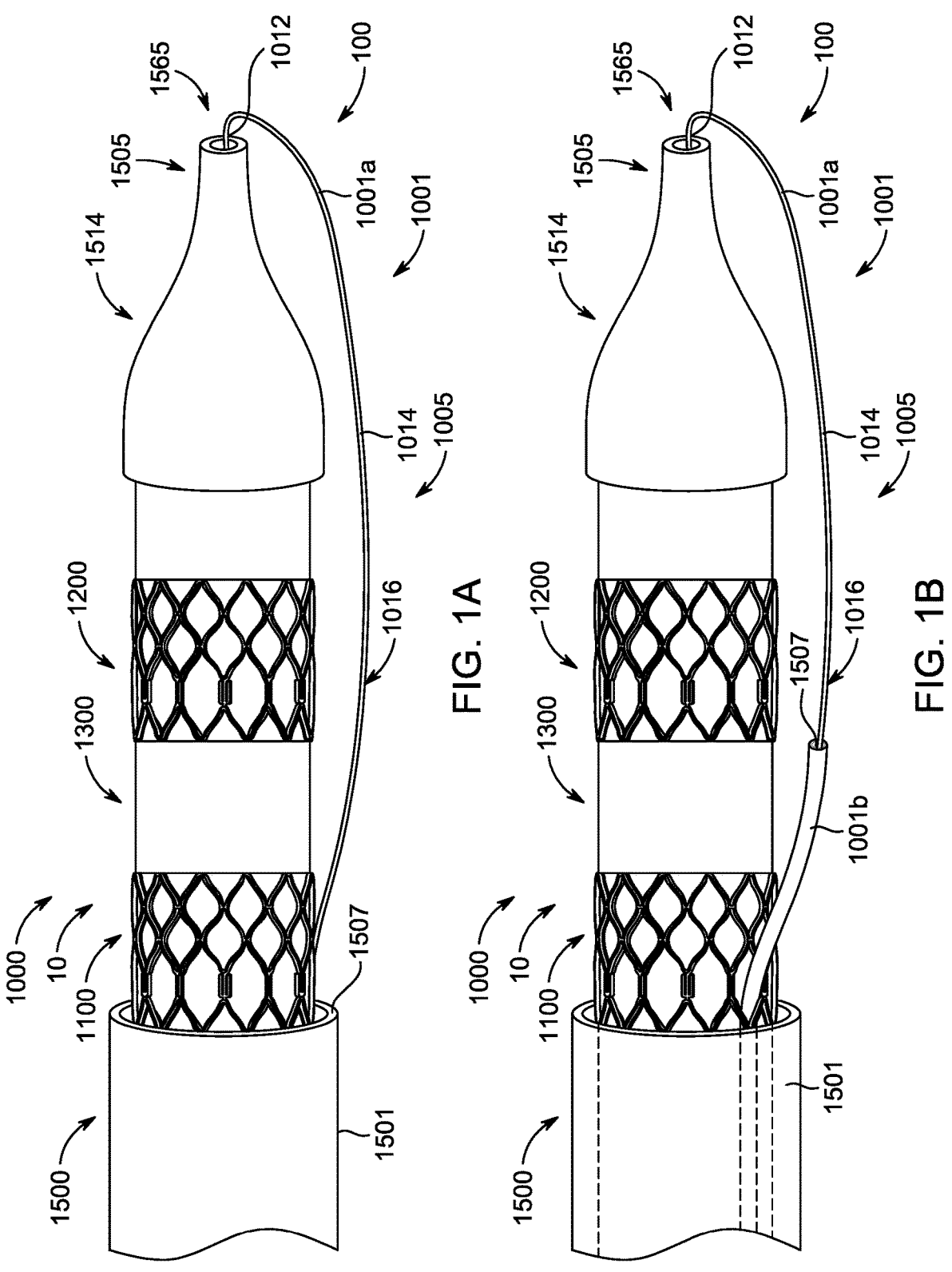
FIG. 1A is a partial side view of a delivery system, according to some embodiments.
FIG. 1B is a partial side view of a delivery system, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

With respect to terminology of inexactitude, the terms "about," "approximate," and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example.

The term "membrane" as used herein refers to a sheet of material comprising a single composition, such as, but not limited to, expanded fluoropolymer.

The term "composite material" as used herein refers to a material including two or more material components with one or more different material properties from the other. In some examples, a composite material includes at least a first material component in the form of a membrane and a second material component in the form of a polymer that is combined with the membrane (e.g., by coating and/or imbibing processes). The term "laminate" as used herein refers to multiple layers of membrane, composite material, or other materials, such as, but not limited to a polymer, such as, but not limited to an elastomer, elastomeric or non-elastomeric material, and combinations thereof.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material as is generally known.

The term "film" as used herein generically refers to one or more of the membrane, composite material, or laminate. The term "film" also includes fabric and other suitable materials.

The term "biocompatible material" as used herein generically refers to any material with biocompatible characteristics including synthetic materials, such as, but not limited to, a biocompatible polymer, or a biological material, such as, but not limited to, bovine pericardium. Biocompatible material may comprise a first film and a second film as described herein for various embodiments.

As used herein, "couple" means to join, connect, attach, adhere, affix, or bond, whether directly or indirectly, and whether permanently or temporarily.

As used herein, "native leaflet" is used to describe the leaflet of a native heart valve.

The term "leaflet" or "leaflet construct", which comprises a plurality of leaflets, as used herein in the context of prosthetic valves is a component of a one-way valve wherein the leaflet is operable to move between an open and closed position under the influence of a pressure differential. In an open position, the leaflet allows fluid (e.g., blood) to flow through the valve. In a closed position, the leaflet substantially blocks retrograde flow through the valve by occluding the valve orifice. In embodiments comprising multiple leaflets, each leaflet cooperates with at least one neighboring leaflet or secondary structure to block the retrograde flow of blood. The pressure differential in the blood is caused, for example, by the contraction of a ventricle or atrium of the heart, such pressure differential typically resulting from a fluid pressure building up on one side of the leaflets when closed, for example, by the contraction of a ventricle or atrium of the heart. As the pressure on an inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve rises above the blood pressure on the inflow side of the valve, the leaflet returns to the closed position generally preventing retrograde flow of blood through the valve.

It is appreciated that leaflets, where not required by the specific design or mode of function of the disclosed embodiment, may be rigid such as in mechanical valves or may be flexible as in bioprosthetic and synthetic valves. It is further appreciated that, although embodiments provided herein include a frame that supports the leaflets, the leaflets may not necessarily be supported by a frame. In other embodiments, the leaflets may be constructed as in the tissue valve art that are formed into the desired shape without a frame.

The term "frame" as used herein generically refers to any structure or support used to directly or indirectly support leaflets for use in the prosthetic valve. It will be understood that, where appropriate, that the term frame may be used interchangeably with support structure. In accordance with some embodiments, the leaflets may be supported by the wall of a solid-walled conduit, the solid-walled conduit being understood to be a frame or support structure.

The term "frame element" as used herein refers to any portion of a leaflet frame or outer frame, such as, but not limited to, those individual portions that define a leaflet window or aperture.

The term "cutting" as used in the context of the present disclosure includes slicing, splitting, puncturing, tearing, and/or physically separating material, such as body tissue. For example, when a native leaflet as previously defined is cut, the resulting native leaflet may be partially split, torn, or separated to form a gap between two or more subsections thereof. The definition of "cut" may further include a result of one or more incision, laceration, bisection, separation, etc. Furthermore, the native leaflet does not necessarily need to be completely separated into two or more components that can move freely relative to each other; for example, the native leaflet may be at least partially separated, where the definition of "partially" may include 10%, 20%, 30%, 40%, 50%, 60%, 70%, 80%, 90%, or any range therebetween of a diameter or an edge-to-edge distance of the native leaflet to be cut.

As used herein, "native valve orifice" refers to a location into which the prosthetic valve may be placed. A native valve orifice includes a tissue orifice which includes anatomical structures into which a prosthetic valve can be placed. Such anatomical structures include, but are not limited to, a location wherein a cardiac valve may or may not have been surgically removed. Other anatomical structures that can receive a prosthetic valve include, but are not limited to, veins, arteries, ducts and shunts. A native valve orifice may also refer to a location in a synthetic or biological conduit that may receive a prosthetic valve.

Description of Various Embodiments

The present disclosure relates generally to tissue cutting systems, and more specifically to tissue cutting systems forming part of a delivery system for an implant, such as a prosthetic valve, including associated devices, systems and methods. Such tissue cutting systems may include a cutting element and/or other features coupled to the implant and/or other portions of the delivery system for the implant. Examples of implants include those having a support structure, such as prosthetic valves used for cardiac valve replacement or other applications associated with valves and valve orifices, as well as any of a variety of endoluminal applications and associated implants, including stents, stent grafts, endovascular filters, and others.

In various delivery system embodiments, a cutting system is incorporated with the delivery system to cut tissue in association with delivery of an implant to a treatment site.

For example, the delivery system, and in particular the cutting system, may be configured for cutting one or more of native leaflets of a native valve being replaced by a prosthetic valve, where a portion of the cutting system is coupled to the prosthetic valve or other portions of the delivery system.

The cutting element, and the cutting system more generally, is configured to cut a tissue and, in some examples, is configured as an electrosurgical cutting system including a cutting element in the form of a wire that is activated by applying electrical current to the wire. The cutting element may be coupled to the support structure of the implant. For example, in the case where the implant is a prosthetic valve, the cutting element may be coupled to a valve frame subcomponent and/or an anchor frame subcomponent (in embodiments when present) and/or an interstage (in embodiments when present) flexibly coupling the anchor frame subcomponent and the valve frame subcomponent of the prosthetic valve.

Delivery/Transcatheter Cutting Systems

FIG. 1A shows a delivery system 10 including an implant, which is a prosthetic valve 1000 as shown. The prosthetic valve 1000 is shown coupled to a delivery device 1500 with the prosthetic valve 1000 in a predeployed configuration. As shown, the prosthetic valve 1000 includes an anchor frame subcomponent 1100 and leaflet frame subcomponent 1200 that are longitudinally offset from one another (also referred to as being positioned in series for delivery). The anchor frame subcomponent 1100 and the leaflet frame subcomponent 1200 are coupled together with an interstage 1300 extending between the anchor frame subcomponent 1100 and the leaflet frame subcomponent 1200. The anchor frame subcomponent 1100 may be omitted in certain designs (e.g., FIG. 1C) with the leaflet frame subcomponent 1200 forming the support structure, but when present, the anchor frame subcomponent 1100 and the leaflet frame subcomponent 1200 may together define the support structure for the prosthetic valve 1000. Alternatively, the prosthetic valve 1000 may only include leaflet frame subcomponent 1200 which defines the support structure of the prosthetic valve 1000.

As shown in FIG. 1A, the delivery system 10 includes a transcatheter cutting system 100, which will be described in further detail below. As shown, the transcatheter cutting system 100 includes a cutting element 1001 that extends from a central lumen 1565 of the delivery device 1500 (e.g., from a tip portion 1514 of the delivery device 1500), and more specifically through an outlet end 1505 of the central lumen 1565 of the delivery device 1500. For reference, the central lumen 1565 optionally extends along the length (e.g., an entire length) of the delivery device 1500 and terminates at the outlet end 1505. The delivery system 10 may also include an outer sheath 1501 that extends over the delivery device 1500 and/or the transcatheter cutting system 100. As described below, the outer sheath 1501 may be extended or retracted as part of delivering the prosthetic valve 1000 (e.g., to permit expansion thereof) and/or as part of revealing portions of the transcatheter cutting system 100 so those portions are activatable for cutting tissue.

In some examples, the cutting element 1001 may include a body 1001*a* and a protective cover 1001*b* (FIG. 1B). The cutting element 1001 may be configured as an electrosurgical wire that is activated for cutting tissue upon applying an electrical current to the electrosurgical wire. In some examples, an active portion of the cutting element 1001 (e.g., an exposed portion of the body 1001*a* of the cutting element 1001) has a shape (e.g., an exposed length) that approximates a desired length of cut, or in different terms, the final amount of cutting that is to be performed. In this sense, the cutting element 1001 may be positioned against or adjacent tissue, electrically activated, and a resulting cut of a desired configuration (length, width, or other characteristic) is generated in the tissue. In some examples, the cutting element 1001 configured to cut tissue by either directly engaging or being positioned adequately close to the tissue and then drawn or otherwise translated along a desired cutting path (e.g., either in one direction, or in a back-and-forth motion) to provide a desired cut configuration (again, length, width, or other characteristic).

The body 1001*a* of the cutting element 1001 may be configured as a relatively smooth wire (e.g., monofilament, multi-filament (e.g., braided), or other type) where the cutting operation is performed primarily or entirely via delivery of electrical energy. In some examples, the body 1001*a* of the cutting element 1001 may include functional surface cutting features (e.g., one or more serrated, pointed, or relatively roughened edges) to direct electrical energy to specific locations along the body 1001*a* of the cutting element 1001 (e.g., to focus the electrical energy) and/or to provide mechanical cutting functionality to the cutting element.

In some examples, the cutting element 1001 is configured such that only a portion, or a selected section, is operable for cutting, while other portions of the cutting element 1001 are not operable, or inoperable, for cutting. In various examples, the protective cover 1001*b* extends over one or more portions of the cutting element 1001 to help prevent unwanted cutting of non-targeted tissue and/or delivery system features along those one or more portions of the cutting element 1001. In some examples, the protective cover 1001*b* is electrically insulating to help avoid delivery of electrical energy from portions of the body 1001*a* covered by the protective cover 1001*b*. In some examples, the protective cover 1001*b* additionally or alternatively acts to cover one or more portions of the body 1001*a* configured for mechanical cutting to help avoid mechanical cutting of tissue along those portions of the body 1001*a* covered by the protective cover 1001*b*.

As shown, the cutting element 1001 has a first leg 1012 that extends distally from the outlet end 1505, beyond the tip portion 1514 of the delivery device 1500, and then curves back proximally to define a second leg 1014 which extends into the delivery device 1500 proximal from the tip portion 1514. In this manner, the cutting element 1001 defines a looped, or arcuate segment, called out as a loop portion 1016. The loop portion 1016 may be adjustable in configuration (e.g., overall width, size, and/or transverse/radial extension relative to the delivery device 1500) by adjusting the length of loop portion 1016 (e.g., by extending or retracting the second leg 1014). In addition to being coupled to the delivery device 1500, the cutting element 1001 may be coupled with the prosthetic valve 1000. Thus, in various examples, the cutting element 1001 forms a loop portion 1016 that extends radially outward relative to the delivery device, and optionally the loop portion is configured to be adjusted in size by a user.

In some examples, the cutting element 1001 is coupled with a portion of the prosthetic valve 1000. For example, the cutting element 1001 (e.g., the second leg 1014) may extend through a portion of the anchor frame subcomponent 1100. As described further below, the anchor frame subcomponent 1100 may include a framework of frame elements defining apertures, a cover material, or other features. The cutting element 1001 may pass through such a framework as shown, and/or any cover material coupled to the framework (e.g., a film and/or a fabric cover). In some examples, the cutting element 1001 is coupled with the anchor frame subcomponent 1100 by passing through a closed cell aperture defined by the framework of the anchor frame subcomponent 1100. In some examples (e.g., where the anchor frame subcomponent and/or interstage are not present, such as in FIG. 1C), the cutting element 1001 is coupled with a different subcomponent such as the leaflet frame subcomponent 1200 or the interstage 1300, in a similar manner to that described in association with the anchor frame subcomponent 1100.

In some examples, the cutting element 1001 is activatable by applying electricity to the cutting element 1001 (e.g., the body 1001*a* of the cutting element 1001). As such, the transcatheter cutting system 100 may include a current source 1020 (FIG. 1D) that may apply current to the cutting element 1001, such as high-frequency (radio frequency) alternating polarity, electrical current to cut tissue. For reference, cutting in this context includes traditional splitting or passing entirely through tissue, as well as coagulating, desiccating, or fulgurating tissue. As such, in some examples, the material of the body 1001*a* of the cutting element 1001 is electrically conductive, including metals such as silver, copper, gold, aluminum, zinc, nickel, brass, bronze, iron, platinum, or steel as well as alloys thereof, or intrinsically conductive polymers such as polyacetylene, polypyrrole, polyindole, or polyaniline as well as copolymers thereof. These materials are examples only, and other materials (e.g., nickel-titanium alloys) can be employed as appropriate.

As referenced above, one or more portions of the body 1001*a* of the cutting element 1001 may be electrically/thermally/mechanically isolated by the protective cover 1001*b* (which may be a tube, catheter, sheath, or any other suitable configuration) that extends over at least a portion of the body 1001*a* of the cutting element 1001 so as to restrict the portions of the body 1001*a* of the cutting element 1001 that are operable for cutting. The protective cover 1001*b* may be formed of insulating polymeric materials, such as polyethylene or fluoropolymer, including but not limited to expanded polytetrafluoroethylene (ePTFE), for example, including any of the materials described in association with the prosthetic valve examples provided herein.

Because the cutting element 1001 may be partially protected/insulated, the unprotected/uninsulated portions of the cutting element 1001, and specifically the body 1001*a* of the cutting element 1001, may be considered the active portion of the cutting element 1001. In some examples, the protective cover 1001*b* may include one or more abrasion-resistant material such as Ultra-high-molecular-weight polyethylene (UHMWPE, UHMW), among others, or any suitable material with a coating applied on a surface thereof to strengthen the surface so it is resistant to abrasion. In some examples, ePTFE with a proper microstructure and/or composite material applied thereto may provide suitable abrasion resistance, durability, and the like.

In FIG. 1A, an active portion 1005 is defined by the exposed portion of the body 1001*a* of the cutting element 1001 between the outlet end 1505 of the central lumen 1565 of the delivery device 1500 and the portion of the anchor frame subcomponent 1100 to which the cutting element 1001 couples. For reference, the protective cover 1001*b* is shown in FIG. 1B, but is either fully retracted or not present in FIG. 1A. In some examples, the outer sheath 1501 of the delivery system 10 may be translated (e.g., extended and retracted) relative to the delivery device 1500 and the transcatheter cutting system 100 (more specifically, the cutting element 1001). In different terms, the outer sheath 1501 may be retractably disposed over at least a portion of the cutting element 1001. The outer sheath 1501 may be formed of any of the materials described in association with the protective cover 1001*b* and thus may serve as an insulating/protective cover for the cutting element 1001. In different terms, the outer sheath 1501 may be extended or retracted to alter the active portion 1005 of the body 1001*a* of the cutting element 1001. The outer sheath may include a thermally insulating material, an electrically insulating material, and/or an abrasion-resistant material.

As described below, in some examples, the protective cover 1001*b* may be translated over the body 1001*a* to alter the length of the active portion 1005 (e.g., by extending or retracting the protective cover 1001*b* over the body 1001*a* so that at least a portion of the protective cover 1001*b* covers at least a portion of or the entirety of prosthetic valve 1000, the active portion 1005 would be defined by the portion of the cutting element 1001 located between the outlet end 1505 of the delivery device 1500 and an outlet end 1507 of the outer sheath 1501. FIG. 1B shows the prosthetic valve 1000 as loaded on the delivery device 1500 according to some embodiments. The active portion 1005 of the body 1001*a* of the cutting element 1001 is defined as the exposed portion of the body 1001*a* between the end of the central lumen 1565 and the protective cover 1001*b*.

Figures 1C, 1D:
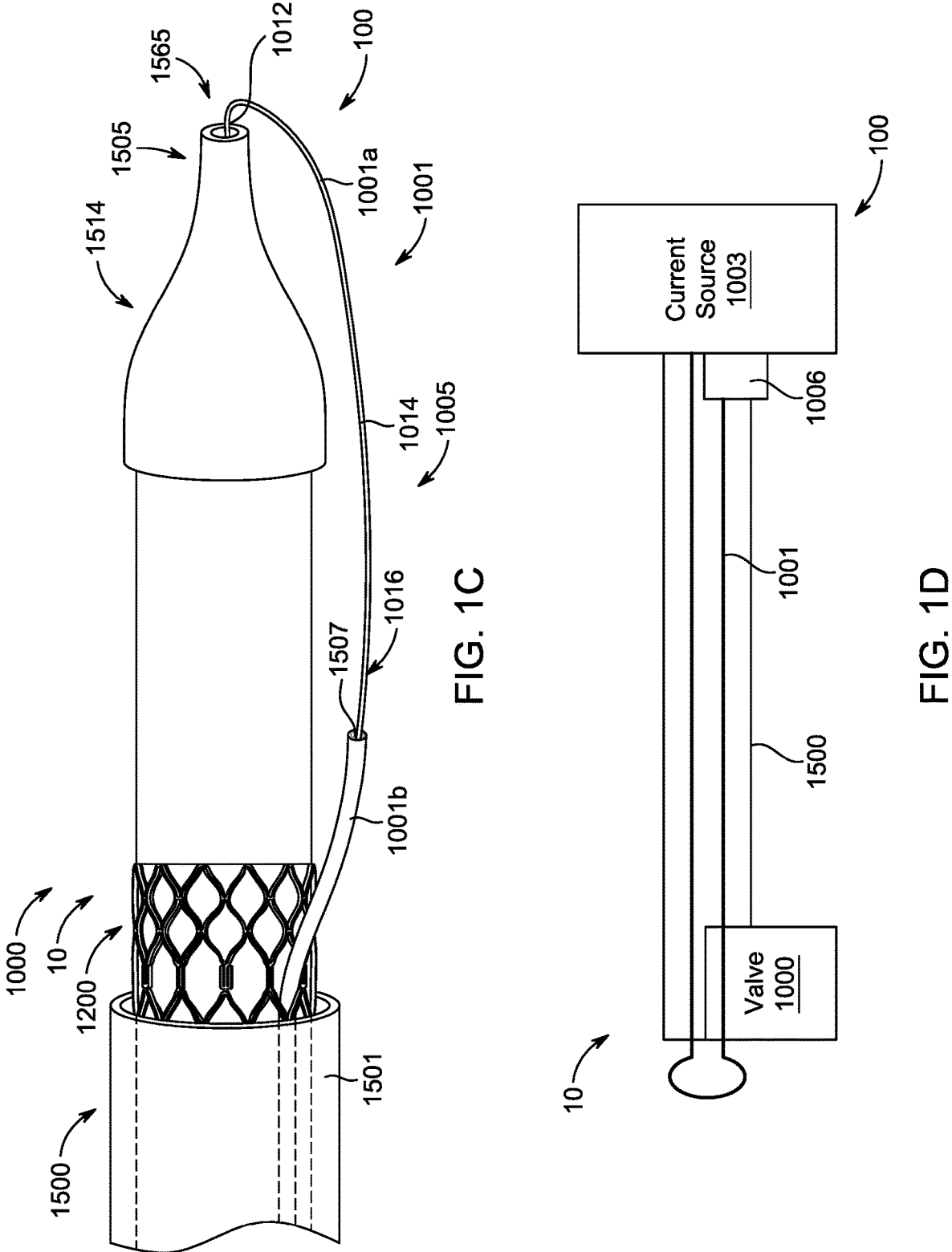
FIG. 1C is a partial side view of a delivery system, according to some embodiments.
FIG. 1D is a schematic diagram of a delivery system, according to some embodiments.

FIG. 1C illustrates an example of the delivery system 10 where the prosthetic valve 1000 includes the leaflet frame subcomponent 1200 and omits an anchor frame subcomponent (such as anchor frame subcomponent 1100) and interstage (such as interstage 1300).

FIG. 1D is a schematic representation of the prosthetic valve 1000 (or any implant) and the cutting element 1001 as implemented in the transcatheter cutting system 100 including a current source 1003 and a locking mechanism 1006 (for example a clamp) attached at a proximal end of the delivery system 10. As indicated, the cutting element 1001 is electrically coupled to the current source 1003, passes through the delivery device 1500, exits from the outlet end of the delivery device 1500, defines the active portion 1005, returns back into the delivery device 1500 (e.g., passing the prosthetic valve 1000 back into the delivery device 1500), and couples with the current source 1003 to form a circuit which, when the current source 1003 is activated, causes the cutting element 1001 to be activated and operable for cutting tissue. The locking mechanism 1006 helps ensure that at least one end of the cutting element 1001 is locked in place and does not slidably move during a valve deployment procedure to deploy the prosthetic valve 1000 at a desired location within a patient's body, which will be explained in detail further below.

Prosthetic Valve Implant Examples

As an implant, the prosthetic valve may include a support structure formed by one or more frame elements or frame members (e.g., connected by an interstage component) and one or more covers. For example, the support structure may include a leaflet frame subcomponent and an optional anchor frame subcomponent, as well as an interstage between the leaflet frame subcomponent and the anchor frame subcomponent as applicable.

In various examples, the prosthetic valve is operable as a one-way prosthetic valve that defines a valve orifice into which leaflets open to permit flow and close so as to block or occlude the valve orifice and partially or entirely prevent flow in response to differential fluid pressure. In some examples, such prosthetic valves include a support structure (e.g., one or more frame subcomponents) and a leaflet construct coupled to the support structure.

In the instant disclosure, the prosthetic valve examples and associated methods of delivery are primarily described in association with transcatheter cardiac valve applications (e.g., for native mitral valve replacement) although it should be readily appreciated embodiments within the scope of this disclosure can be applied toward any implant of similar structure and/or function. For example, though primary examples include prosthetic valves, the implant can be configured for use in respiratory or gastrointestinal tract applications and/or may be a stent, graft, stent graft, endovascular filter, occluder, or other type of implant.

Various implant examples presented herein include a prosthetic valve that includes a leaflet frame subcomponent. In some examples, there is an optional anchor frame subcomponent and an interstage flexibly disposed between (e.g., coupling) the leaflet frame subcomponent and the anchor frame subcomponent. The leaflet frame subcomponent further includes leaflets that operate as a one-way valve. When present, the anchor frame subcomponent may be operable to help anchor the prosthetic valve to an implant site. The associated interstage may be operable to perm it the translation of the leaflet frame subcomponent into the anchor frame subcomponent during a deployment sequence, also described as nesting or telescoping of the two frame subcomponents. In accordance with some embodiments, the interstage is operable to permit perfusion during deployment.

In embodiments comprising multiple leaflets, each leaflet generally cooperates with at least one neighboring or adjacently situated leaflet to block or restrict the retrograde flow of blood. The pressure differential in the blood is caused, for example, by the contraction of a ventricle or atrium of the heart, such pressure differential typically resulting from a fluid pressure building up on one side of the leaflets when closed. As the pressure on the inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

As will be describe further below, in various examples, the prosthetic valve provides a leaflet frame subcomponent that essentially floats within an anchor frame subcomponent supported by the interstage and does not directly couple with a native valve orifice. The anchor frame subcomponent may conform to the shape of the native valve orifice which, for example, may not be perfectly circular, whereas the leaflet frame subcomponent does not necessarily conform to the shape of the native valve orifice. The leaflet frame subcomponent may remain cylindrical or at a preferred geometrical configuration so as to present the leaflets with a geometrically stable platform ensuring proper leaflet function, including coaptation and opening dynamics.

Although it is appreciated that the examples of the prosthetic valve may be suitable for either surgical or transcatheter applications, examples provided herein are presented as for transcatheter applications to avoid the repetition if surgical examples are also presented. Therefore, the inventive concepts are applicable for both surgical or transcatheter applications and not limited to only transcatheter applications.

Figure 2A:
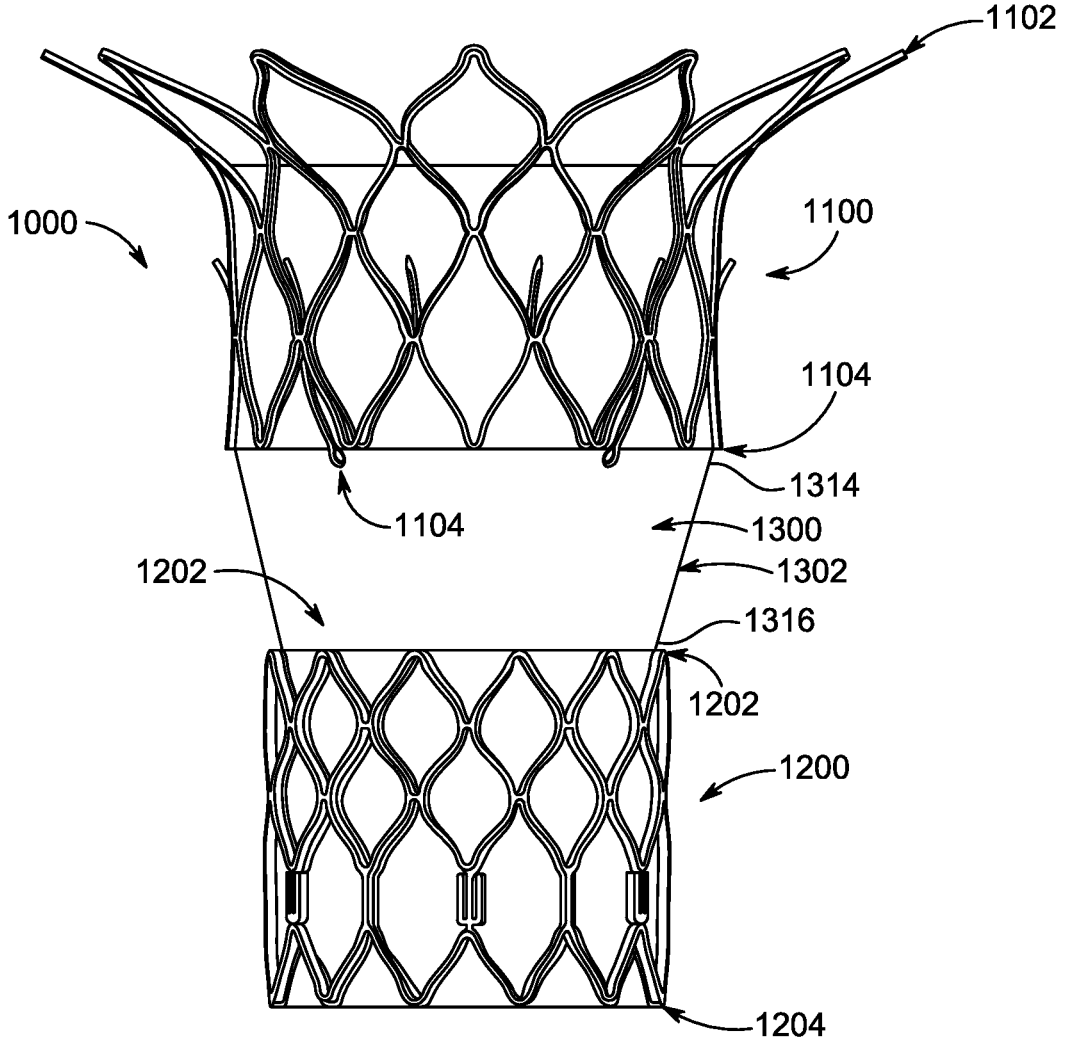
FIG. 2A is a side view of a prosthetic valve, according to some embodiments.
Figure 2B:
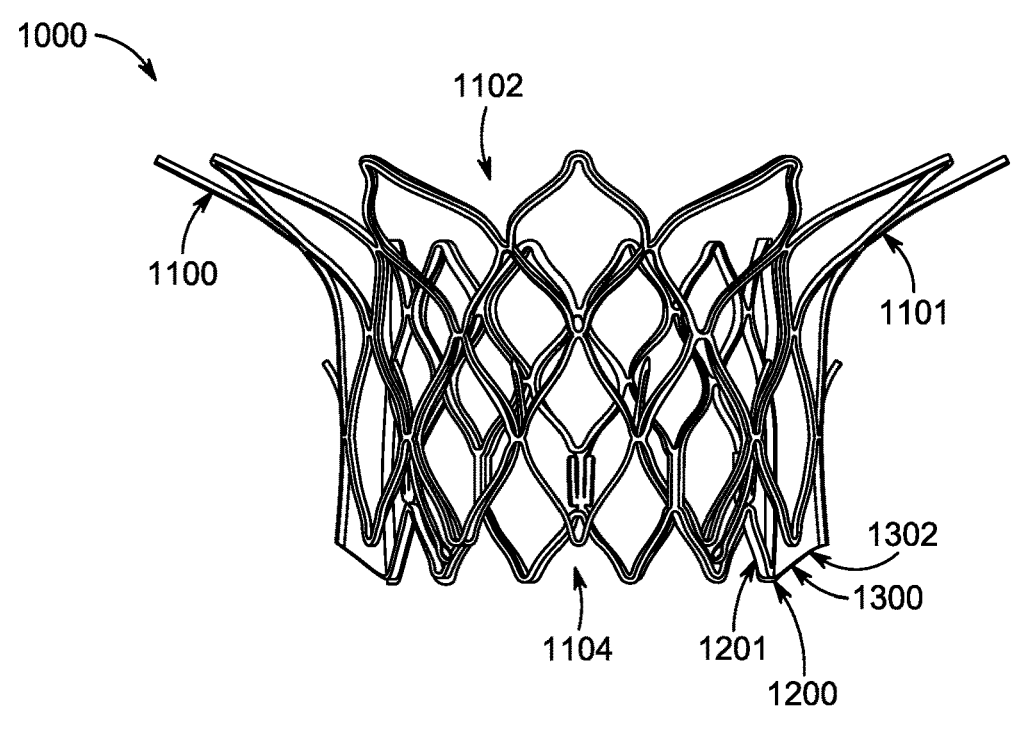
FIG. 2B is a side view of a prosthetic valve, according to some embodiments.
Figure 2C:
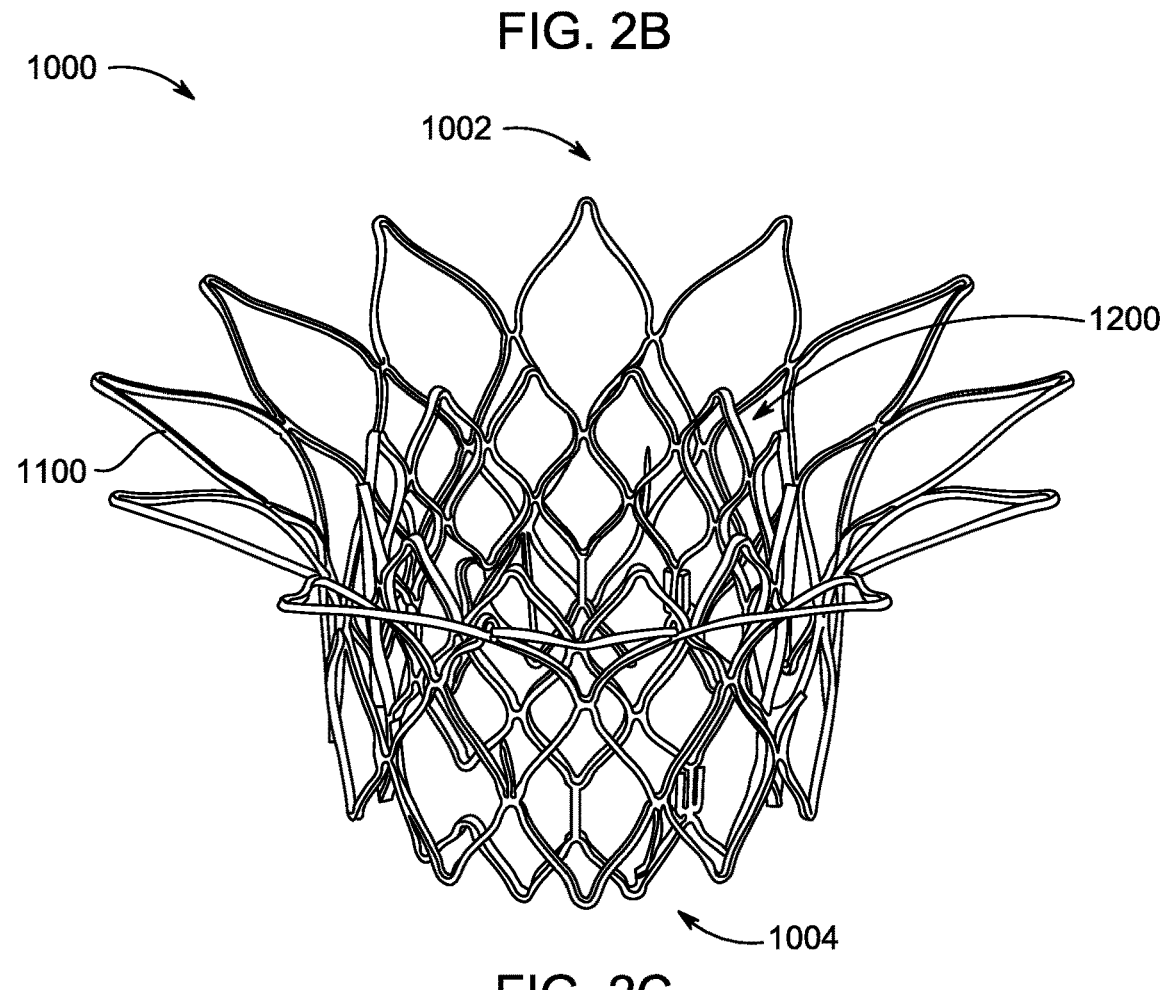
FIG. 2C is a perspective view of the prosthetic valve of FIG. 1A, according to some embodiments.
Figure 2D:
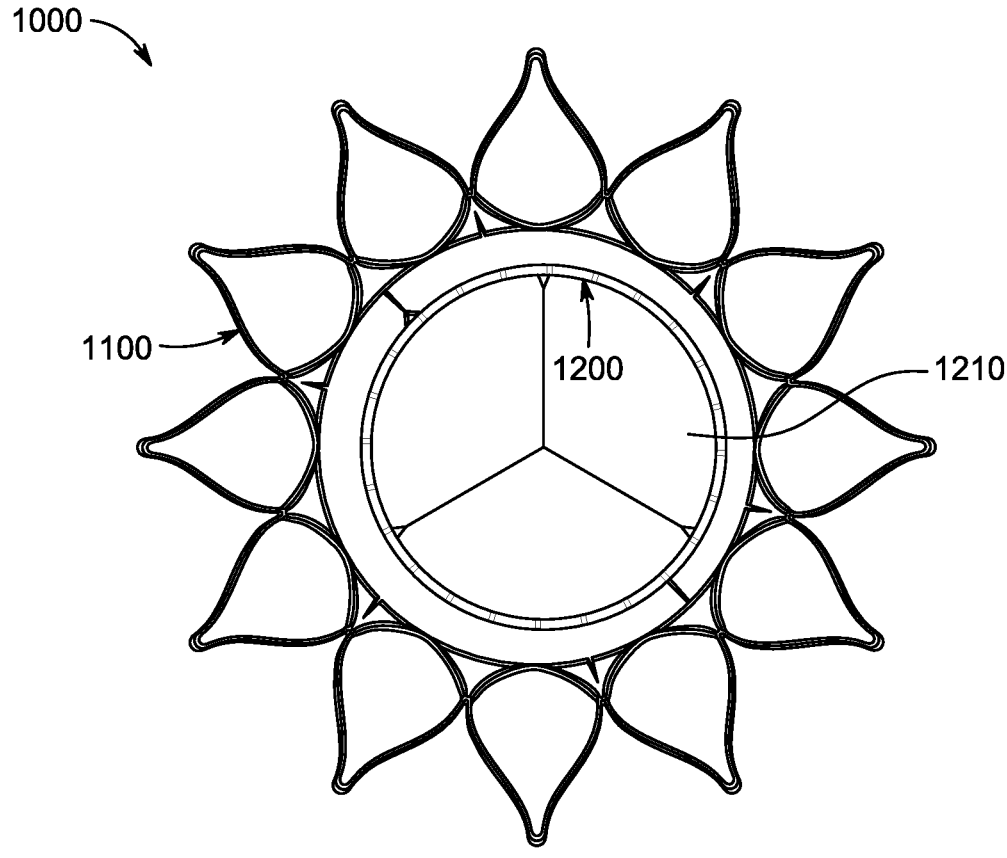
FIG. 2D is an axial view of the prosthetic valve of FIG. 1A, according to some embodiments.

With reference to FIGS. 2A and 2B, various embodiments illustrated and described herein are directed to a prosthetic valve that comprises a leaflet frame subcomponent 1200 and an anchor frame subcomponent 1100 that can be nested in-situ, which is possible because an inner diameter of the anchor frame subcomponent 1100 is greater than an outer diameter of the leaflet frame subcomponent 1200. FIG. 2A is a side view of the prosthetic valve 1000 in the unrestrained configuration (e.g., unconstrained on a benchtop) showing a leaflet frame subcomponent 1200, an anchor frame subcomponent 1100, and an interstage 1300 therebetween in coaxial serial alignment. FIG. 2B is a side view of the prosthetic valve 1000 in the deployed configuration showing the leaflet frame subcomponent 1200 translated into the anchor frame subcomponent 1100, with the interstage 1300 therebetween in nested alignment.

Leaflet Frame Subcomponent

FIG. 2A shows the prosthetic valve 1000, according to some examples. The leaflet frame subcomponent 1200 generally comprises a suitable material (e.g., a shape memory material operable to flex under load and retain its original shape when the load is removed), to allow the leaflet frame subcomponent 1200 to self-expand from a compressed shape to a predetermined shape, or to be expanded (e.g., balloon expanded) to a predetermined shape. Thus, the leaflet frame subcomponent 1200 may be plastically deformable to be expanded by a balloon, while in other embodiments the leaflet frame subcomponent 1200 is elastically deformable so as to be self-expanding. The leaflet frame subcomponent 1200 and the anchor frame subcomponent 1100 may comprise the same or different materials, and the description of the general features of each can readily be applied to the other.

The leaflet frame subcomponent 1200 provides the prosthetic valve 1000 with the functionality of a one-way valve. It is understood and appreciated that a variety of one-way valves are known and may be used herein in combination with the cutting element 1001. For example, a variety of mechanical valves, biological valves, and biological and synthetic leaflet valves may be used as the one-way valve of the leaflet frame subcomponent 1200. It is also appreciated that, for transcatheter applications, the leaflet frame subcomponent 1200 may be configured to take on a smaller-diameter compressed configuration for transcatheter delivery and a larger-diameter expanded configuration for operational use, and that in such instances the one-way valve component accommodates that functionality.

In various examples, the leaflet frame subcomponent 1200 is configured to be received within at least a portion of the anchor frame subcomponent 1100, as will be described in more detail below. It will be appreciated that nonlimiting examples of the leaflet frame subcomponent 1200 can be provided with a diameter (e.g., a diameter of an interior or exterior surface of the leaflet frame subcomponent 1200) in a range of between twenty (20) millimeters and thirty (30) millimeters, depending on a patient's anatomy, although a variety of dimensions are contemplated.

Figure 3A:
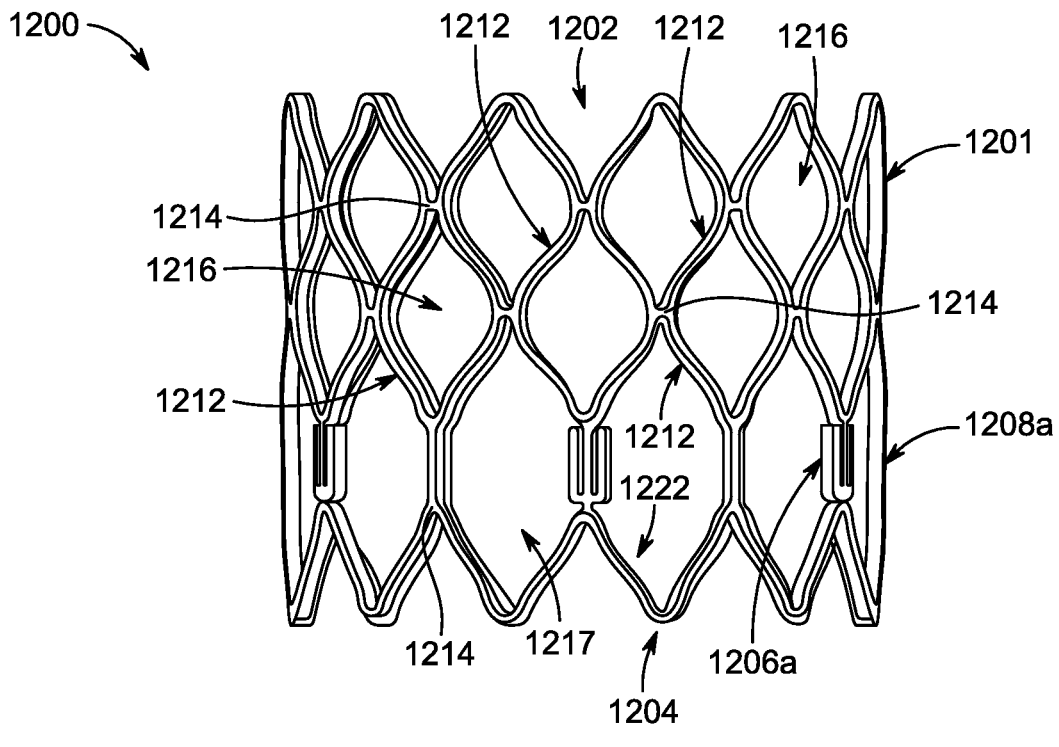
FIG. 3A is a side view of a leaflet frame of a medical device, according to some embodiments.
Figure 3B:
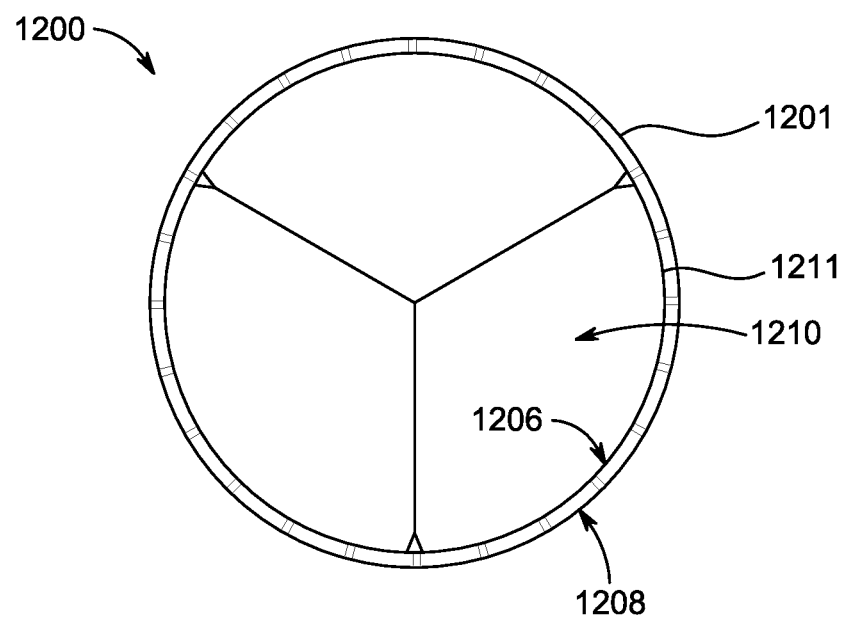
FIG. 3B is an axial view of a leaflet frame subcomponent, according to some embodiments.

FIG. 3A is a side view of the leaflet frame 1201 without leaflets 1210 or any optional covering for ease of visualizing other component features. FIG. 3B is an axial view of the leaflet frame 1201 showing the leaflets 1210 (or leaflet construct 1211). The side of the leaflet frame 1201 may be at least partially covered, such as with a film or fabric, not shown for clarity, suitable for a particular purpose, such as, but not limited to, to restrict fluid from passing through apertures of the leaflet frame 1201. For illustrative purposes, the following examples are suitable especially for a transcatheter application, but are also suitable for a surgical application. The leaflet frame subcomponent 1200 includes a leaflet frame 1201 and leaflets 1210.

The leaflet frame 1201 defines a cylindrical or tubular mesh or framework defining the apertures 1216, in accordance with an embodiment. For example, as shown, the leaflet frame 1201 includes a plurality of frame members 1212 that are interconnected and arranged in one or more patterns. In various examples, the frame members 1212 are connected to one another at joints 1214. In some examples, these joints 1214 operate as flex points so as to provide a preferential flexing location for the leaflet frame subcomponent 1200, such as to flex when compressed to a smaller delivery diameter such as required for transcatheter delivery. In some examples, one or more flex points or joints 1214 comprise sites on the leaflet frame 1201 that undergo a high degree of bending. In some examples, the flex points or joints 1214 may comprise a geometry, structural modification or material property modification, among others, that biases the leaflet frame 1201 to bend at the joints 1214 when compressed or expanded between a larger diameter and a smaller diameter.

In some examples, one or more apertures 1216 (also described as cells) are defined between the joints 1214 and the frame members 1212 of the leaflet frame 1201 that are interconnected. In instances where the apertures 1216 are bounded on all sides by frame members 1212 or other features, they may be referred to as "closed" apertures and where not bounded on all sides, "open" apertures. In some examples, these apertures 1216 extend between the leaflet frame exterior surface 1208a and the leaflet frame interior surface 1206a of the leaflet frame subcomponent 1200. As illustrated in the embodiments of FIGS. 3A and 3B, one or more of the apertures 1216 define a diamond shape when the leaflet frame subcomponent 1200 is in a deployed configuration. Upon compression to a smaller diameter (e.g., a delivery diameter), one or more of the joints 1214 and the frame members 1212 deform such that the apertures 1216 generally define an elongated diamond shape as shown in various Figures. Upon re-expanding the leaflet frame subcomponent 1200 to a larger diameter during deployment at a treatment site, the frame members 1212 that are interconnected expand to define the generally wider diamond shape and thus apertures 1216 that are generally wider (e.g., as shown generally in FIG. 4). As previously referenced, the leaflet frame subcomponent 1200 is optionally coupled to the cutting element 1001 via one or more of the apertures 1216 as desired.

It should be appreciated that while the frame members 1212 illustrated and described herein are interconnected and define apertures 1216 having generally a diamond shape, the frame members 1212 that are interconnected may be arranged in a number of alternative patterns without departing from the spirit or scope of the disclosure. That is, a number of alternative patterns are envisioned where the arrangement of frame members 1212 is configured in such a manner as to provide for a leaflet frame subcomponent 1200 that can be compressed to a smaller diameter for transcatheter delivery and subsequently expanded (or allowed to expand) to a larger diameter at a treatment site during deployment of the prosthetic valve 1000. Accordingly, the disclosure should not be limited to arrangements of the frame members 1212 that define apertures 1216 that are diamond-shaped. For example, a framework of the leaflet frame subcomponent 1200 can define any number of features, repeatable or otherwise, such as geometric shapes and/or linear or meandering series of sinusoids. Geometric shapes can comprise any shape that facilitates circumferential compressibility and expandability.

In various embodiments, the leaflet frame 1201 may comprise or otherwise be formed from a cut tube, or any other element suitable for the particular purpose of the frame as described herein. It is appreciated that the frame can be formed via various manufacturing processes, including, but not limited to, additive manufacturing, subtractive manufacturing, and injection molding. For example the frame may be formed of wire or braided wire, formed by three-dimensional printing, as well as formed by etching, cutting, laser cutting, and stamping sheets or tubes of material, among other suitable processes, into an annular or tubular structure or, if a sheet of material, with the sheet then formed into an annular or tubular structure. In various examples, the frame can comprise, such as, but not limited to, any biocompatible and, in those embodiments where applicable, elastically deformable metallic or polymeric material including shape-memory materials, such as nitinol, a nickel-titanium alloy. Other materials suitable for the frame include, but are not limited to, other titanium alloys, stainless steel, biocompatible alloys (e.g., cobalt-chromium alloy, cobalt-nickel alloy, nickel-chromium alloy, or nickel-cobalt-chromium-molybdenum alloy, such as MP35N® alloy (SPS Technologies, Jenkintown, Pa.)), polymers, polypropylene, polyethylene terephthalate, PEEK, acetyl homopolymer, acetyl copolymer, other alloys, polymers, and thermoplastics, or any other material that is generally biocompatible having adequate physical and mechanical properties to function as a frame as described herein, or combinations thereof.

It is understood that when the frame is constructed of a plastically-deformable material, the frame, and thus the prosthetic valve, can have a lower radial dimension when coupled to the delivery catheter and then can be expanded to a larger radial dimension inside a patient, either by internal forces or by external forces, such as by an inflatable balloon or equivalent expansion mechanism. When constructed of an elastic material, the frame, and thus the prosthetic valve, can be crimped to a radially collapsed configuration and restrained in the collapsed configuration by, for example, insertion into a sheath or constrained by fibers or other constraining mechanism. Once inside the body, the prosthetic valve can be released from the constraining mechanism, which allows the prosthetic valve to expand to its functional size.

In various examples, the leaflet frame 1201 is elastically deformable so as to be self-expanding under spring bias forces, as those of skill will appreciate. In some examples, the leaflet frame 1201 is plastically deformable so as to be mechanically expanded such as with a balloon, as those of skill will appreciate. In yet some other examples, the leaflet frame 1201 is plastically deformable as well as elastically deformable. That is, in some examples, the leaflet frame 1201 includes one or more elastically deformable components or features and one or more plastically deformable components or features. Thus, it should be appreciated that the examples of the leaflet frame 1201 presented herein are not to be limited to a specific design or mode of expansion.

The leaflet frame 1201 can be made of any of various suitable plastically-expandable materials (e.g., stainless steel, etc.) or self-expanding materials (e.g., nickel titanium alloy (NiTi), such as nitinol), in accordance with embodiments. When constructed of a plastically-expandable material, the frame, and thus the prosthetic valve 1000, can be compressed to a radially collapsed configuration in the delivery device 1500 and then expanded inside a patient by an inflatable balloon or equivalent expansion mechanism (not shown). When constructed of a self-expandable material, the frame, and thus the prosthetic valve 1000, can be crimped to a radially collapsed configuration and restrained in the collapsed configuration by insertion into a sheath or equivalent mechanism of the delivery device 1500. Once inside the body, the prosthetic valve 1000 can be advanced from the delivery sheath which allows the prosthetic valve to expand to its functional size.

Suitable plastically-expandable materials that can be used to form the frames include, without limitation, stainless steel, biocompatible alloys (e.g., cobalt-chromium or nickel-cobalt-chromium alloys), polymers, or combinations thereof. In some embodiments, the frame is made of a nickel-cobalt-chromium-molybdenum alloys, such as MP35N® alloy (SPS Technologies, Jenkintown, Pa.).

In some methods of making the leaflet frame 1201, a pattern of the apertures 1216 may be cut into a tube to form an annular-shaped cut stent frame or support structure defining the leaflet frame 1201. As shown, the apertures 1216 may generally be arranged into rows forming the annular shape of the support structure. The leaflet frame 1201 may be formed or otherwise configured such that the apertures 1216 have differing sizes and/or configurations (e.g., one or more rows of smaller apertures and one or more rows of larger apertures as shown).

In various embodiments, the leaflet frame subcomponent 1200 additionally supports or otherwise includes a valve structure. In some examples, the valve structure includes one or more leaflets 1210 as shown in FIG. 1D. A variety of mechanical valve leaflet, biological leaflet, and synthetic leaflet designs are known in the medical technology arts, any of which may be incorporated into the leaflet frame subcomponent 1200 of the present disclosure.

In some examples, the leaflets 1210 are coupled to the leaflet frame subcomponent interior surface 1206 (e.g., to the leaflet frame interior surface 1206a). The leaflets 1210 may be coupled to the leaflet frame subcomponent 1200 in any of a variety of manners, including by wrapping one or more portions of the leaflets about one or more portions of the leaflet frame 1201, by suturing or sewing one or more portions to the leaflet frame 1201, but using adhesives or other mechanical fasteners, or by using one or more projections on the leaflet frame 1201 (not shown) that pass through one more apertures configured to be disposed about the one or more projections (not shown). Any of these coupling mechanisms, combinations thereof, and others may be employed as appropriate.

Interstage

Referring to FIG. 2A, the interstage 1300 includes a conduit 1302 that is coupled to an anchor frame subcomponent outlet end 1104 of the anchor frame subcomponent 1100 at an interstage first end 1314 and is coupled to a leaflet frame subcomponent inlet end 1202 at an interstage second end 1316. The conduit 1302 may comprise any suitable material known in the art that is flexible and is operable to be everted as discussed below. By way of example, the conduit 1302 may be a film or fabric, among other materials.

Figures 8A, 8B:
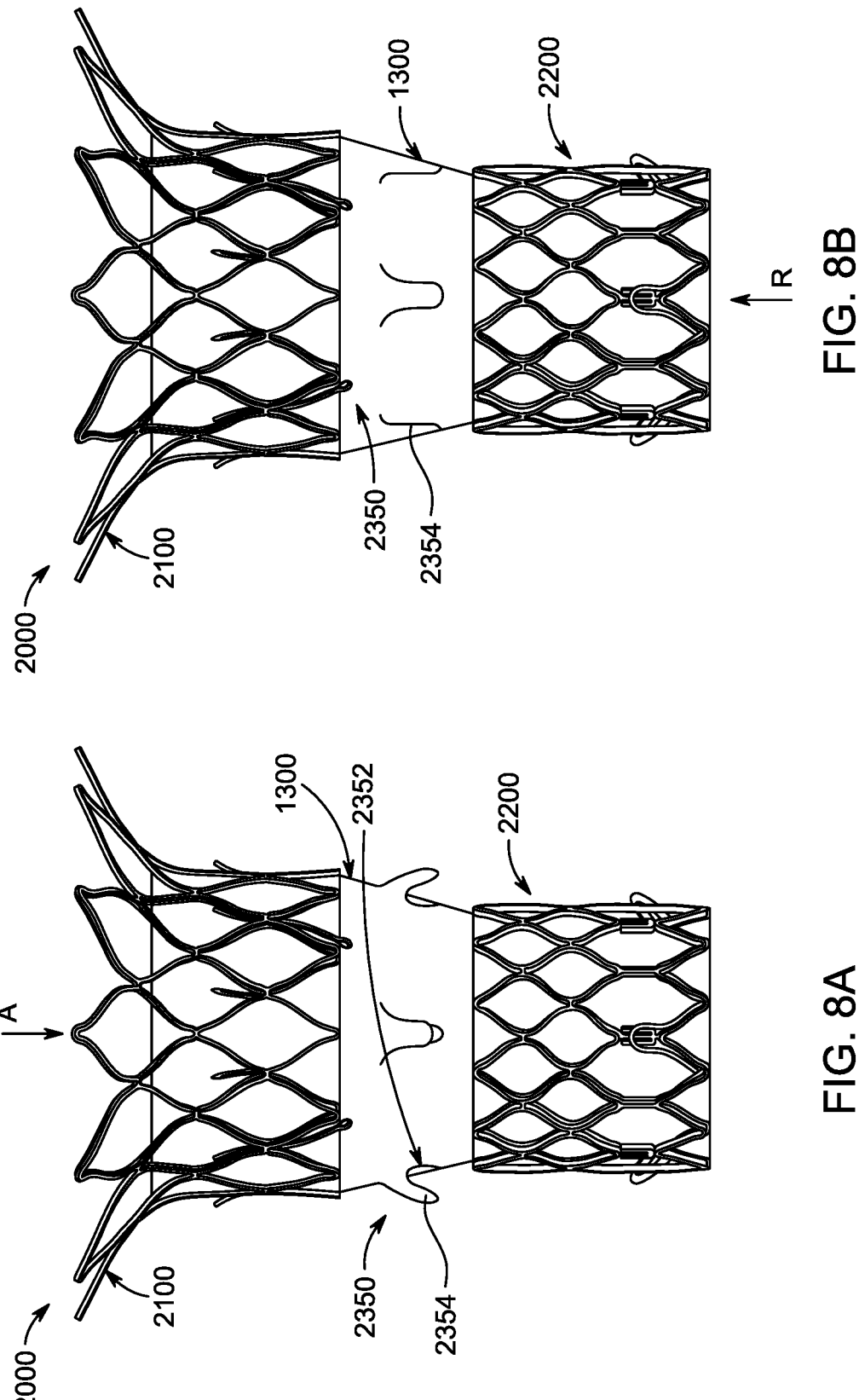
FIGS. 8A to 8C show various flow enabling features of a prosthetic valve in a delivery configuration, according to some embodiments.
Figure 8C:
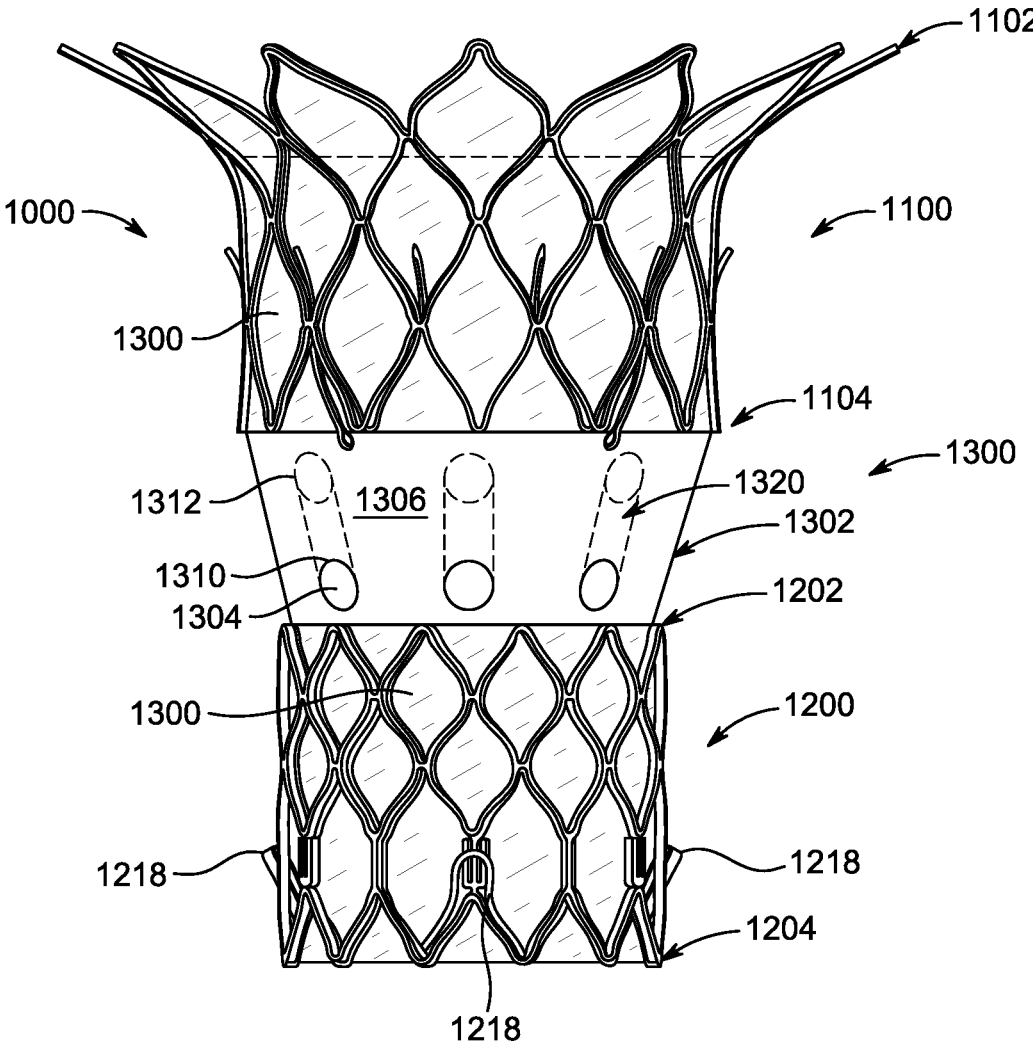

In various examples, the interstage 1300 further comprises one or more nesting retention elements 1330, such as shown in FIGS. 8C through 8E, to be described below, that is operable to retain the position of the leaflet frame subcomponent 1200 as nested in the anchor frame subcomponent 1100. For example, the leaflet frame subcomponent 1200 may be nested in the anchor frame subcomponent 1100 in a substantially fixed relationship during operation, or may be allowed to flex or displace in operation (e.g., axially and/or transversely), but to generally return to a neutral, desired position.

In accordance with some examples, the nesting retention elements 1330 may be one or more elongated elements that bias the interstage 1300 in the nested position, particularly after the leaflet frame subcomponent 1200 is expanded. For example, in FIG. 10E, the nesting retention elements 1330 may have a serpentine or sinuous configuration, whereas in FIG. 10F, the nesting retention elements 1330 may be straight and generally aligned with the longitudinal axis of the prosthetic valve 1000. In some examples, the nesting retention elements 1330 can be positioned between the locations of two neighboring ones of the inner apertures 1312 and/or between two neighboring ones of the outer apertures 1310 of the interstage 1300. In accordance with an embodiment, the nesting retention elements 1330 are caused to evert during the deployment process of translating the leaflet frame subcomponent 1200 as compressed into the anchor frame subcomponent 1100. The nesting retention elements 1330 are provided with a predetermined stiffness or other property sufficient to permit eversion during deployment when the leaflet frame subcomponent 1200 is compressed but not under normal biological forces when the leaflet frame subcomponent 1200 is expanded. In accordance with another embodiment, the nesting retention elements 1330 are sized such that, when the anchor frame subcomponent 1100 is expanded and the leaflet frame subcomponent is compressed, the nesting retention elements 1330 are able to rotate lengthwise from a forward-facing orientation to a backward facing orientation. When the leaflet frame subcomponent 1200 is expanded, the nesting retention elements 1330 have a profile or length that prevents the nesting retention elements 1330 from rotating or flipping back to a forward-facing orientation. In other words, the gap between the anchor frame subcomponent 1100 and the leaflet frame subcomponent 1200 which is nested therein is too narrow to allow end over end rotation of the nesting retention elements 1330. The nesting retention elements 1330 are provided with a predetermined stiffness or other property sufficient to prevent eversion of the nesting retention elements 1330 within the gap between the anchor frame subcomponent 1100 and the leaflet frame subcomponent 1200 under expected biological forces.

FIG. 1D is a perspective view showing the leaflet frame subcomponent 1200 and an anchor frame subcomponent 1100 of a prosthetic valve 1000 in a nested configuration, also referred to as the deployed position, leaflets not shown for clarity. FIG. 1B is a front view of the leaflet frame subcomponent 1200 and the anchor frame subcomponent 1100 of the prosthetic valve 1000 of FIG. 1D. In both FIGS. 1B and 1D, the leaflets and any film, as will be discussed below, are not shown for clarity. FIG. 1D is an axial view of the leaflet frame subcomponent 1200 and the anchor frame subcomponent 1100 of the prosthetic valve 1000 of FIG. 1A, showing the leaflets 1210. In the axial view of FIG. 1D, three leaflets 1210 are shown coupled to the leaflet frame subcomponent 1200. It is in this deployed position that the prosthetic valve 1000 remains in the native valve orifice to function as a prosthetic valve. The anchor frame subcomponent 1100 and the leaflet frame subcomponent 1200 are longitudinally offset and generally coaxial relative to one another.

With continued reference to FIGS. 1A to 1D, the prosthetic valve 1000 includes the anchor frame subcomponent 1100, and the leaflet frame subcomponent 1200. In the deployed configuration, the leaflet frame subcomponent 1200, which includes the leaflets 1210, is positioned at least partially within the anchor frame lumen 1113 (FIG. 1D) of the anchor frame subcomponent 1100. The prosthetic valve 1000 has a prosthetic valve inlet end (e.g., corresponding to anchor frame subcomponent inlet end 1102 and/or leaflet frame subcomponent inlet end 1202) and a prosthetic valve outlet end (e.g., corresponding to anchor frame subcomponent outlet end 1104 and/or leaflet frame subcomponent outlet end 1204). In various examples, when deployed within the body, the prosthetic valve inlet end (e.g., corresponding to anchor frame subcomponent inlet end 1102 and/or leaflet frame subcomponent inlet end 1202) is positioned upstream relative to the prosthetic valve outlet end, which is positioned downstream relative to the prosthetic valve inlet end (e.g., corresponding to anchor frame subcomponent inlet end 1102 and/or leaflet frame subcomponent inlet end 1202).

In various embodiments, the anchor frame subcomponent 1100 and the leaflet frame subcomponent 1200 are coupled together by the interstage 1300. Referring to FIG. 4, showing a side view of the prosthetic valve 1000 in a pre-deployed configuration on delivery device 1500, in some examples, the interstage 1300 is disposed between the anchor frame subcomponent 1100 and the leaflet frame subcomponent 1200 coupling them together. In some examples, the interstage 1300 includes a portion of a contiguous film that extends over a portion of the anchor frame subcomponent 1100 and the leaflet frame subcomponent 1200 operable to couple them together. In some examples, the contiguous film extends not only between but also over or within either or both of the anchor frame subcomponent 1100 and the leaflet frame subcomponent 1200. In some examples, the interstage 1300 is formed from a generally tubular material. In some examples, the interstage 1300 is formed by wrapping a film over and around a cylindrical mandrel, with either or both of the anchor frame 1101 and the leaflet frame 1201 being slid over and bonded thereto to the inner surface of the frames, with the film becoming an element of the anchor frame subcomponent 1100, the leaflet frame subcomponent 1200, and the interstage 1300, respectively. In some examples, the interstage 1300 is formed by wrapping the film over and around either or both of the anchor frame 1101 and the leaflet frame 1201 and the gap therebetween and bonded thereto to the outer surface of the frames, with the film becoming an element of the anchor frame subcomponent 1100, the leaflet frame subcomponent 1200, and the interstage 1300, respectively.

In examples where the anchor frame 1101 and the leaflet frame 1201 are comprised of metal, there is a metal to polymer to metal interconnection by way of the film, wherein there is no metal to metal contact between the two frames.

The interstage 1300 is generally any material that is biologically compatible and configured to couple to the anchor frame subcomponent 1100 and the leaflet frame subcomponent 1200. In various examples, the biocompatible material is a film that is not of a biological source and that is sufficiently flexible and strong for the particular purpose, such as a biocompatible polymer. In other examples the interstage 1300 may be of biological tissue, e.g. a dehydrated bovine tissue. In an embodiment, the film comprises a biocompatible polymer (e.g., ePTFE). In some examples, the film is a composite of two or more materials. The film may comprise one or more of a membrane, composite material, or laminate.

In various examples, a prosthetic valve and its associated delivery system are configured to facilitate continued valve functionality during the deployment procedure. In various examples, during a prosthetic valve deployment procedure to replace a damaged valve, the valve and valve orifice are temporarily obstructed by the prosthetic valve and the delivery device. In some instances, such obstructions occur prior to the prosthetic valve being deployed and becoming operational (e.g., prior to nesting the anchor frame subcomponent and the leaflet frame subcomponent). Accordingly, in various examples, the prosthetic valves of the present disclosure may additionally include one or more features that are configured to permit fluid to flow through or around the prosthetic valve during the implantation procedure, prior to the prosthetic valve becoming fully operational (e.g., prior to nesting the anchor frame subcomponent and the leaflet frame subcomponent).

Figures 9A, 9B:
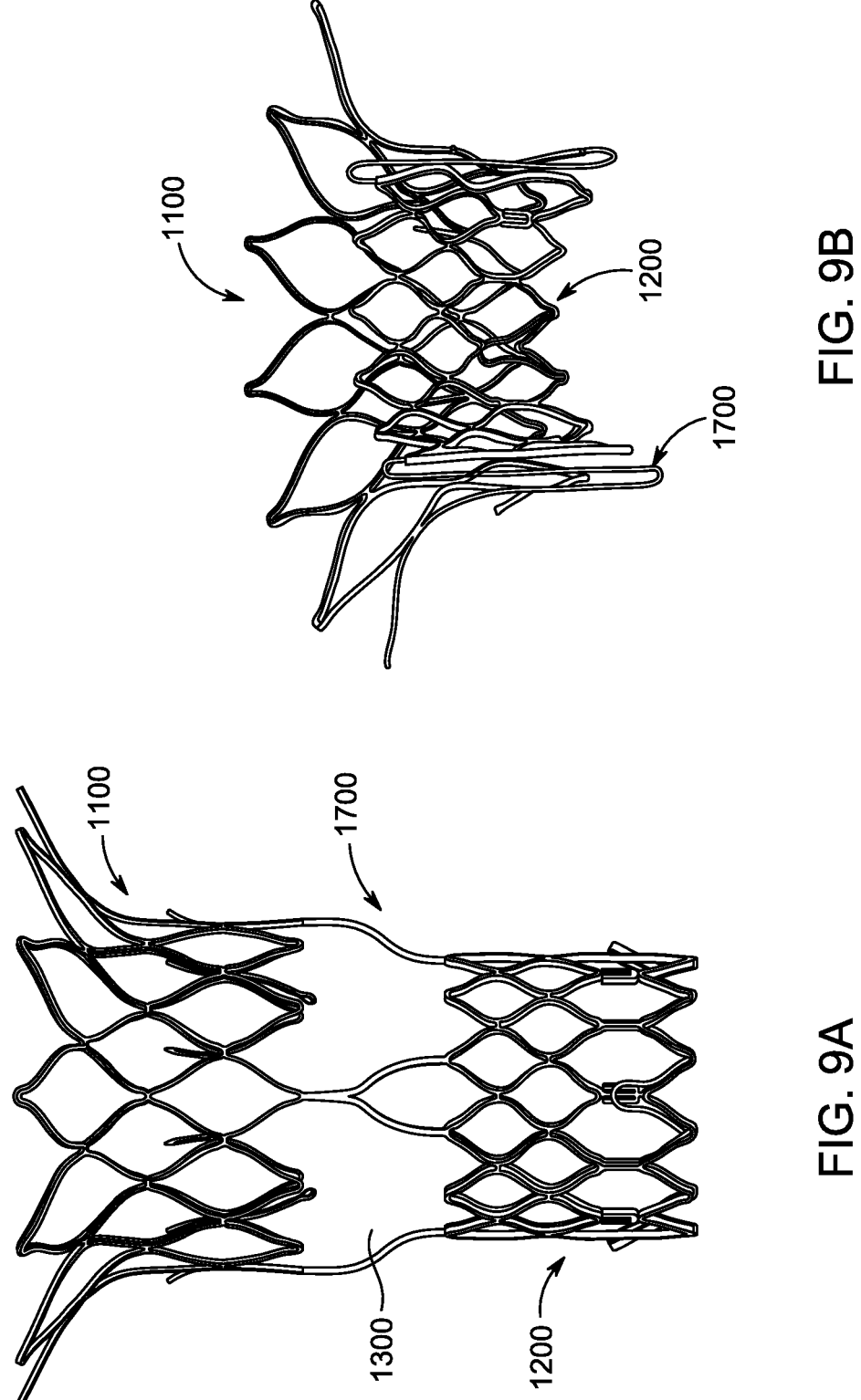
FIGS. 9A and 9B show connecting structures interconnecting an anchor frame subcomponent and a leaflet frame subcomponent of a prosthetic valve, according to some embodiments.

For example, and with reference to FIGS. 9A and 9B, the prosthetic valve 1000 includes one or more flow enabling features 1350 formed in the interstage 1300 extending between the anchor frame subcomponent 1100 and the leaflet frame subcomponent 1200. FIG. 9A is a side view of the prosthetic valve 2000 with the flow enabling features 1350 in an open configuration where antegrade flow (denoted by arrow "A") is permitted. FIG. 9B is a side view of the prosthetic valve 2000 with the flow enabling features 1350 in a closed configuration where retrograde (denoted by arrow "R") flow is obstructed. In some examples, the one or more flow enabling features 1350 include one or more perforations or apertures.

In some examples, the one or more flow enabling features 1350 additionally or alternatively include one or more mechanisms that facilitate unidirectional flow. For instance, in some examples, the flow enabling features are configured as one-way valves. In some examples, one-way valves include an aperture or perforation and a flap or element of material that overlays and is slightly larger than the aperture or perforation. In some examples, the one-way valve is oriented to permit antegrade flow through the prosthetic valve, while minimizing or preventing retrograde flow through the prosthetic valve.

Figures 9C, 9D:
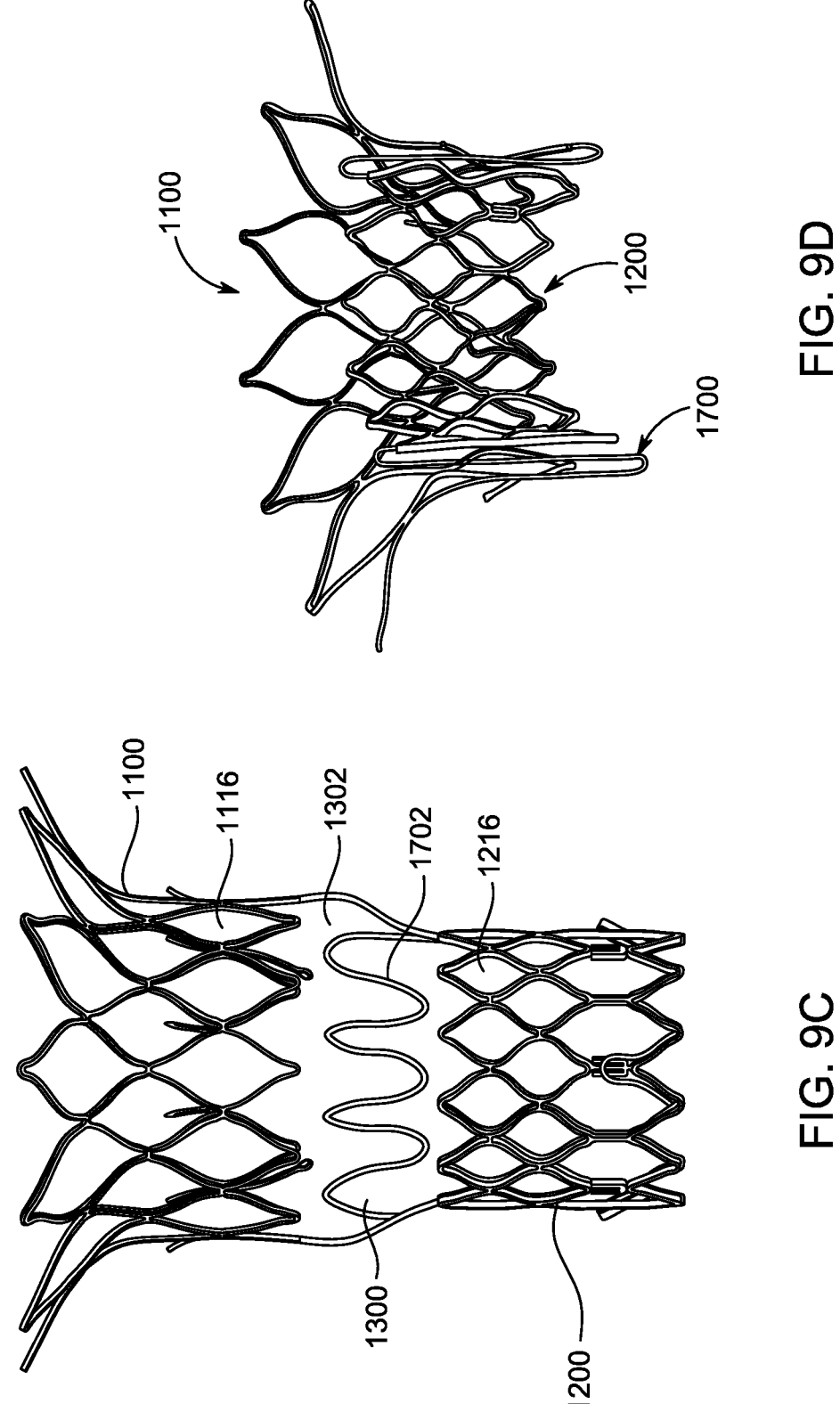
FIGS. 9C and 9D show nesting retention elements in the form of continuous sinuous elements, according to some embodiments.

As shown in FIGS. 9A and 9B, the flow enabling features 1350 include an aperture 1352 and a flap 1354 that operate to facilitate antegrade flow through the prosthetic valve 2000 prior to the anchor frame subcomponent 1100 and the leaflet frame subcomponent 1200 being nested together (i.e., while the anchor frame subcomponent 1100 and the leaflet frame subcomponent 1200 are longitudinally offset as illustrated and described herein). The flap 1354 is oversized relative to the aperture 1352 to restrict or minimize retrograde flow through the one or more flow enabling features 1350 while permitting antegrade flow FIG. 9C is another embodiment of the interstage 1300 as shown coupled to the leaflet frame subcomponent 1200 and anchor frame subcomponent 1100. In accordance with this embodiment, the conduit 1302 of the interstage 1300 includes a double layer construct, including an inner layer 1304 that defines an inner surface of the interstage 1300 and an outer layer 1306 that defines an outer surface of the interstage 1300 as viewed in the partially deployed position. The inner layer 1304 and the outer layer 1306 are coupled together at least at the leaflet frame subcomponent inlet end 1202 of the leaflet frame subcomponent 1200 and the anchor frame subcomponent outlet end 1104 of the anchor frame subcomponent 1100. The inner layer 1304 defines one or more inner apertures 1312 therethrough adjacent the anchor frame subcomponent 1100 and the outer layer 1306 defines one or more outer apertures 1310 therethrough adjacent the leaflet frame subcomponent 1200. The inner layer 1304 and the outer layer 1306 are not coupled at least between one of the inner apertures 1312 and one of the outer apertures 1310 so as to define a flow space 1320 therebetween.

In some examples, the prosthetic valve 1000 additionally or alternatively includes one or more features that extend between the anchor frame subcomponent 1100 and the leaflet frame subcomponent 1200. For example, as shown in FIGS. 10A and 10B, the prosthetic valve 1000 includes a plurality of interconnecting struts 1700 that extend between the anchor frame subcomponent 1100 and the leaflet frame subcomponent 1200. FIG. 10A shows the prosthetic valve 1000 prior to telescoping or nesting of the anchor frame subcomponent 1100 and the leaflet frame subcomponent 1200. FIG. 10B shows the prosthetic valve 1000 with the anchor frame subcomponent 1100 and the leaflet frame subcomponent 1200 in a nested configuration.

As shown in FIGS. 10A and 10B, the interconnecting struts 1700 are configured to evert along with the interstage 1300 as the leaflet frame subcomponent 1200 is telescoped or nested with the anchor frame subcomponent 1100. In various examples, the interconnecting struts 1700 are elongate elements 1704 that are curved or s-shaped. It will be appreciated that such a configuration provides that the interconnecting struts 1700 can be temporarily bent or folded upon themselves as the anchor frame subcomponent 1100 and the leaflet frame subcomponent 1200 are nested.

The interconnecting struts 1700 provide stiffening bias such that it takes a predetermined amount of force to nest the leaflet frame subcomponent 1200 into the anchor frame subcomponent 1100 and a corresponding predetermined amount of force to resist the movement of the leaflet frame subcomponent 1200 from the nested position, especially considering an interstage 1300 that does not provide sufficient resistance from movement of the leaflet frame subcomponent 1200 from the nested position. The interconnecting struts 1700 also provides a predetermined amount of lateral and radial stiffness to facilitate handling and deployment dynamics, especially considering an interstage 1300 that does not provide sufficient stiffness to facilitate from handling and deployment dynamics. In various examples, the interstage 1300 is very thin and thus provides little to no radial or lateral stiffness to resist the movement of the leaflet frame subcomponent 1200 from the nested position and/or to facilitate handling and deployment dynamics. In accordance with various examples, the interconnecting struts 1700 may be coupled to the interstage 1300, either on an inner surface, an outer surface or, in the examples having interstage 1300 that has a conduit 1302 including a double layer construct, contained between the inner layer 1304 and the outer layer 1306.

In various examples, the interconnecting struts 1700 as everted operate to maintain the nested configuration of the anchor frame subcomponent 1100 and the leaflet frame subcomponent 1200. In some examples, with the anchor frame subcomponent 1100 and the leaflet frame subcomponent 1200 in the nested configuration and the interconnecting struts 1700 everted, a column strength of the interconnecting struts 1700 operates to resist compressive loads that would otherwise cause the leaflet frame subcomponent 1200 to de-nest or telescope out of and away from the anchor frame subcomponent 1100.

In accordance with other examples, as shown in FIGS. 10C through 10E, the prosthetic valve 1000 includes one or more nesting retention elements 1330 in the form of a sinuous element 1702 (e.g., a continuously extending sinuous member) that extends between the anchor frame subcomponent 1100 and the leaflet frame subcomponent 1200 but does not couple directly therewith. The sinuous element 1702 provides stiffening bias to the interstage 1300. FIG. 10C shows the prosthetic valve 1000 prior to telescoping or nesting of the anchor frame subcomponent 1100 and the leaflet frame subcomponent 1200.

FIG. 10D shows the prosthetic valve 1000 with the anchor frame subcomponent 1100 and the leaflet frame subcomponent 1200 in a nested configuration. As shown in FIGS. 10C and 10D, the sinuous element 1702 is configured to evert along with the interstage 1300 as the leaflet frame subcomponent 1200 is telescoped or nested with the anchor frame subcomponent 1100. In various examples, the sinuous element 1702 is an elongate element that is curved or s-shaped. It will be appreciated that such a configuration provides that the sinuous element 1702 can be temporarily elastically bent or folded upon itself as the anchor frame subcomponent 1100 and the leaflet frame subcomponent 1200 are nested. The sinuous element 1702 provides stiffening bias such that it takes a predetermined amount of force to nest the leaflet frame subcomponent 1200 into the anchor frame subcomponent 1100 and a corresponding predetermined amount of force to resist the movement of the leaflet frame subcomponent 1200 from the nested position, especially considering an interstage 1300 that does not provide sufficient resistance from movement of the leaflet frame subcomponent 1200 from the nested position.

The sinuous element 1702 also provides a predetermined amount of lateral and radial stiffness to facilitate handling and deployment dynamics, especially considering an interstage 1300 that does not provide sufficient stiffness to facilitate from handling and deployment dynamics. In various examples, the interstage 1300 is very thin and thus provides little to no radial or lateral stiffness to resist the movement of the leaflet frame subcomponent 1200 from the nested position and/or to facilitate handling and deployment dynamics. In accordance with various examples, the sinuous element 1702 may be coupled to the interstage 1300, either on an inner surface, an outer surface or, in the examples having an interstage 1300 with a conduit 1302 that is defined by a double layer (e.g., a double layer of film), the sinuous element 1702 may be contained between the inner layer 1304 and the outer layer 1306.

In various examples, the sinuous element 1702 as everted operates to maintain the nested configuration of the anchor frame subcomponent 1100 and the leaflet frame subcomponent 1200. In some examples, with the anchor frame subcomponent 1100 and the leaflet frame subcomponent 1200 in the nested configuration, a column strength of the sinuous element 1702 operates to resist compressive loads that would otherwise cause the leaflet frame subcomponent 1200 to de-nest or telescope out of and away from the anchor frame subcomponent 1100.

As explained, the nesting retention elements 1330 may be operable to retain the leaflet frame subcomponent 1200 as nested in the anchor frame subcomponent 1100. Examples of nesting retention elements 1330 are provided below. In accordance with some examples, the nesting retention elements 1330 may be elongated elements that bias the interstage 1300 in the nested position. In accordance with an embodiment, the nesting retention elements 1330 are caused to evert during the deployment process of translating the leaflet frame subcomponent 1200 into the anchor frame subcomponent 1100. The nesting retention elements 1330 are provided with a predetermined stiffness or other property sufficient to permit eversion during deployment but not under normal biological forces.

In accordance with another embodiment, the nesting retention elements 1330 are sized such that, when the anchor frame subcomponent 1100 is expanded and the leaflet frame subcomponent is compressed, the nesting retention elements 1330 are able to rotate lengthwise from a forward-facing orientation to a backward facing orientation. When the leaflet frame subcomponent 1200 is expanded, the nesting retention elements 1330 have a profile or length that prevents the nesting retention elements 1330 from rotating or flipping back to a forward-facing orientation. In other words, the gap between the anchor frame subcomponent 1100 and the leaflet frame subcomponent 1200 is too narrow to allow end over end rotation of the nesting retention elements 1330. The nesting retention elements 1330 are provided with a predetermined stiffness or other property sufficient to prevent eversion of the nesting retention elements 1330 within the gap between the anchor frame subcomponent 1100 and the leaflet frame subcomponent 1200 under normal biological forces.

Anchor Frame Subcomponent

Figure 4A:
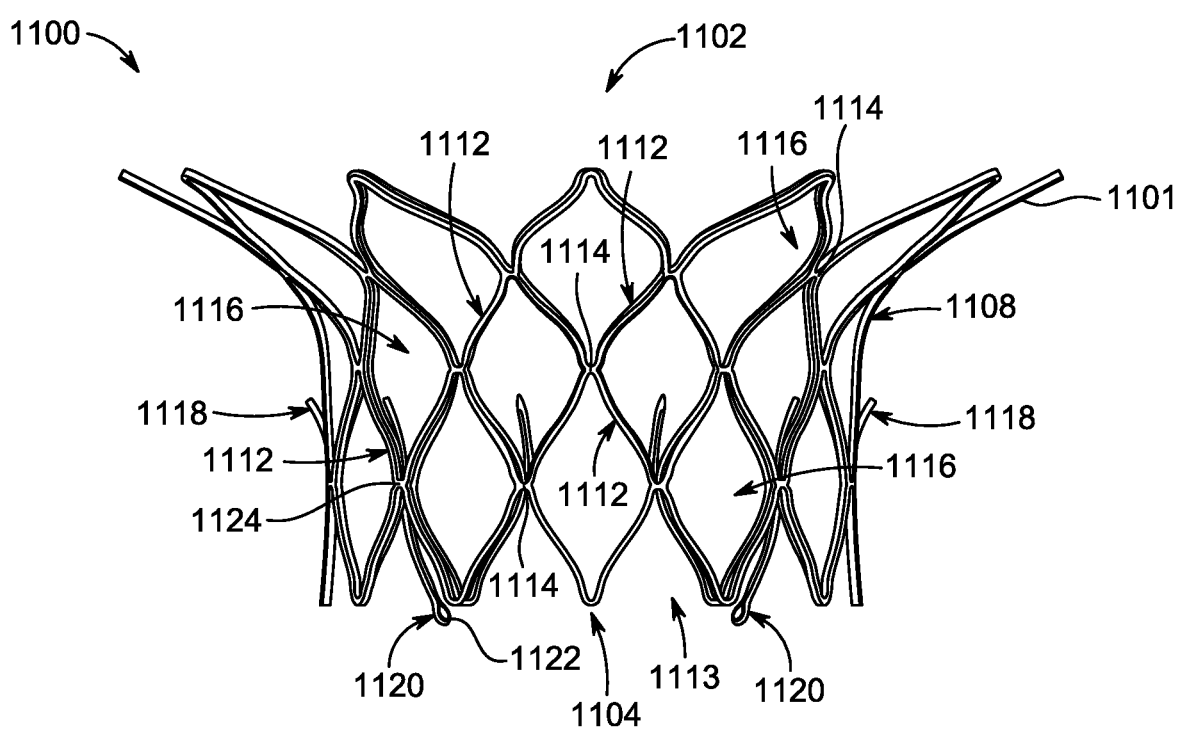
FIG. 4A is a side view of an anchor frame subcomponent, according to some embodiments.
Figure 4B:
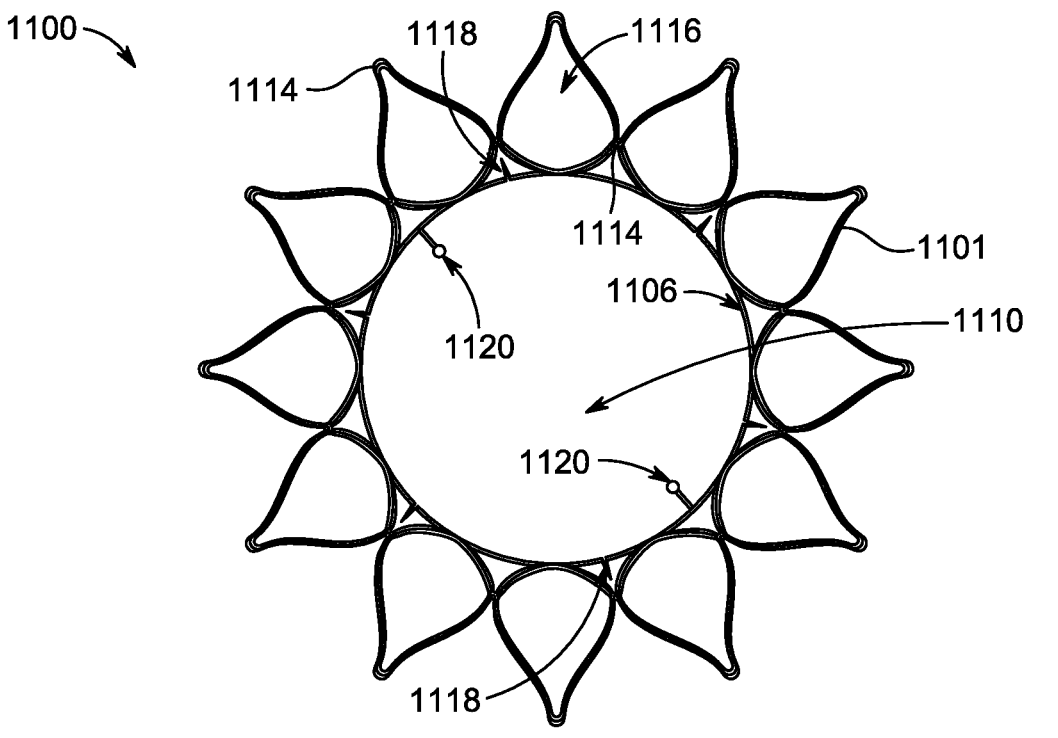
FIG. 4B is an axial view of an anchor frame subcomponent, according to some embodiments.

FIG. 4A is a side view of the anchor frame subcomponent 1100 and FIG. 4B is an axial view of the anchor frame subcomponent 1100. The anchor frame subcomponent 1100 includes an anchor frame 1101. The anchor frame 1101 is a tubular member defining an anchor frame lumen 1113 operable to receive the leaflet frame subcomponent 1200 therein. The side of the anchor frame 1101 may be at least partially covered, such as with a film or fabric, not shown for clarity, suitable for a particular purpose, such as, but not limited to, restrict fluid from passing through the anchor frame 1101, or encourage tissue ingrowth at the implant site. For illustrative purposes, the following examples are suitable especially for a transcatheter application, but are also suitable for a surgical application.

In various examples, the construction of and materials used in the film are such that the anchor frame subcomponent 1100 promotes cellular ingrowth, adhesion, and/or attachment. That is, in various examples, the anchor frame subcomponent 1100 is constructed in a manner that promotes the ingrowth of tissue into one or more portions of the film. It will be appreciated that cellular ingrowth further increases sealing of the prosthetic valve with the native valve orifice and helps minimize para-valvular leakage, that is, leakage between the prosthetic valve and the tissue into which it is coupled.

In accordance with some embodiments, the anchor frame subcomponent 1100 (e.g., the anchor frame 1101) is formed of or otherwise includes a shape memory material operable to flex under load and retain its original shape when the load is removed, thus allowing the anchor frame subcomponent 1100 to self-expand from a compressed shape to a predetermined larger shape. The anchor frame subcomponent 1100 may comprise the same or different materials as the leaflet frame subcomponent 1200. In accordance with an embodiment, the anchor frame subcomponent 1100 is plastically deformable to be expanded by a balloon. In another embodiment the anchor frame subcomponent 1100 is elastically deformable so as to be self-expanding.

FIGS. 4A and 4B are side and axial views, respectively, of the anchor frame subcomponent 1100, in accordance with an embodiment. The anchor frame subcomponent 1100 is a generally tubular member having an anchor frame subcomponent inlet end 1102, an anchor frame subcomponent outlet end 1104, an anchor frame subcomponent interior surface 1106, and an anchor frame subcomponent exterior surface 1108. In various examples, the anchor frame subcomponent 1100 defines an anchor frame subcomponent interior region

1110 (e.g., an anchor frame subcomponent lumen). For example, the anchor frame subcomponent interior region 1110 is a generally cylindrical void defined between the anchor frame subcomponent inlet end 1102 and the anchor frame subcomponent outlet end 1104, and the anchor frame subcomponent interior surface 1106 of the anchor frame subcomponent 1100. However, in-situ, the anchor frame subcomponent interior region 1110 may adopt an irregular cross section, depending on the geometry of the native valve orifice. In various examples, the anchor frame subcomponent 1100 is configured to couple to a native valve orifice. Accordingly, in various examples, a diameter of the anchor frame subcomponent 1100 (e.g., a diameter of an interior or exterior surface of the anchor frame subcomponent 1100) is sized in accordance with patient anatomy. It will be appreciated that nonlimiting examples of anchor frame subcomponent 1100 can be provided with a diameter (e.g., a diameter of an interior or exterior surface of the anchor frame subcomponent 1100) in a range of between twenty-five (25) millimeters and fifty (50) millimeters, depending on a patient's anatomy. However, examples of the anchor frame subcomponent 1100 having diameters (e.g., a diameter of an interior or exterior surface of the anchor frame subcomponent 1100) in excess of fifty (50) millimeters are also envisioned and fall within the scope of the present disclosure, depending on patient anatomy.

In some embodiments, the anchor frame subcomponent 1100 defines a flange or a flared portion at the anchor frame subcomponent inlet end 1102 that flares or tapers radially outward when in the deployed configuration. For example, as shown in at least FIGS. 1B, 2A, 5B, 5C, and 5E, the anchor frame subcomponent inlet end 1102 is flared or otherwise tapered radially outward when in the deployed configuration. That is, as shown, the anchor frame subcomponent inlet end 1102 of the anchor frame subcomponent 1100 has a larger deployed (e.g. relaxed) diameter than does the anchor frame subcomponent outlet end 1104 of the anchor frame subcomponent 1100. In various examples, as discussed in greater detail below, such a configuration operates to minimize migration risks and helps facilitate abutment of the anchor frame subcomponent 1100 with tissue at the treatment site.

In some embodiments, the anchor frame subcomponent 1100 defines a cylindrical or tubular mesh or crossing-pattern forming a framework defining apertures. For example, as shown, the anchor frame subcomponent 1100 includes a plurality of frame members 1112 that are interconnected and arranged in one or more patterns. In some examples, these patterns repeat one or more times. In some such examples, the frame members 1112 are arranged and interconnected such that the anchor frame subcomponent 1100 includes a plurality of patterned rows. In various examples, the frame members 1112 are connected to one another at joints 1114. In some examples, these joints 1114 operate as flex points so as to provide a preferential flexing location for the anchor frame subcomponent 1100 to flex when compressed to a smaller delivery diameter and when forces from the surrounding anatomy act to compress the anchor frame subcomponent 1100 during normal operation after delivery and deployment of the prosthetic valve 1000. In some examples, the flex point or joints 1114 comprises a site on the anchor frame subcomponent 1100 that undergoes a high degree of bending. In some examples, the joints 1114 may comprise a geometry, structural modification or material modification, among others, that biases the anchor frame subcomponent 1100 to bend at the flex points or joints 1114 when compressed.

In some embodiments, one or more apertures 1116 are defined between the joints 1114 and the frame members 1112 that are interconnected of the anchor frame subcomponent 1100. In some examples, these apertures 1116 extend between the anchor frame subcomponent exterior surface 1108 and the anchor frame subcomponent interior surface 1106 of the anchor frame subcomponent 1100. As illustrated in the embodiments of FIGS. 2A and 2B, one or more of the apertures 1116 define a diamond shape when the anchor frame subcomponent 1100 is in a deployed configuration. Upon compression to a smaller diameter (e.g., a delivery diameter), one or more of the joints 1114 and the frame members 1112 deform such that the apertures 1116 generally define an elongated diamond shape (e.g., as shown generally in FIG. 4). Upon re-expanding the anchor frame subcomponent 1100 to a larger diameter during deployment at a treatment site, the apertures 1116 re-expand to define the generally wider diamond shape. The anchor frame subcomponent 1100 is optionally coupled to the cutting element 1001 via the one or more of the apertures 116, as referenced above.

It should be appreciated that while the frame members 1112 illustrated and described herein are interconnected and define apertures 1116 having generally a diamond shape, the frame members 1112 that are interconnected with one another may be arranged in a number of alternative patterns. For example, a framework of the anchor frame subcomponent 1100 can define any number of features, repeatable or otherwise, such as geometric shapes and/or linear or meandering series of sinusoids. Geometric shapes can comprise any shape that facilitates circumferential compressibility and expandability of the anchor frame subcomponent 1100. That is, a number of alternative patterns are envisioned where the arrangement of frame members 1112 is configured in such a manner as to provide for an anchor frame subcomponent 1100 that can be compressed to a smaller diameter for transcatheter delivery and subsequently expanded (or allowed to expand) to a larger diameter at a treatment site during deployment of the prosthetic valve 1000. Accordingly, the disclosure should not be read as being limited to arrangements of the frame members 1112 that define apertures 1116 that are diamond-shaped.

In various embodiments, the anchor frame subcomponent 1100 may comprise or otherwise be formed from a cut tube, or any other element suitable for the particular purpose of the anchor frame subcomponent 1100 as described herein. In some examples, the anchor frame subcomponent 1100 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter as illustrated and described herein.

The anchor frame subcomponent 1100 can comprise any metallic or polymeric biocompatible material. For example, the anchor frame subcomponent 1100 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

In various examples, the anchor frame subcomponent 1100 is elastically deformable so as to be self-expanding under spring loads, as those of skill will appreciate. In some examples, the anchor frame subcomponent 1100 is plastically deformable so as to be mechanically expanded such as with a balloon, as those of skill will appreciate. In yet some other examples, the anchor frame subcomponent 1100 is plastically deformable as well as elastically deformable. That is, in some examples, the anchor frame subcomponent 1100 includes one or more elastically deformable components or features and one or more plastically deformable components or features. Thus, it should be appreciated that the examples of the anchor frame subcomponent 1100 presented herein are not to be limited to a specific design or mode of expansion.

Subcomponent Assembly

In various embodiments, the leaflet frame subcomponent 1200 is nestable within the anchor frame subcomponent interior region 1110 (e.g., the anchor frame lumen 1113) of the anchor frame subcomponent 1100. In particular, as shown, the anchor frame subcomponent 1100 and the leaflet frame subcomponent 1200 are sized and shaped in a manner that provides for the leaflet frame subcomponent 1200 being coaxially disposable or receivable at least partially within the anchor frame subcomponent 1100. Thus, in various examples, the anchor frame subcomponent 1100 is configured such that a portion of (or alternatively all of) the leaflet frame subcomponent 1200 can be received by or otherwise positioned within the anchor frame lumen 1113 defined by the anchor frame subcomponent 1100.

In some examples, the leaflet frame subcomponent 1200 is sized such that a diameter of the exterior surface of the leaflet frame subcomponent 1200 is less than a diameter of the interior surface of the anchor frame subcomponent 1100 that defines the anchor frame lumen 1113. In some examples, a diameter of the exterior surface of the leaflet frame subcomponent 1200 is in a range of between seventy five percent (75%) and ninety percent (90%) of a diameter of the interior surface of the anchor frame subcomponent 1100. In some examples, a diameter of the exterior surface of the leaflet frame subcomponent 1200 is seventy five percent (75%) or less than a diameter of the interior surface of the anchor frame subcomponent 1100. In various examples, such configurations also provide that the leaflet frame subcomponent 1200 can be received within the anchor frame subcomponent 1100. In various examples, such configurations provide that the anchor frame subcomponent 1100 can deform, such as, but not limited to being out of round or generally oval-shaped, to accommodate or otherwise conform to the native valve orifice without causing a deformation of the leaflet frame subcomponent 1200.

Thus, in some examples, the prosthetic valve 1000 provides a leaflet frame subcomponent 1200 that essentially floats within the anchor frame subcomponent 1100 by way of the interstage 1300 and does not directly couple with a native valve orifice. The anchor frame subcomponent 1100 may conform to the shape of the native valve orifice whereas the leaflet frame subcomponent 1200 does not conform to the shape of the native valve orifice. The leaflet frame subcomponent 1200 remains tubular or at a preferred geometrical configuration so as to present the leaflets 1210 with a geometrically stable platform ensuring proper leaflet function, including coaptation and opening dynamics. It is appreciated that these benefits associated with the leaflet frame subcomponent 1200 not needing to conform to the native valve orifice may be realized in either transcatheter or surgical placement of the prosthetic valve 1000.

In various embodiments, the prosthetic valve 1000 is configured such that the anchor frame subcomponent 1100 and the leaflet frame subcomponent 1200 can be nested in-situ after the anchor frame subcomponent 1100 and the leaflet frame subcomponent 1200 are deployed at a treatment site in a patient's anatomy. That is, in various embodiments, the prosthetic valve 1000 can be delivered to a treatment region within a patient's anatomy with the anchor frame subcomponent 1100 and the leaflet frame subcomponent 1200 longitudinally offset relative to one another and subsequently nested with one another at the treatment site. In various embodiments, the prosthetic valve 1000 is loaded onto delivery device 1500 with the anchor frame subcomponent 1100 and the leaflet frame subcomponent 1200 longitudinally offset relative to one another which presents a lower profile or diameter than if the prosthetic valve 1000 were to be loaded onto the delivery device in the nested configuration. A lower delivery profile of a transcatheter delivered prosthetic valve has well recognized advantages, including easier advancement though vessels.

It is appreciated that these benefits associated with the leaflet frame subcomponent 1200 not being nested into the anchor frame subcomponent 1100 during implantation may also be realized in surgical placement of the prosthetic valve 1000. By way of example, but not limited thereto, the anchor frame subcomponent 1100 may be more easily sutured into the native valve orifice without the leaflet frame subcomponent 1200 being within the anchor frame subcomponent 1100 and in close proximity to the suturing procedure lessening the chance of needle damage to the leaflets.

In some embodiments, the anchor frame subcomponent 1100 and the leaflet frame subcomponent 1200 are operable to nest with one another by telescoping the anchor frame subcomponent 1100 and the leaflet frame subcomponent 1200 relative to one another in-situ. Thus, in various examples, the leaflet frame subcomponent 1200 and the anchor frame subcomponent 1100 are sized such that the leaflet frame subcomponent 1200 can be receive within anchor frame subcomponent interior region 1110 (FIG. 4B).

In various embodiments, in addition to or alternative to telescoping relative to one another, the anchor frame subcomponent 1100, the leaflet frame subcomponent 1200, and the interstage 1300 are each configured to be compressed or collapsed to a delivery profile and then re-expanded in-situ to provide for transcatheter delivery of the prosthetic valve 1000, as discussed in greater detail below.

Tissue Engagement Features

In various embodiments, the anchor frame subcomponent 1100 is configured to provide positive engagement with an implant site to firmly anchor the prosthetic valve 1000 to the treatment site. For instance, in various examples, the anchor frame subcomponent 1100 includes one or more tissue engagement features 1118 that are configured to engage one or more regions of tissue at the native valve orifice adjacent the prosthetic valve 1000. In various examples, the tissue engagement features 1118 comprise one or more tissue anchors (e.g., barbs).

In various examples, the one or more tissue engagement features 1118 project away from the anchor frame subcomponent interior surface 1106 and/or the anchor frame subcomponent exterior surface 1108, radially outward from a longitudinal axis of the anchor frame subcomponent 1100, and toward the tissue adjacent to the prosthetic valve 1000. Generally, the tissue engagement features 1118 may be operable to project away from the anchor frame subcomponent 1100 when the anchor frame subcomponent 1100 is deployed (e.g., when a constraining member is withdrawn or otherwise removed). Although, in some examples, the tissue engagement features 1118 may be independently deployable. In some examples, with the anchor frame subcomponent 1100 in the deployed configuration, the tissue engagement features 1118 are operable to engage the tissue proximate the anchor frame subcomponent 1100 such that the tissue engagement features 1118 secure the anchor frame subcomponent 1100 to the adjacent tissue, as will be discussed in greater detail below.

In some examples, in a deployed configuration, the tissue engagement features project away from an exterior surface of the anchor frame subcomponent in a range of between thirty (30) and sixty (60) degrees. In some such examples, the tissue engagement features project away from an exterior surface, or offset from the exterior surface, of the anchor frame subcomponent at an angle of forty-five (45) degrees, though other configurations are contemplated and fall within the scope of the present application, including any approximate value of the foregoing values. Generally, any angle of projection is suitable provided that the tissue engagement features operate for their intended purpose of engaging the tissue adjacent to the anchor frame subcomponent and causing the anchor frame subcomponent to be secured to the tissue. Though the tissue engagement features may include a variety of different lengths (depending on the angle from which they project from the anchor frame subcomponent), it will be appreciated that the tissue engagement features are of a length suitable for engaging tissue and securing the anchor frame subcomponent to the adjacent tissue, but not so long as to risk detrimental damage to the native valve orifice. One nonlimiting example configuration includes tissue engagement features projecting from the anchor frame subcomponent in a range of between thirty (30) and sixty (60) degrees and having a length of between fifty (50) micron and two hundred (200) micron.

Generally, the tissue engagement features 1118 are positioned along the anchor frame subcomponent such that they are operable to engage tissue proximate the anchor frame subcomponent 1100 when the anchor frame subcomponent 1100 is expanded in-situ. The tissue engagement features 1118 may be arranged in one or more rows along a longitudinal axis of the anchor frame subcomponent 1100. That is, in various examples, anchor frame subcomponent may include a first set (or row) of anchors and a second set (or row) of anchors longitudinally offset relative to the first set of anchors. In one such example, the first set of anchors is more proximate the anchor frame subcomponent outlet end 1104 of the anchor frame subcomponent 1100 than is the second set of anchors.

In various embodiments, the one or more tissue engagement features 1118 are circumferentially arranged about the anchor frame subcomponent 1100. In some examples, the one or more tissue engagement features 1118 are evenly dispersed about the circumference of the anchor frame subcomponent. For example, the tissue engagement features 1118 are dispersed about the frame and are offset from one another by ninety (90) degrees depending on the number of anchors. Alternatively, the tissue engagement features 1118 may be dispersed about the frame and offset from one another by sixty (60) degrees depending on the number of anchors. Generally, the angular offset between the anchors is a function of the number of anchors dispersed about the anchor frame subcomponent 1100, as those of skill will appreciate. In some examples, the angular offset between the anchors is additionally or alternatively based on an arrangement or pattern of the frame members 1112.

In various examples, while the tissue engagement features 1118 project away from the anchor frame subcomponent 1100 when the anchor frame subcomponent 1100 is in the deployed configuration, the tissue engagement features 1118 are stowed or do not otherwise project away from the anchor frame subcomponent 1100 when the anchor frame subcomponent 1100 is compressed in the delivery configuration. Thus, in various examples, the tissue engagement features 1118 are stowable during delivery and are configured to transition to a deployed configuration where they project away from the anchor frame subcomponent 1100. In some examples, a constraining member disposed about the anchor frame subcomponent 1100 during delivery facilitates stowing of the tissue engagement features 1118. In some examples, the tissue engagement features 1118 are stowed in one or more of the apertures 1116 of the anchor frame subcomponent 1100.

In various embodiments, the tissue engagement features 1118 are integral to the anchor frame subcomponent 1100. For example, one or more of the tissue engagement features 1118 are formed in conjunction with and from the same material as the frame members 1112. In other examples, one or more of the tissue engagement features 1118 are separate components additionally or alternatively coupled or attached to the anchor frame subcomponent 1100. For instance, some non-limiting examples include crimping and/or welding one or more tissue engagement features to the anchor frame subcomponent 1100.

Figure 4C:
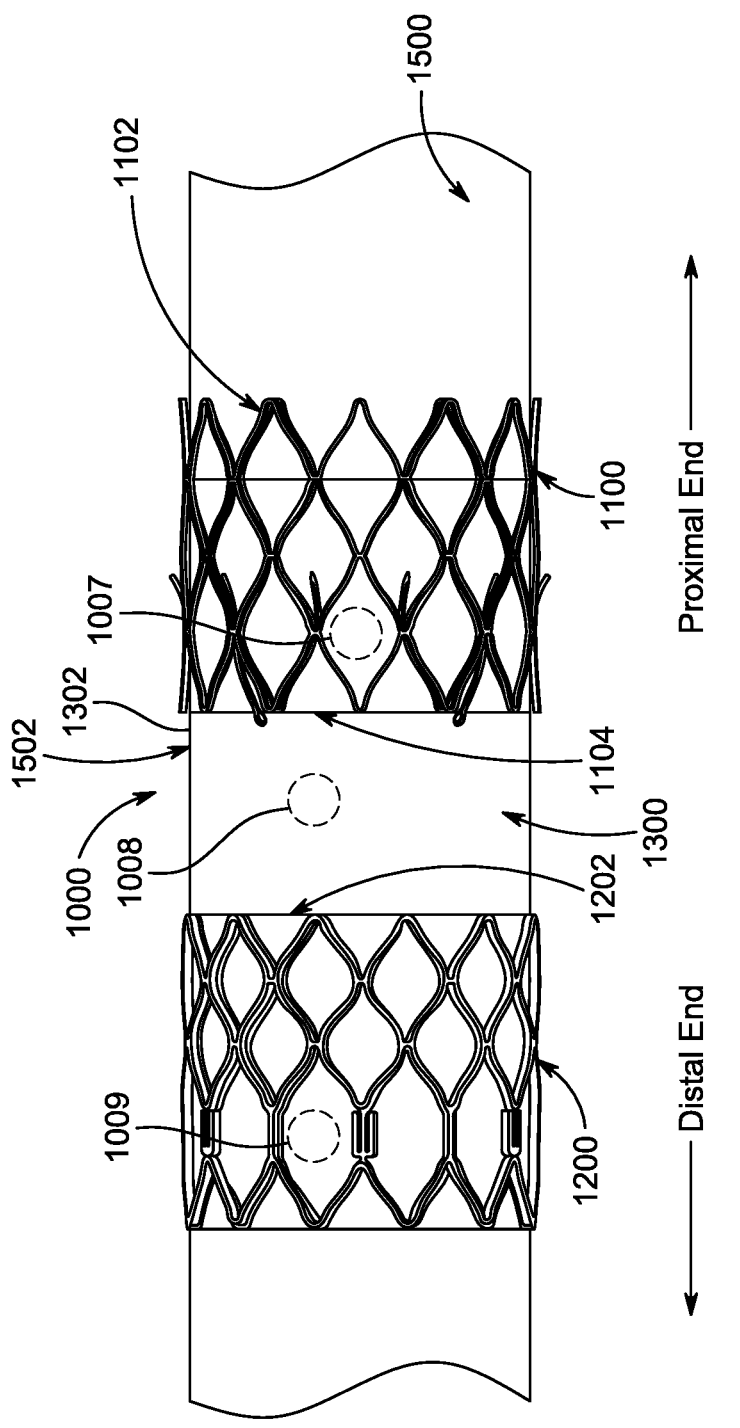
FIG. 4C is an illustration of a delivery device and prosthetic valve coupled to the delivery device, according to some embodiments.

Likewise, while the anchor frame subcomponent inlet end 1102 of the anchor frame subcomponent 1100 tapers or flares radially outward in a deployed configuration in certain examples, the flared or tapered portion of the anchor frame subcomponent 1100 is configured to deflect when the anchor frame subcomponent 1100 is in the delivery configuration. For example, as shown in FIG. 4C, the anchor frame subcomponent inlet end 1102 of the anchor frame subcomponent 1100 is deflected such that the anchor frame subcomponent 1100 has a substantially uniform delivery profile along its longitudinal axis.

In various examples, one or more constraining members (not shown) are formed as a filament or other material that can be looped or extended around various features and placed under tension to maintain those features in a compact, or delivery configuration In some example, the one or more constraining members generally define a loop and are disposed about the anchor frame subcomponent 1100 in the delivery configuration. For example, a first constraining member is disposed near the anchor frame subcomponent inlet end 1102 of the anchor frame subcomponent 1100 and a second constraining member is disposed near the anchor frame subcomponent outlet end 1104 of the anchor frame subcomponent 1100. Each constraining member may extend about an anchor frame subcomponent exterior surface 1108 of the anchor frame subcomponent 1100, or one or more of the constraining members may be woven through one or more portions of the film disposed about the anchor frame subcomponent 1100. That is, in some examples, one or more of the constraining members extending adjacent the anchor frame subcomponent exterior surface 1108 (e.g., exterior of the anchor frame subcomponent exterior surface) may extend through a portion of the film, and extend along a portion of the anchor frame subcomponent interior surface 1106 or adjacent to the anchor frame subcomponent interior surface (e.g., interior of the anchor frame subcomponent interior surface) of the anchor frame subcomponent 1100, and then extend back through the film to a location exterior or against the anchor frame subcomponent exterior surface 1108 and extend therearound. In some examples, the one or more constraining members individually or collectively operate to constrain the anchor frame subcomponent 1100 in a delivery configuration. In various examples, this includes one or more constraining members individually or collectively constrains the flange or flared portion of the anchor frame subcomponent 1100 in a delivery configuration. Additionally or alternatively, in some examples, a removable constraining sheath is disposed about the flange or flared portion of the anchor frame subcomponent 1100 in a delivery configuration. In some examples, one or more constraining members individually or collectively constrain the tissue engagement features to a delivery (undeployed) configuration. Additionally or alternatively, in some examples, a removable constraining sheath is disposed about the tissue engagement features of the anchor frame subcomponent 1100. In some examples, the one or more constraining members are removed from the anchor frame subcomponent 1100 during deployment of the anchor frame subcomponent 1100. In some examples, the constraining members includes a fiber. In some examples, the constraining members includes a wire. In some examples, one or more lockwires engage a first end of the one or more constraining members at or proximate the anchor frame subcomponent 1100 such that tension can be applied to an opposing second end of the one or more constraining members. In various examples, tensioning the one or more constraining members operates to maintain the anchor frame subcomponent 1100 in the delivery configuration.

In various examples, one or more constraining members are disposed about the leaflet frame subcomponent 1200 in the delivery configuration. For example, a third constraining member is disposed about the leaflet frame subcomponent inlet end 1202 of the leaflet frame subcomponent 1200 and a fourth constraining member is disposed about the leaflet frame subcomponent outlet end 1204 of the leaflet frame subcomponent 1200. Each constraining member may extend about a leaflet frame subcomponent exterior surface 1208 of the leaflet frame subcomponent 1200. In some such examples, one or more of the constraining members may be woven through one or more portions of the film disposed about the leaflet frame subcomponent 1200. In some examples, one or more of the constraining members that extend circumferentially about the leaflet frame subcomponent exterior surface 1208, or otherwise extend through a portion of the film, and extend along a portion of the leaflet frame subcomponent interior surface 1206 of the leaflet frame subcomponent 1200, and then extend back through the film to the leaflet frame subcomponent exterior surface 1208 and extend therearound.

Additionally or alternatively, in some examples, a removable constraining sheath is disposed about the tissue engagement features of the leaflet frame subcomponent 1200. It will be appreciated that the removable constraining sheath may be disposed about both the leaflet frame subcomponent 1200 and the anchor frame subcomponent 1100 (see discussion above). In some examples, the one or more constraining members are removed from the leaflet frame subcomponent 1200 during deployment of the leaflet frame subcomponent 1200. In some examples, the constraining members includes a fiber. In some examples, the constraining members includes a wire. In some examples, one or more lockwires engage a first end of the one or more constraining members at or proximate the leaflet frame subcomponent 1200 such that tension can be applied to an opposing second end of the one or more constraining members. In various examples, tensioning the one or more constraining members operates to maintain the leaflet frame subcomponent 1200 in the delivery configuration.

Interlock Features

In various embodiments, in addition to facilitating a positive engagement with an implant site to anchor the prosthetic valve 1000 to the surrounding tissue, the anchor frame subcomponent 1100 additionally or alternatively includes one or more mechanisms that facilitate a positive engagement with the leaflet frame subcomponent 1200 upon nesting the anchor frame subcomponent 1100 and the leaflet frame subcomponent 1200. Specifically, in various examples, the anchor frame subcomponent 1100 includes one or more interlock features 1120 that project into the anchor frame subcomponent interior region 1110 of the anchor frame subcomponent 1100. These interlock features 1120 are configured to engage the leaflet frame subcomponent 1200 as nested and maintain a relative axial position (or at least minimize relative axial movement) between the anchor frame subcomponent 1100 and the leaflet frame subcomponent 1200. Thus, according to various examples, one or more interlock features 1120 are incorporated with the prosthetic valve 1000 and operate to help maintain a coupling between the leaflet frame subcomponent 1200 and the anchor frame subcomponent 1100.

In various examples, the interlock features 1120 are structures that project or otherwise extend away from the anchor frame subcomponent interior surface 1106 and/or the anchor frame subcomponent exterior surface 1108, respectively, and toward the anchor frame subcomponent interior region 1110 defined by the anchor frame subcomponent 1100. In some examples, the one or more interlock features 1120 are in the form of one or more tabs.

In some examples, the one or more interlock features 1120 have a free end 1122 and a base 1124. In some examples, the free end 1122 is an end that is not otherwise coupled to or mated with the anchor frame subcomponent 1100. The base 1124 is generally the portion of the interlock feature that couples to or is otherwise integral with the anchor frame subcomponent 1100. Generally, the free end 1122 is operable to move relative to the anchor frame subcomponent 1100, while the base 1124 is coupled to the anchor frame subcomponent 1100.

Though a variety of geometries are envisioned, the non-limiting examples of the interlock features 1120 illustrated in FIGS. 4A and 4B are each elongate elements. In addition, the free end 1122 is illustrated as being a generally blunt or round end, though the free end 1122 of the one or more interlock features 1120, generally, may alternatively be pointed or possess other suitable geometry such as a curved shape (e.g., an s-shape). In other words, other geometries suitable for engaging the leaflet frame subcomponent 1200 when it is nested with the anchor frame subcomponent 1100 in the manner illustrated and described herein are envisioned and may be utilized without departing from the spirit or scope of the disclosure. In some examples, the free end 1122 of the one or more interlock features 1120 is shaped such that it is operable to slide along the exterior of the leaflet frame subcomponent 1200. As mentioned above, in some examples, a film or other covering material covers one or more portions of the leaflet frame subcomponent 1200. Thus, in some examples, the free end 1122 of the one or more interlock features 1120 is shaped and sized in a manner that allows the one or more interlock features 1120 to slide along the exterior of the leaflet frame subcomponent 1200 without binding. In one nonlimiting example, the one or more interlock features 1120 are from five hundred (500) microns in length to two (2) millimeters in length (e.g., six-hundred (600) microns) and are angled from fifteen (15) degrees to seventy-five (75) degrees (e.g., forty-five (45) degrees) relative to longitudinal axis of the anchor frame subcomponent 1100 and/or the interior of the anchor frame subcomponent 1100. It will be appreciated, however, that a number of angle and length configurations are contemplated and fall within the scope of the present application, including approximate values of any of the foregoing.

Similar to the tissue engagement features 1118, the interlock features 1120 may be arranged in one or more rows along a longitudinal axis of the anchor frame subcomponent 1100. That is, in various examples, anchor frame subcomponent 1100 may include a first set (e.g., a row) of interlock features and a second set (e.g., a row) of interlock features longitudinally offset relative to the first set of interlock features. In one such example, the first set of interlock features is more proximate the anchor frame subcomponent outlet end 1104 of the anchor frame subcomponent 1100 than is the second set of interlock features. In various examples, while the interlock features 1120 are configured to project away from the anchor frame subcomponent 1100 when the anchor frame subcomponent 1100 is in the deployed configuration, the interlock features 1120 are stowed or do not otherwise project away from the anchor frame subcomponent 1100 when the anchor frame subcomponent 1100 is compressed in the delivery configuration. Thus, in various examples, the interlock features 1120 are configured to transition between a stowed or delivery configuration and a projecting or deployed configuration. Thus, in various examples, the interlock features 1120 are resilient members that are configured to deflect under certain conditions.

In various examples, as mentioned above, the interlock features 1120 are configured to engage the leaflet frame subcomponent 1200 as it is nested with the anchor frame subcomponent 1100 in-situ. In some examples, as discussed further below, the interlock features 1120 temporarily deflect from an engaged position to facilitate nesting of the leaflet frame subcomponent 1200 with the anchor frame subcomponent 1100, and subsequently return to the engaged position after the leaflet frame subcomponent 1200 is nested with the anchor frame subcomponent 1100. In various examples, the interlock features 1120 return to the engaged position upon the leaflet frame subcomponent 1200 being proximally advanced a suitable amount relative to the anchor frame subcomponent 1100. Put differently, in some examples, the interlock features 1120 of the anchor frame subcomponent 1100 are operable to adopt an engaged position where they engage the leaflet frame subcomponent 1200 and minimize relative axial translation between the leaflet frame subcomponent 1200 and the anchor frame subcomponent 1100 upon proximally advancing the leaflet frame subcomponent 1200 a designated amount relative to the anchor frame subcomponent 1100.

In some examples, a delivery device upon which the anchor frame subcomponent 1100 is loaded during delivery causes stowing of the interlock features 1120.

In various examples, the interlock features 1120 are integral to the anchor frame subcomponent 1100. For example, one or more of the interlock features 1120 are formed in conjunction with and from the same material as the frame members 1112. In other examples, one or more of the interlock features 1120 are additionally or alternatively coupled to the anchor frame subcomponent 1100. That is, in some examples, one or more interlock features 1120 are additionally or alternatively attached to the anchor frame subcomponent 1100. In various examples, the one or more interlock features 1120 are circumferentially arranged about the anchor frame subcomponent 1100. In some examples, the one or more interlock features 1120 are evenly dispersed about the circumference of the anchor frame subcomponent. In a manner similar to that discussed above with respect to the tissue engagement features 1118, the angular offset between the anchors is generally a function of one or more of the arrangement of the frame members 1112 and the number of anchors dispersed about the anchor frame subcomponent 1100, as those of skill will appreciate.

It should be appreciated that while the interlock features are illustrated and described herein as extending from the anchor frame subcomponent 1100, in various examples, one or more interlock features additionally or alternatively extend from the leaflet frame subcomponent 1200. For instance, in some examples, the leaflet frame subcomponent includes one or more interlock features (not shown) that extend from the leaflet frame subcomponent exterior surface 1208 away from the leaflet frame subcomponent interior surface 1206 and that are operable to engage the anchor frame subcomponent 1100 upon nesting of the anchor frame subcomponent 1100 and the leaflet frame subcomponent 1200. In various examples, the interlock features of the leaflet frame subcomponent 1200 are positionable at a leaflet frame subcomponent inlet end 1202, a leaflet frame subcomponent outlet end 1204, or some position between the leaflet frame subcomponent inlet end 1202 and the leaflet frame subcomponent outlet end 1204 provided that the interlock features of the leaflet frame subcomponent 1200 are operable to engage the anchor frame subcomponent 1100 upon nesting of the anchor frame subcomponent 1100 and the leaflet frame subcomponent 1200. In various examples, the interlock features of the leaflet frame subcomponent are deflectable and stowable in a manner similar to the interlock features 1120 of the anchor frame subcomponent 1100, as previously described.

FIGS. 3A and 3B are side and axial views, respectively, of the leaflet frame subcomponent 1200, in accordance with an embodiment. The leaflet frame subcomponent 1200 is generally cylindrical or tubular member having a leaflet frame subcomponent inlet end 1202, a leaflet frame subcomponent outlet end 1204, a leaflet frame subcomponent interior surface 1206, and a leaflet frame subcomponent exterior surface 1208. In various examples, the leaflet frame subcomponent 1200 defines a leaflet frame subcomponent interior region 1209. For example, leaflet frame subcomponent interior region 1209 is a generally cylindrical void defined between the leaflet frame subcomponent inlet end 1202 and the leaflet frame subcomponent outlet end 1204, and the leaflet frame subcomponent interior surface 1206 of the leaflet frame subcomponent 1200. Generally, the leaflet frame subcomponent 1200 is configured to be received within at least a portion of the anchor frame subcomponent 1100, as mentioned above. It will be appreciated that non-limiting examples of the leaflet frame subcomponent 1200 can be provided with a diameter (e.g., a diameter of an interior or exterior surface of the leaflet frame subcomponent 1200) in a range of between twenty (20) millimeters and thirty (30) millimeters, depending on a patient's anatomy.

Tissue Retention Features

As shown in FIG. 8C, in various examples, the prosthetic valve 1000 (e.g., the leaflet frame subcomponent 1200) optionally includes one or more features that operate to grab or otherwise interface with native valve tissue (e.g., native leaflet tissue) or tissue surrounding the native valve being replaced. For example, the leaflet frame subcomponent 1200 (or another portion of the prosthetic valve 1000, such as the anchor frame subcomponent 1100) optionally includes one or more tissue retention features 1218 (also referred to herein as tissue graspers). The one or more tissue retention features 1218 may be formed as projections (e.g., projections of the leaflet frame subcomponent 1200) that are configured to interface with the patient's native tissue associated with the native valve.

In some examples, the one or more tissue retention features 1218 are configured to engage the native tissue. In some examples, the tissue retention features 1218 are configured to cause native tissue to be secured between the anchor frame subcomponent 1100 and the leaflet frame subcomponent 1200 as the anchor frame subcomponent 1100 and the leaflet frame subcomponent are nested together in-situ.

In some examples, the tissue retention features 1218 are configured to retain or secure native tissue without securing the native tissue between the leaflet frame subcomponent 1200 and the anchor frame subcomponent 1100. For example, the tissue retention features 1218 may project radially outward beyond the anchor frame subcomponent 1100. In such instances, the tissue retention features 1218 may be passed beyond the free edge of the tissue to be manipulated (e.g., the anterior leaflet (AL)), and then retracted to retain or secure the tissue. In still further examples, the anchor frame subcomponent 1100 may not be present, and in such instances the tissue retention features 1218 engage and retain or secure native tissue without regard to the anchor frame subcomponent 1100. Such configurations can help avoid the native tissue interfering with or otherwise obstructing the flow of fluid (e.g., blood) downstream or antegrade to the prosthetic valve 1000 after the prosthetic valve 1000 has been deployed.

In mitral valve repair/augmentation procedures for example, the capture and securement of at least the native anterior leaflet of the native mitral valve minimized that potential for the native anterior leaflet to deflect into the left ventricle and create a left ventricle outflow tract obstruction. Thus, in various embodiments, the one or more tissue retention features 1218 are configured to interface with one or more of the native leaflets associated with the native valve. Though mitral valve repair/augmentation procedures are discussed herein, it will be appreciated that the scope of the disclosure applies to repair/augmentation of the atrio-ventricular (AV) valves and the semilunar (SL) valves. The disclosure should therefore not be interpreted as being limited to mitral valve repair/augmentation.

In various examples, the tissue retention features 1218 are structures that project or otherwise extend away from the leaflet frame subcomponent 1200 and toward the tissue surrounding the prosthetic valve 1000 (e.g., the native valve orifice). In some examples, the one or more tissue retention features 1218 are in the form of one or more tabs. In some examples, the one or more tissue retention features 1218 are looped features having an apex and two ends, wherein the two ends are coupled to, integral with, extend from, or otherwise terminate into one or more portions of the leaflet frame subcomponent 1200. In some such examples, the apex is a free end that is operable to deflect and project away from the leaflet frame subcomponent 1200, as mentioned below.

In some examples, the one or more tissue retention features 1218 have a free end 1220 and a base 1222. In some examples, the free end 1220 is an end that is not otherwise coupled to or mated with the leaflet frame subcomponent 1200. The base 1222 includes one or more portions of the one or more tissue retention features 1218 that couple to or are otherwise integral with the leaflet frame subcomponent 1200. Generally, the free end 1220 is operable to move relative to the leaflet frame subcomponent 1200, while the base 1222 is coupled to the leaflet frame subcomponent 1200.

In some examples, the tissue retention features are simple barbs or hook features formed similarly to anchoring barbs, but in an inverted configuration. Though a variety of geometries are envisioned, another non-limiting exemplary design for the tissue retention features 1218 is illustrated in FIG. 8C as a generally triangularly shaped feature with a blunt end (though sharp ends and other features are contemplated for the tissue retention features 1218, as described below). As shown, each of the tissue retention features 1218 include a free end 1220 and a base 1222. Each tissue retention feature includes a first leg 1224 and a second leg 1226 that are each coupled to, integral with, extend from, or otherwise terminate into the leaflet frame subcomponent 1200.

As shown, the first leg 1224 and the second leg 1226 converge to form the free end 1220. In addition, while the free end 1220 is illustrated as being a generally blunt or round end, the free end 1220 may alternatively be pointed or possess other suitable geometry. In other words, other geometries suitable for engaging surrounding tissue in the manner illustrated and described herein are envisioned and may be utilized without departing from the spirit or scope of the disclosure. For instance, another non-limiting exemplary tissue retention feature includes an end coupled to or otherwise integral with the leaflet frame subcomponent 1200 and a plurality of free ends extending from the end coupled to the leaflet frame subcomponent 1200. Another non-limiting exemplary tissue retention feature includes a barb or similar feature having opposed single ends coupled to or otherwise integral with the leaflet frame subcomponent 1200. The profile of the free end 1220 may be one well suited for penetrating tissue (e.g., piercing) or penetrating between tissue (e.g., hooking) of the surrounding anatomy.

In various examples, the tissue retention features 1218 have a first side 1228 and a second side 1230. As shown, the first side 1228 faces the leaflet frame subcomponent exterior surface 1208 of the leaflet frame subcomponent 1200, and the second side 1230 faces away from the leaflet frame subcomponent exterior surface 1208 of the leaflet frame subcomponent. In some examples, a void or open space region is defined between the first side 1228 and the leaflet frame subcomponent exterior surface 1208 of the leaflet frame subcomponent 1200. In various examples, this open space region between the first side 1228 and the leaflet frame subcomponent exterior surface 1208 of the leaflet frame subcomponent 1200 is configured to accommodate a portion of native tissue (e.g., valve leaflets) from anatomy surrounding the prosthetic valve 1000. As previously referenced, the tissue retention features 1218 may also be configured to retain or secure native tissue without securing the native tissue between the leaflet frame subcomponent 1200 and the anchor frame subcomponent 1100. Again, the tissue retention features 1218 may project radially outward beyond the anchor frame subcomponent 1100 or, the anchor frame subcomponent 1100 may not be present according to various examples, and in such instances the tissue retention features 1218 engage and retain or secure native tissue without regard to the anchor frame subcomponent 1100.

Generally, the one or more tissue retention features 1218 of the leaflet frame subcomponent 1200 are situated along the leaflet frame subcomponent 1200 proximate the leaflet frame subcomponent outlet end 1204. In some examples, the base 1222 of the one or more tissue retention features 1218 forms part of the distal end of the leaflet frame subcomponent 1200. In other examples, the base 1222 of the one or more tissue retention features 1218 is situated proximal to the leaflet frame subcomponent outlet end 1204 of the leaflet frame subcomponent 1200. Thus, the one or more tissue retention features 1218 can be generally located at any position along the longitudinal axis of the leaflet frame subcomponent 1200 provided that the tissue retention features 1218 are appropriately sized and shaped for causing native tissue to be captured (e.g., between the anchor frame subcomponent 1100 and the leaflet frame subcomponent 1200), such as upon nesting of the anchor frame subcomponent 1100 where present and the leaflet frame subcomponent 1200, or as otherwise described.

In various examples, the one or more tissue retention features 1218 are circumferentially arranged about the leaflet frame subcomponent 1200. In some examples, the one or more tissue retention features 1218 are evenly dispersed about the circumference of the anchor frame subcomponent. For example, the tissue retention features 1218 are dispersed about the frame and are offset from one another by ninety (90) degrees depending on the number of tissue retention features. Alternatively, the tissue retention features 1218 may be dispersed about the frame and offset from one another by sixty (60) degrees, or some other angular offset, depending on the number of tissue retention features. Generally, the angular offset between the anchors is a function of the number of tissue retention features dispersed about the leaflet frame subcomponent 1200, as those of skill will appreciate. In some examples, the angular offset between the tissue retention features is additionally or alternatively based on an arrangement or pattern of the frame members 1212. Such configurations provide for a prosthetic valve that is deployable in virtually any angular orientation about the longitudinal axis of the prosthetic valve 1000. That is, such configurations minimize the need for physicians to orient the prosthetic valve 1000 about a longitudinal axis of the prosthetic valve 1000 relative to the surrounding native tissue.

In some examples, the tissue retention features are dispersed about the leaflet frame subcomponent 1200 based on the anatomy of the native tissue surrounding the natural valve to be replaced by the prosthetic valve. For example, the mitral valve is comprised of two native leaflets. In exemplary embodiments including a prosthetic valve configured for implantation to repair or augment a damaged or faulty native mitral valve, the tissue retention features of the leaflet frame subcomponent may be more heavily distributed within certain angular regions to increase the number of tissue retention features in proximity to the native leaflets to capture the native leaflets.

In various examples, as mentioned above, the one or more tissue retention features 1218 project away from the leaflet frame subcomponent 1200 toward the surrounding tissue when the leaflet frame subcomponent 1200 is in the deployed configuration. In some examples, the one or more tissue retention features 1218 project away from the leaflet frame subcomponent 1200 such that the free end 1220 is more radially offset from an axis of the leaflet frame subcomponent 1200 (e.g., extends more radially outwardly) than is the base 1222 of the one or more tissue retention features 1218. In other words, in various examples, one or more of the tissue retention features 1218 are angled relative to a longitudinal axis of the leaflet frame subcomponent 1200 and/or the leaflet frame subcomponent exterior surface 1208 of the leaflet frame subcomponent 1200 when the leaflet frame subcomponent 1200 is in the deployed configuration. Such a configuration provides that the open space region defined between the first side 1228 and the leaflet frame subcomponent exterior surface 1208 of the leaflet frame subcomponent 1200 is tapered. In some examples, the open space region is wedge-shaped.

In various examples, a length and angle configuration of the tissue retention features 1218 is based on the relative sizes of the anchor frame subcomponent 1100 and the leaflet frame subcomponent 1200. For example, the length and angle configuration of the tissue retention features 1218 is such that the tissue retention features 1218 do not prevent or otherwise obstruct the leaflet frame subcomponent 1200 from telescoping or otherwise being nested with the anchor frame subcomponent 1100. Additionally, however, the length and angle configuration of the tissue retention features 1218 is one that provides for the tissue engagement features engaging one or more of the native leaflets of the patient's anatomy, as discussed herein. In some nonlimiting examples, the tissue retention features 1218 have a length of between five-hundred (500) micrometers and 20 mm and project away from the leaflet frame subcomponent 1200 at an angle in a range of between thirty (30) and sixty (60) degrees. Accordingly, though a variety of other configurations are contemplated, one nonlimiting example configuration includes tissue engagement features having a length of approximately five (5) to ten (10) millimeters that project away from the leaflet frame subcomponent 1200 in the deployed configuration at an angle of approximately forty-five (45) degrees.

In various examples, the one or more tissue retention features 1218 are angled between fifteen (15) and forty five (45) degrees relative to the longitudinal axis of the leaflet frame subcomponent 1200. For instance, in some examples, when deployed, the one or more tissue retention features 1218 of the leaflet frame subcomponent 1200 is angled at approximately thirty (30) degrees relative to a longitudinal axis of the leaflet frame subcomponent 1200. Generally, the one or more tissue retention features 1218 may be angled less than fifteen (15) or alternatively more than forty five (45) degrees relative to the longitudinal axis of the leaflet frame subcomponent 1200, though as the angle approaches zero (0) degrees and ninety (90) degrees, the ability of the one or more tissue retention features 1218 to engage and capture tissue diminishes.

In various examples, the one or more tissue retention features 1218 of the leaflet frame subcomponent 1200 are generally oriented such that the free end 1220 thereof is situated proximal to the base 1222 thereof. As discussed in greater detail below, such a configuration provides for a tissue retention feature that is operable to engage and capture native tissue (e.g. as the leaflet frame subcomponent 1200 and the anchor frame subcomponent 1100 are nested in-situ) and may cause the native tissue to be captured between the leaflet frame subcomponent 1200 and the anchor frame subcomponent 1100.

In various examples, while the tissue retention features 1218 are configured to project away from the leaflet frame subcomponent 1200 when the leaflet frame subcomponent 1200 is in the deployed configuration, the tissue retention features 1218 are stowed or do not otherwise project away from the leaflet frame subcomponent 1200 when the leaflet frame subcomponent 1200 is compressed or collapsed in the delivery configuration. In some examples, a constraining member disposed about the leaflet frame subcomponent 1200 during delivery cases stowing of the tissue retention features 1218. In some examples, the tissue retention features 1218 are stowed in apertures 1216 of the leaflet frame subcomponent 1200. Thus, in various examples, the tissue retention features 1218 are configured to transition between a stowed or delivery configuration and a projecting or deployed configuration.

In some examples, the tissue retention features 1218 are resilient structures. In some examples, the tissue retention features 1218 are biased to project away from the leaflet frame subcomponent 1200. In other words, in various examples the tissue retention features 1218 naturally project away from the leaflet frame subcomponent 1200 upon the leaflet frame subcomponent 1200 expanding to the deployed configuration (or the constraining member otherwise being removed).

In various examples, the tissue retention features 1218 are integral to the leaflet frame subcomponent 1200. For example, one or more of the tissue retention features 1218 are formed in conjunction with and from the same material as the frame members 1212. In other examples, one or more of the tissue retention features 1218 are additionally or alternatively coupled to the anchor frame subcomponent 1100.

Deployment and Nesting

Figure 5A:
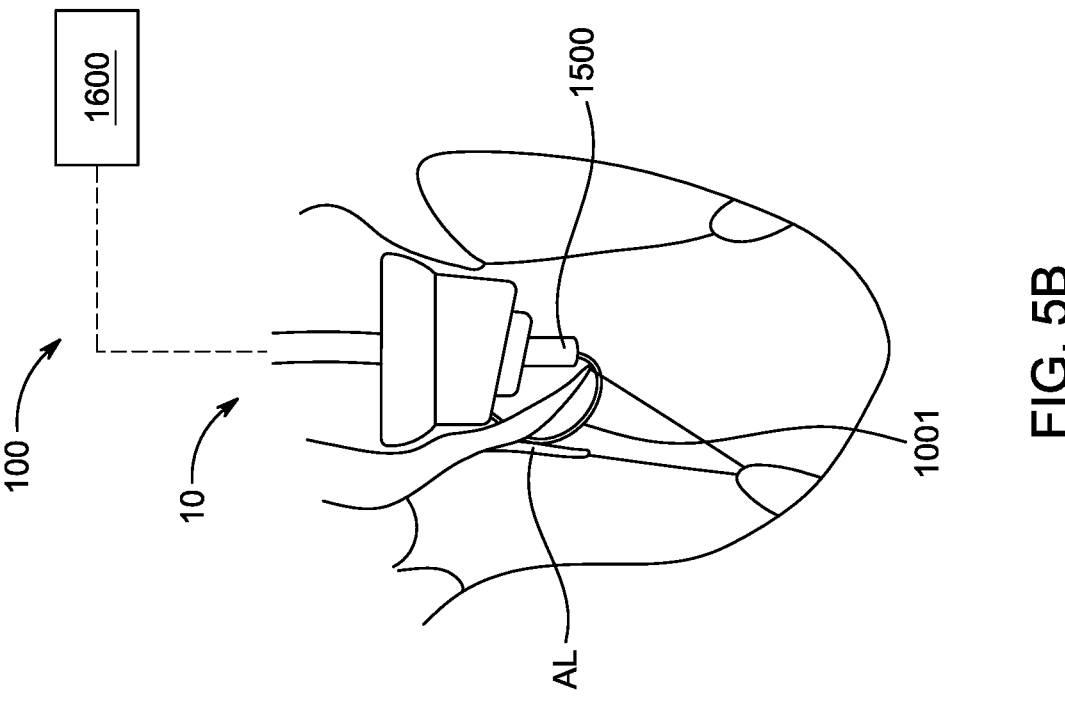
FIGS. 5A and 5B show a cutting method, according to some embodiments.
Figure 5B:
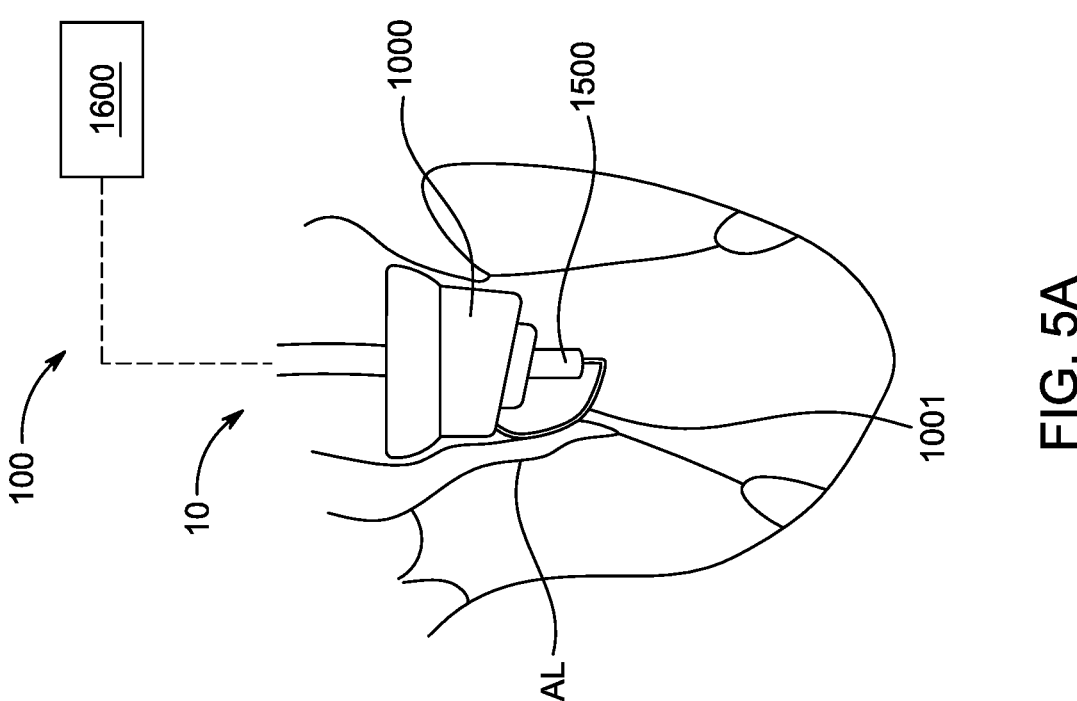
Figure 6A:
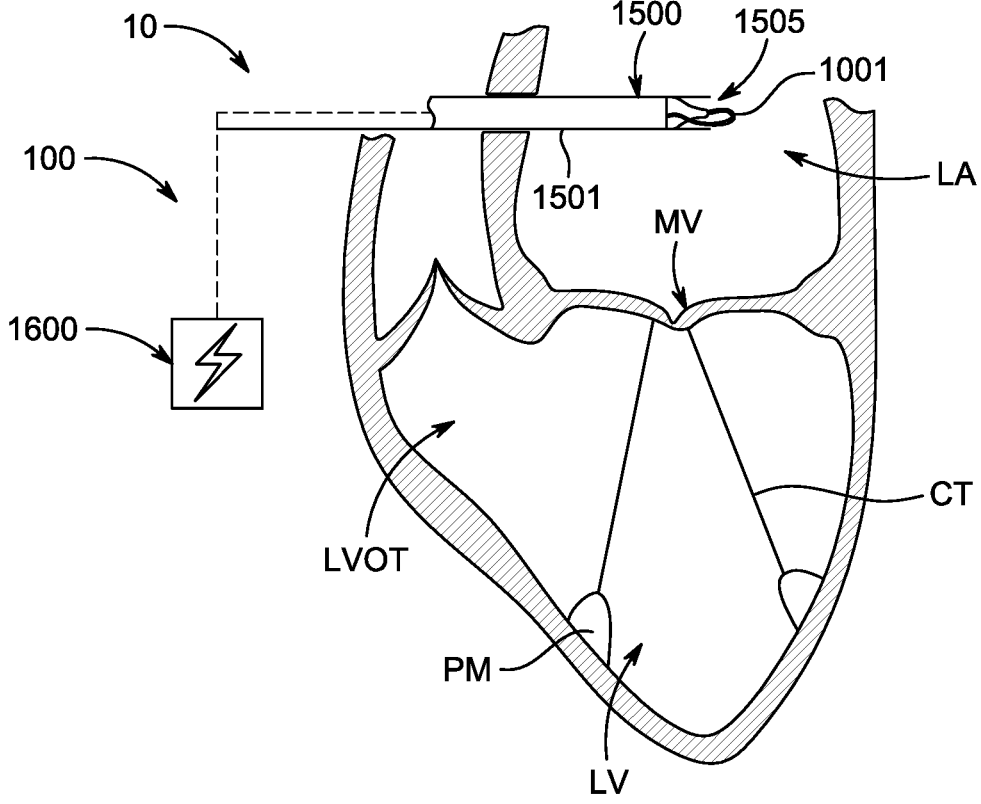
FIGS. 6A to 6G are cross-sectional views of a heart illustrating a delivery procedure, according to some embodiments.
Figure 6B:
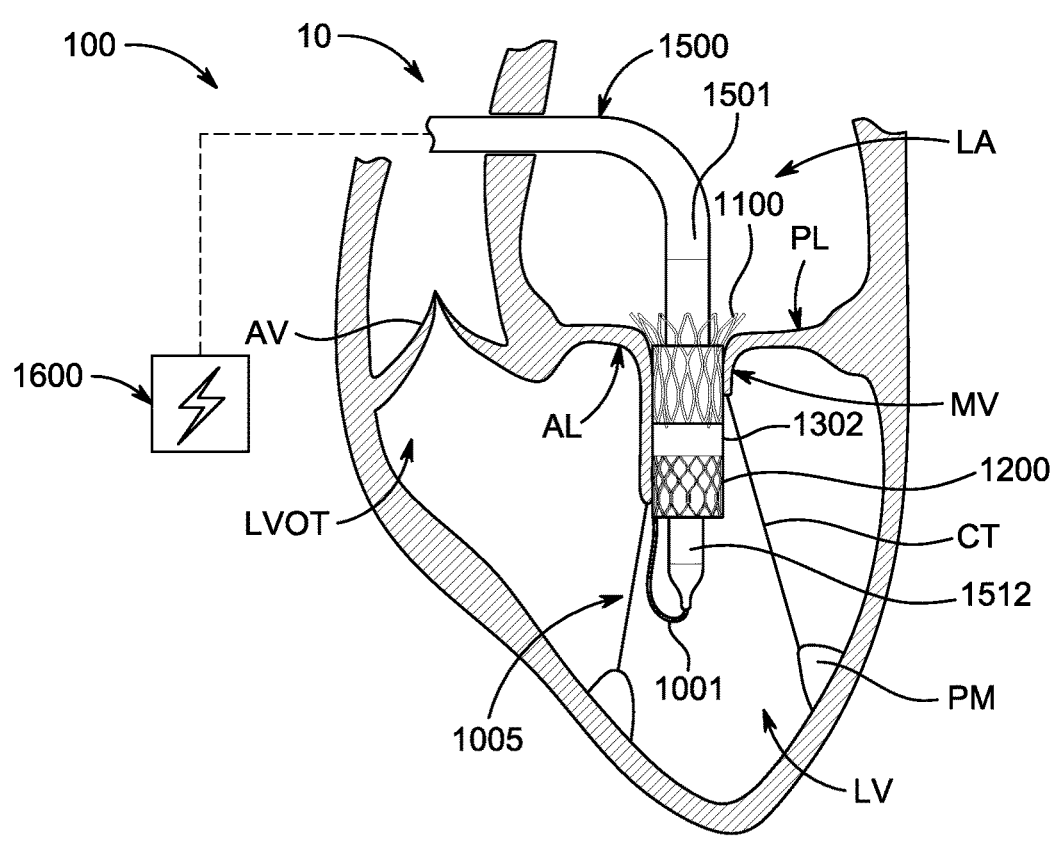
Figure 6C:
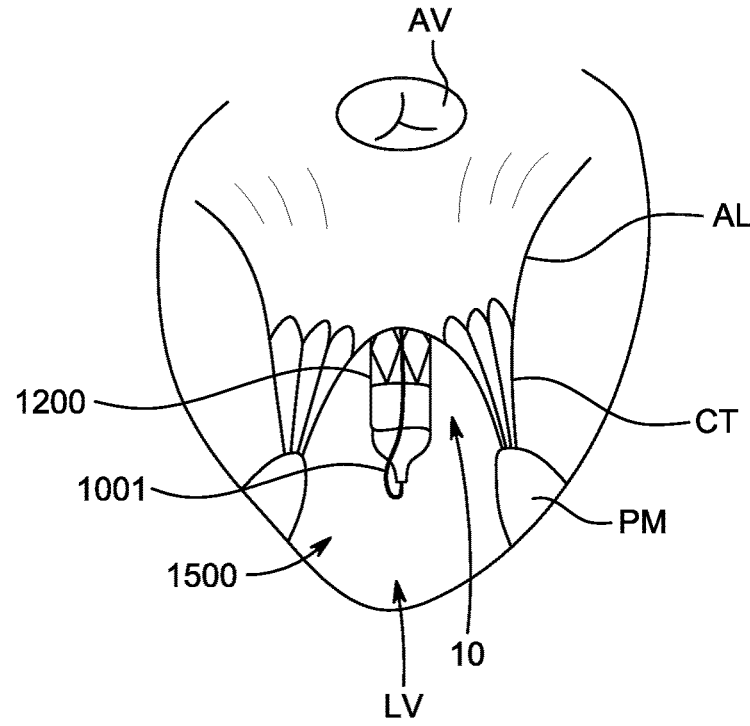
Figure 6D:
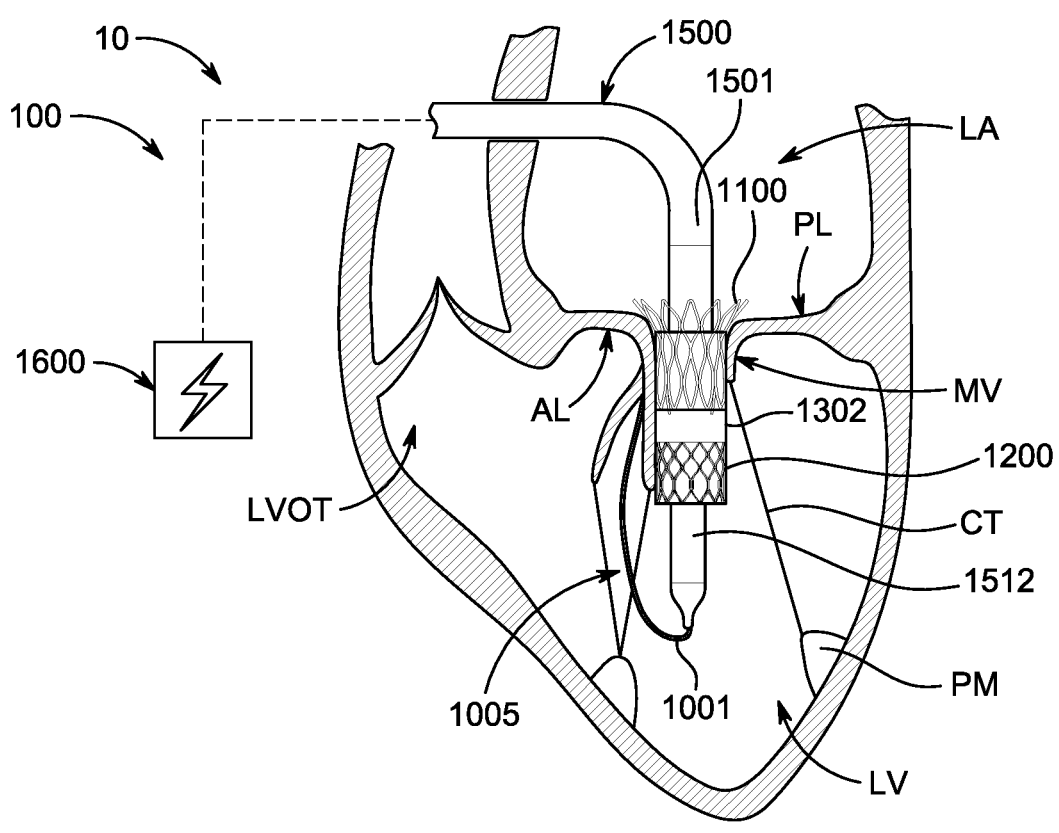
Figure 6E:
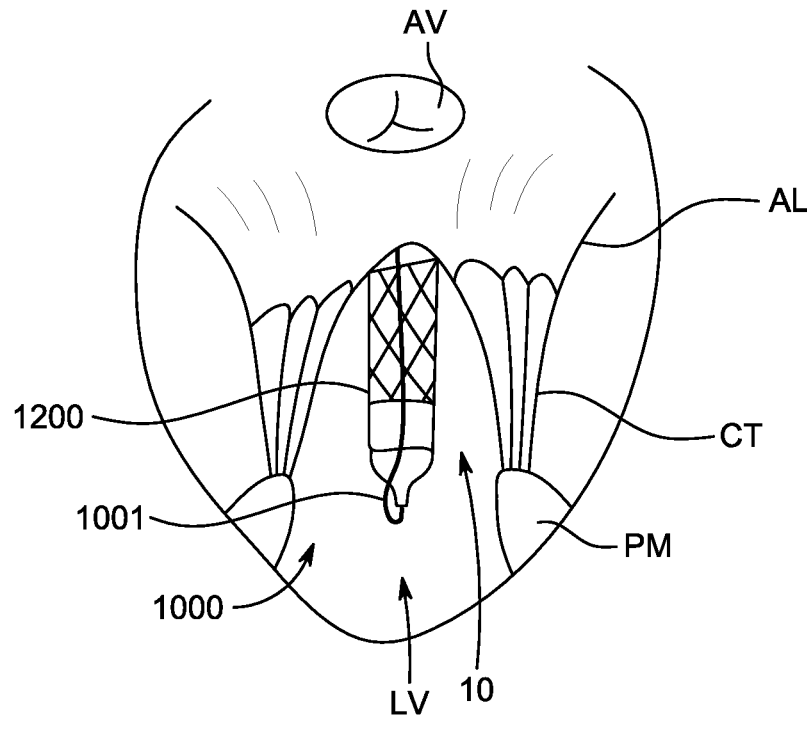
Figure 6F:
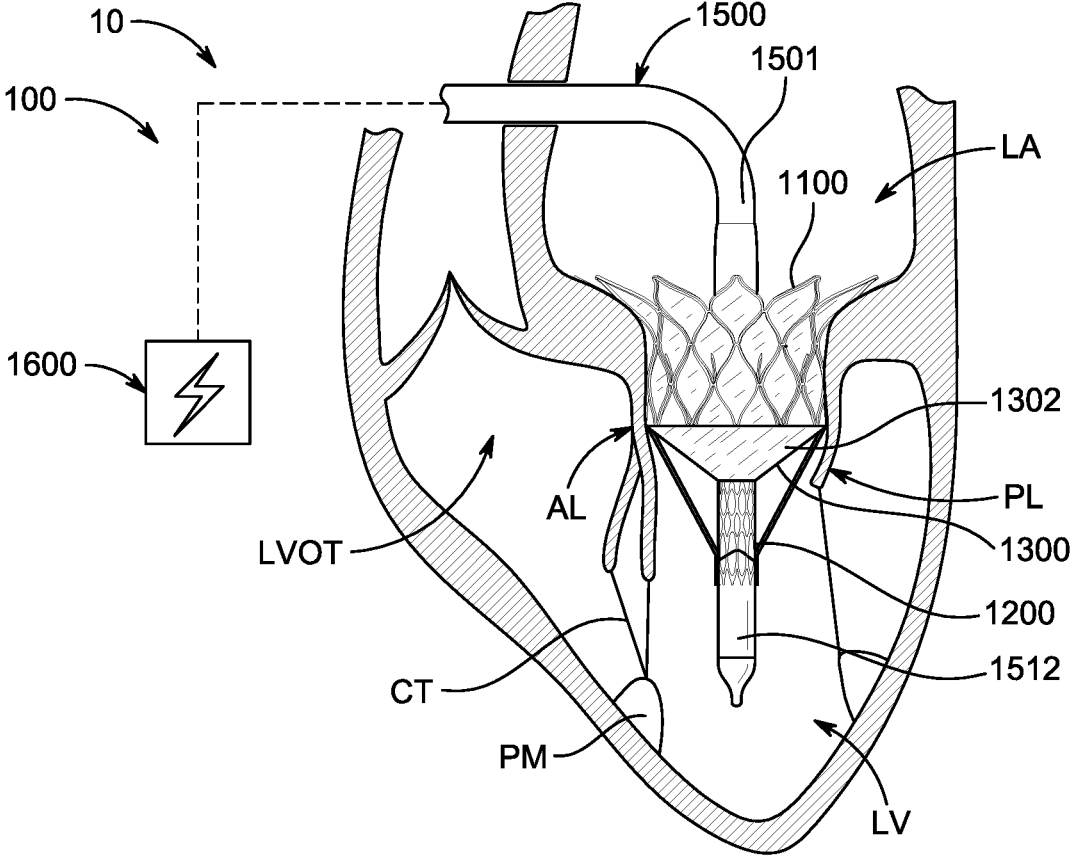
Figure 6G:
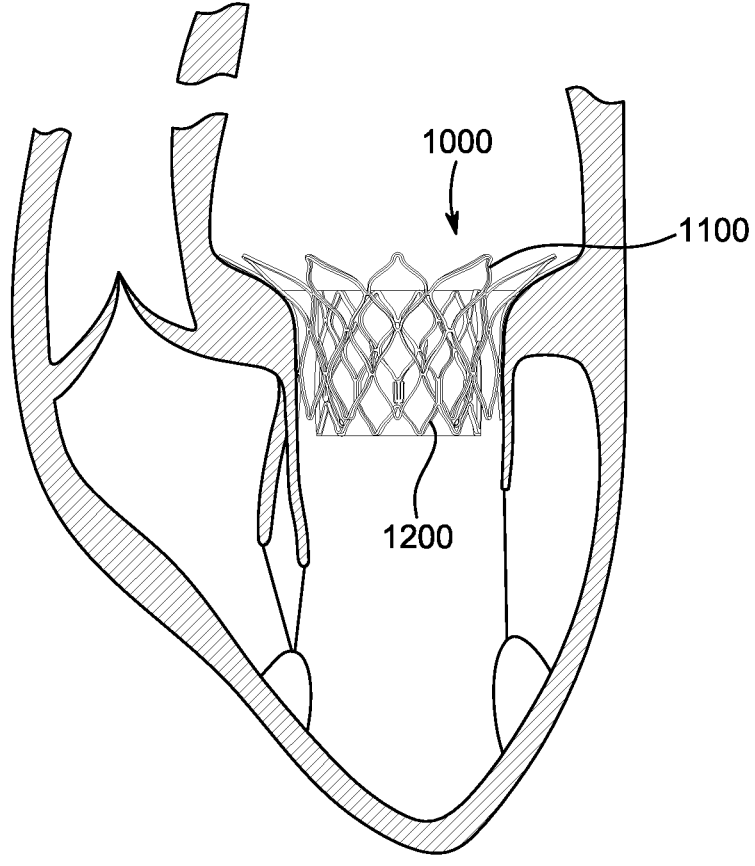
Figure 6H:
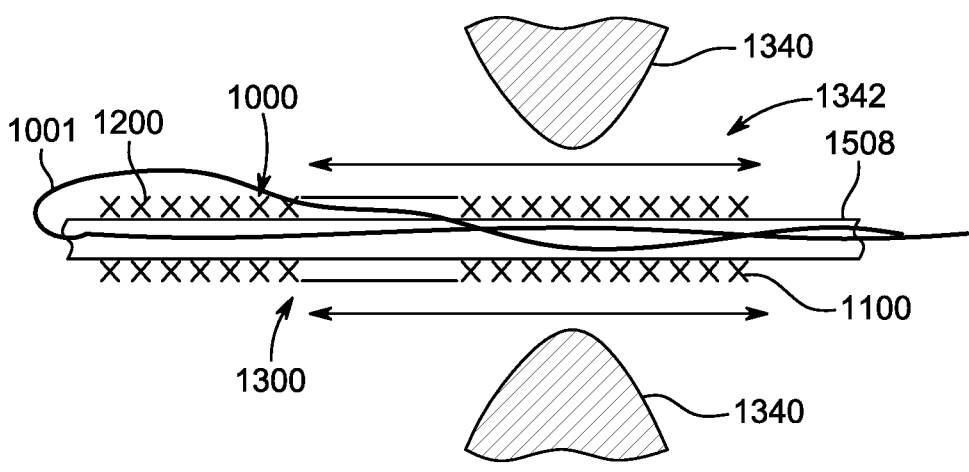
FIGS. 6H to 6K are schematic, sectional views of a prosthetic valve and delivery device at various stages of device deployment, according to some embodiments.
Figure 6I:
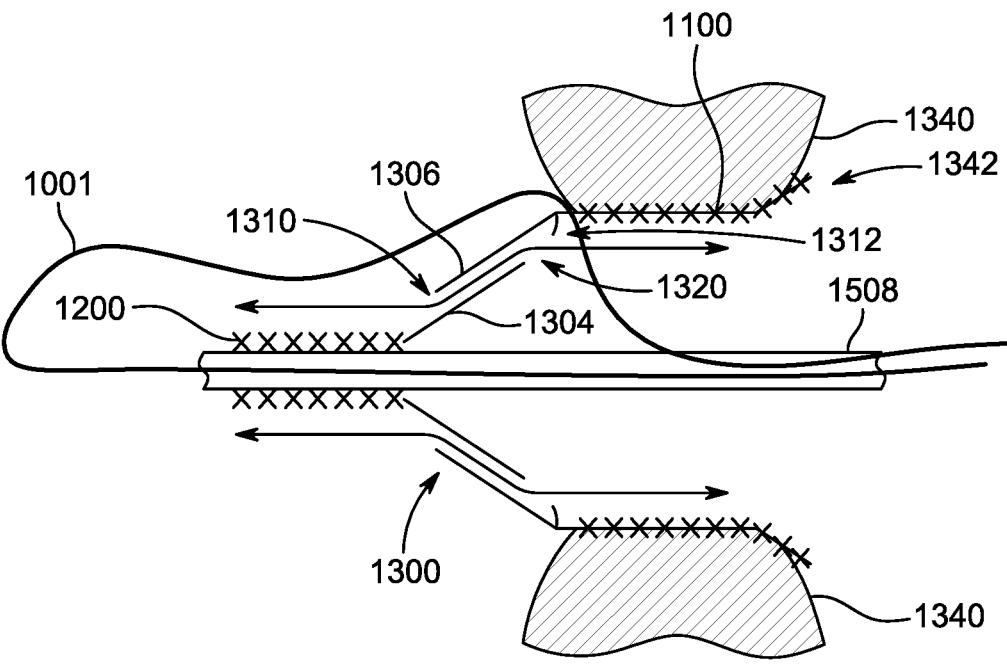

FIGS. 5 and 6H show the prosthetic valve 1000 in a predeployed configuration, and FIG. 6I, for example, is a side view of the prosthetic valve 1000 in a partially deployed configuration (e.g., prior to nesting the anchor frame subcomponent 1100 and the leaflet frame subcomponent 1200) with the interstage 1300 therebetween. FIG. 4C illustrates the prosthetic valve 1000 loaded on a delivery device or delivery device 1500 (e.g., a catheter) in a predeployed configuration with the anchor frame subcomponent 1100 and the leaflet frame subcomponent 1200 being longitudinally offset from one another (also referred to as being delivered in series) and coupled together with the interstage 1300 therebetween. In both the predeployed and partially deployed configurations, the anchor frame subcomponent 1100 and the leaflet frame subcomponent 1200 are longitudinally offset relative to one another. In some examples, prior to nesting the anchor frame subcomponent 1100 and the leaflet frame subcomponent 1200, the leaflet frame subcomponent inlet end 1202 of the leaflet frame subcomponent 1200 is positioned distal to the anchor frame subcomponent outlet end 1104 of the anchor frame subcomponent 1100 with the interstage 1300 coupled thereto and positioned therebetween coupling them together.

With continued reference to the non-limiting example of FIG. 4C, in the predeployed configuration, the prosthetic valve 1000 is loaded on a delivery device 1500 such that the anchor frame subcomponent 1100 and the leaflet frame subcomponent 1200 are longitudinally offset from one another. Specifically, as shown, a leaflet frame subcomponent inlet end 1202 of the leaflet frame subcomponent 1200 is positioned distal to the anchor frame subcomponent outlet end 1104 of the anchor frame subcomponent 1100. Generally, a removable constraining member (not shown), such as a constraining sheath or a constraining tube is disposed about the prosthetic valve 1000 when the prosthetic valve 1000 is in the predeployed configuration, as those of skill in the art should appreciate. The constraining member has been removed in this illustrated example such that the underlying components of the prosthetic valve 1000 that would otherwise be masked or concealed by the constraining member are viewable.

In various examples, the longitudinal separation or offset of the anchor frame subcomponent 1100 and the leaflet frame subcomponent 1200 provides for a low-profile delivery configuration that can be easily tracked through the vasculature of the patient. For instance, by longitudinally offsetting the anchor frame subcomponent 1100 and the leaflet frame subcomponent 1200, a profile of the delivery system can be minimized because, unlike conventional designs, the anchor frame subcomponent 1100, the leaflet frame subcomponent 1200, and the interstage 1300 do not overlap one another during delivery. In some examples, a maximum profile of the delivery device 1500 including the prosthetic valve 1000 and the constraining member (no shown) can be twenty-four French (24F) or less, although a variety of profiles are contemplated.

Additionally, a region 1502 of the delivery device 1500 positioned between the anchor frame subcomponent 1100 and the leaflet frame subcomponent 1200 and adjacent to the interstage 1300 is operable to bend such that the anchor frame subcomponent 1100 and the leaflet frame subcomponent 1200 are temporarily misaligned with one another. In some examples, such a configuration is akin to rail cars navigating a curve. Such a configuration is beneficial in procedures where the prosthetic valve 1000 is delivered to a treatment region trans-septally, which may require a delivery device to bend ninety (90) degrees or more within the left atrium of the heart.

In various examples, upon removing a constraining member (not shown) in-situ, the prosthetic valve 1000 is operable to adopt a partially deployed configuration. In some examples, when in the partially deployed configuration, despite having expanded relative to the predeployed delivery profile, the anchor frame subcomponent 1100 and the leaflet frame subcomponent 1200 remain longitudinally offset relative to one another. For example, as shown in FIG. 1A, the anchor frame subcomponent 1100 and the leaflet frame subcomponent 1200 are longitudinally offset from one another such that the leaflet frame subcomponent inlet end 1202 of the leaflet frame subcomponent 1200 is positioned distal to the anchor frame subcomponent outlet end 1104 of the anchor frame subcomponent 1100 with the interstage 1300 therebetween.

In various examples, after deploying the prosthetic valve 1000 to the predeployed configuration, the anchor frame subcomponent 1100 and the leaflet frame subcomponent 1200 can be nested with one another, with the interstage 1300 being everted therebetween, in-situ. That is, in various examples, the prosthetic valve 1000 can be percutaneously delivered to a treatment region of a patient's anatomy with the anchor frame subcomponent 1100 and the leaflet frame subcomponent 1200 longitudinally offset relative to one another (e.g., an inlet end of the leaflet frame subcomponent 1200 being positioned distal to an outlet end of the anchor frame subcomponent 1100), and subsequently nested with one another (e.g., an inlet end of the leaflet frame subcomponent 1200 being repositioned to a position proximal to an outlet end of the anchor frame subcomponent 1100) in-situ.

FIGS. 5A and 5B show a cutting sequence, according to some embodiments. As shown in FIG. 5A, the delivery system 10 is used to deploy the prosthetic valve 1000 to its fully deployed state at a desired treatment site (e.g., a native mitral valve annulus). Following deployment (and potentially during deployment), the cutting element 1001 is engaged with tissue to be cut, such as the anterior leaflet AL. The cutting element 1001 may be extended, or otherwise adjusted to press against the anterior leaflet AL, to help tent, or displace the anterior leaflet AL as desired. The cutting element 1001 is then activated, such as by electrifying the cutting element 1001, and the tissue of the anterior leaflet AL is cut (e.g., to prevent or reduce obstruction of the left ventricular outflow tract (LVOT).

FIGS. 6A to 6G illustrate a non-limiting exemplary deployment sequence and nesting configuration of the prosthetic valve 1000 in-situ during a mitral valve ("MV") replacement procedure, with a cross-section of a portion of the heart for illustrative purposes. In FIG. 6A, the left atrium ("LA") is accessed transseptally by a delivery device 1500. In various examples, the delivery device 1500 delivered percutaneously and is coupled to a control system 1600 outside of the body. Accessing the left atrium transseptally can be done in accordance with techniques as known those of skill in the art.

As shown, the cutting element 1001 optionally extends from the outlet end 1505 and is at least partially covered by the outer sheath 1501. In some examples, the outer sheath 1501 is also positioned over a portion of or over the entirety of the prosthetic valve 1000 (not shown in FIG. 6A because the prosthetic valve 1000 is hidden from view). In this configuration, the outer sheath 1501 functions both as a compression member which keeps the prosthetic valve 1000 in the compressed configuration until the outer sheath 1501 is proximally retracted from the prosthetic valve 1000 and as a preventative member which prevents the cutting element 1001 from cutting any neighboring tissue if the user or the operator is to inadvertently activate the cutting element 1001 before the prosthetic valve 1000 reaches the intended destination, thereby reducing the damage caused by the cutting element 1001 to the minimum.

Upon gaining access to the left atrium transseptally, the delivery device 1500 is positioned for deployment of the prosthetic valve 1000. For example, as shown in FIG. 6B, the delivery device 1500 is advanced through the mitral valve and into the left ventricle ("LV"). In some examples, advancement of the delivery device 1500 through the mitral valve causes the anterior leaflet ("AL") positioned opposite to the posterior leaflet ("PL") of the mitral valve to deflect toward the LVOT in the left ventricle.

In various examples, the delivery device 1500 is positioned such that the prosthetic valve 1000 is properly oriented relative to the mitral valve. As shown in FIG. 6B, the delivery device 1500 is positioned such that the anchor frame subcomponent 1100 is adjacent a mitral valve orifice and the anterior leaflet.

As shown, the cutting element 1001 is also disposed adjacent and in contact with the anterior leaflet (AL). FIG. 6C shows the configuration of FIG. 6B from the side, such that a portion of the cutting element 1001, the leaflet frame subcomponent 1200, and the delivery device 1500 are shown behind the anterior leaflet. In various examples, once properly positioned, the outer sheath 1501 of the delivery device 1500 is retracted relative to the prosthetic valve 1000, thereby exposing the prosthetic valve 1000. In various examples, the prosthetic valve 1000 is disposed about a support portion 1512 of the delivery device 1500, as discussed in greater detail below.

In some embodiments, the prosthetic valve 1000 is then fully deployed (expanded, and nested as described in association with FIGS. 6D to 6G) prior to performing a cutting sequence. Following full deployment, and as described in association with FIGS. 5A and 5B, the cutting element 1001 is then used to cut the desired tissue, such as the anterior leaflet (AL). For example, the control system 1600, or more specifically the current source 1003 (FIG. 1D) of the control system 1600, is activated, causing an electrical current to pass through the cutting element 1001. In this case, the active portion 1005 (e.g., FIGS. 1A to 1C) of the cutting element 1001 operates to cut tissue adjacent to and/or in direct contact with the active portion 1005, as can be seen in FIG. 5B. As shown, the anterior leaflet (AL) may be cut into two leaflet portions, or split in two. In some examples, the anterior leaflet (AL) may be cut into three leaflet portions, or more, depending on the configuration of the cutting element 1001 and/or the cutting operation that is undertaken. For example, instead of a single wire and a Y-shaped or V-shaped wire construct may be used as the cutting element 1001 such that the leaflet is separated into three portions, for example. Other suitable configurations for the cutting element 1001 may also be employed.

In some examples, after the leaflet or other tissue is cut, the user may unlock or otherwise release the locking mechanism 1006 (FIG. 1D) to release one end of the cutting element 1001 such that the cutting element 1001 may be retracted proximally. When one end of the cutting element 1001 is retracted, the cutting element 1001 can be disengaged from the prosthetic valve 1000 and thereafter be fully removed from the body through the delivery device 1500. For example, the cutting element 1001 can simply be pulled through the delivery device 1500 back out of the body of a patient. This sequence can be particularly helpful as proper functioning of the prosthetic valve 1000 (or other implant) can first be observed, or the need for performing a cutting operation can first be assessed, prior to cutting tissue.

In some examples, the cutting element 1001 is retracted prior to expanding the prosthetic valve 1000, although the ordering of those steps may be altered as desired. And, as described below, in some examples, the prosthetic valve 1000 is not fully deployed (e.g., including nesting) when the cutting element 1001 is operated to cut tissue (e.g., the anterior leaflet (AL)). For example, in some embodiments, following positioning of the prosthetic valve 1000 at the desired treatment site, the control system 1600, or more specifically the current source 1003 of the control system 1600, is activated, causing an electrical current to pass through the cutting element 1001 as shown in FIG. 6D. In this case, the active portion 1005 of the cutting element 1001 operates to cut tissue adjacent to and/or in direct contact with the active portion 1005, as can be seen in FIG. 6E which shows the configuration of FIG. 6D from the side. Similar to the example of FIGS. 5A and 5B, the anterior leaflet (AL) may be cut into two leaflet portions, or split in two, though the anterior leaflet (AL) may be cut into three leaflet portions, or more, depending on the configuration of the cutting element 1001 and/or the cutting operation that is undertaken. As previously referenced, instead of a single wire and a Y-shaped or V-shaped wire construct may be used as the cutting element 1001 such that the leaflet is separated into three portions, for example. Other suitable configurations for the cutting element 1001 may also be employed here as well.

In some examples, after the leaflet or other tissue is cut, the user may unlock or otherwise release the locking mechanism 1006 to release one end of the cutting element 1001 such that the cutting element 1001 may be retracted proximally. When one end of the cutting element 1001 is retracted, the cutting element 1001 can be disengaged from the prosthetic valve 1000 and thereafter be fully removed from the body through the delivery device 1500. For example, the cutting element 1001 can simply be pulled through the delivery device 1500 back out of the body of a patient. In some examples, the cutting element 1001 is retracted prior to expanding the prosthetic valve 1000, although the ordering of those steps may be altered as desired. In some examples, the prosthetic valve 1000 is fully deployed (e.g., including nesting) and the cutting element 1001 is then operated to cut tissue (e.g., the anterior leaflet (AL)) and subsequently retracted from the body of the patient. This sequence can be particularly helpful as proper functioning of the prosthetic valve 1000 (or other implant) can first be observed, or the need for performing a cutting operation can first be assessed, prior to cutting tissue.

In various examples, with the prosthetic valve 1000 exposed, the prosthetic valve 1000 expands or is otherwise expanded via the use of one or more expansion aids, including but not limited to one or more inflatable balloons. In some examples, expansion of the prosthetic valve 1000 includes the anchor frame subcomponent 1100 expanding relative to the tissue of the mitral valve. In some examples, such expansion causes the anterior leaflet (AL) of the mitral valve to deflect and may obstruct the left ventricular outflow tract (LVOT) that leads to the aortic valve (AV). In various examples, as the anchor frame subcomponent 1100 expands or is expanded, the one or more tissue engagement features 1118 of the anchor frame subcomponent 1100 engage the tissue surrounding the anchor frame subcomponent 1100 (e.g., the mitral valve orifice) and secure the anchor frame subcomponent 1100 against dislodgement from the surrounding tissue and migration of the anchor frame subcomponent 1100.

In various examples, after the anchor frame subcomponent 1100 is expanded and secured relative to the native valve orifice, the anchor frame subcomponent 1100 and the leaflet frame subcomponent 1200 are nested together. In various examples, nesting of the anchor frame subcomponent 1100 and the leaflet frame subcomponent 1200 in-situ involves proximally advancing the leaflet frame subcomponent 1200 relative to the anchor frame subcomponent 1100. In various examples, the leaflet frame subcomponent 1200 is in a collapsed, or intermediate expanded configuration when nested into the anchor frame subcomponent 1100. For example, FIG. 6F shows the leaflet frame subcomponent 1200 in an unexpanded, unnested configuration. Typically, the leaflet frame subcomponent 1200 is constrained, or at least partially constrained (e.g., to an intermediate diameter) and is nested into the anchor frame subcomponent 1100 prior to being fully expanded (either prior to being expanded to an intermediate diameter, or after being expanded to the intermediate diameter but prior to being fully expanded). By nesting the leaflet frame subcomponent 1200 into the anchor frame subcomponent 1100 when the leaflet frame subcomponent 1200 is at least partially collapsed, nesting may be facilitated (e.g., there may be less longitudinal resistance encountered during nesting).

In various examples, the leaflet frame subcomponent 1200 is proximally advanced relative to the anchor frame subcomponent 1100 by way of proximally withdrawing the delivery device 1500. For instance, in some examples, the delivery device 1500 includes one or more of the constraining members referred to above. In various examples, the constraining members releasably couple the delivery device 1500 to the leaflet frame subcomponent 1200 such that the one or more of the constraining members are operable to transfer a proximal translation of the delivery device 1500 into a proximal translation of the leaflet frame subcomponent 1200.

The constraining members may be configured to maintain functional engagement or coupling between the delivery device 1500 and the leaflet frame subcomponent 1200 after deployment to facilitate in-situ nesting of the anchor frame subcomponent 1100 and the leaflet frame subcomponent 1200. In some such examples, the constraining members include loops of material (e.g., sutures, filaments, tethers or the like) having one or more portions that pass between the leaflet frame subcomponent interior surface 1206 and the leaflet frame subcomponent exterior surface 1208 by extending through the film disposed about the leaflet frame subcomponent 1200, as discussed above. Regardless, in various examples, withdrawing the delivery device 1500 proximally causes the leaflet frame subcomponent 1200 to translate proximally relative to the anchor frame subcomponent 1100 and to be nested within the anchor frame subcomponent 1100 (whether partially nested and only partially overlapping or completely nested and fully overlapping).

In some examples, the delivery device 1500 includes a plurality of independently movable components (e.g., the outer sheath 1501) that can be longitudinally advanced and retracted relative to one another. For instance, in some examples, a first moveable component (e.g., a first catheter or the outer sheath 1501) can be proximally withdrawn relative to the anchor frame subcomponent 1100 while maintaining a position of a second movable component (e.g., a second catheter) relative to the anchor frame subcomponent 1100. In some such examples, the first moveable component (e.g., the first catheter) may be coupled to the leaflet frame subcomponent 1200 by way of one or more constraining members (as discussed herein) such that proximally withdrawing the first movable component relative to the anchor frame subcomponent 1100 and the second movable component (e.g., the second catheter) causes the leaflet frame subcomponent 1200 to be withdrawn into the anchor frame subcomponent 1100 such that the leaflet frame subcomponent 1200 can be nested with the anchor frame subcomponent 1100.

In some examples, the second moveable component (e.g., the second catheter) may be coupled to the anchor frame subcomponent 1100 by way of one or more constraining members (as discussed herein) that maintaining a position of the second movable component relative to the anchor frame subcomponent 1100 as the first movable component (e.g., the first catheter) is proximally withdrawn relative to the second movable component the second movable component operates to maintain a position of anchor frame subcomponent 1100 such that the leaflet frame subcomponent 1200 can be nested therewith.

In some examples, one or more constraining members (e.g., tethers) extend between the leaflet frame subcomponent 1200 and the delivery device 1500. In some examples, the one or more tethers are coupled to the leaflet frame subcomponent 1200 such that as the delivery device 1500 is withdrawn, the leaflet frame subcomponent 1200 is proximally advanced relative to the anchor frame subcomponent 1100. In some examples, the one or more constraining members are woven through or otherwise disposed about one or more portions of the leaflet frame subcomponent 1200. For instance, in some examples, each of the constraining members forms a loop or similar feature extends about a portion of the leaflet frame subcomponent 1200. In some examples, one or more lock wires releasably secure the one or more tethers to the leaflet frame subcomponent 1200.

In some examples, in addition to proximally withdrawing or advancing the leaflet frame subcomponent 1200, the anchor frame subcomponent 1100 is secured against longitudinal translation during the nesting procedure. In some examples, longitudinal movement of the anchor frame subcomponent 1100 is arrested by the tissue engagement features 1118 of the anchor frame subcomponent 1100 engaging the tissue surrounding the prosthetic valve 1000. In some examples, the delivery device 1500 includes one or more arresting mechanisms that operate to minimize longitudinal movement of the anchor frame subcomponent 1100 during the nesting procedure. In some examples, the delivery device 1500 includes a pushing element that abuts one or more portions of the anchor frame subcomponent 1100 while the leaflet frame subcomponent is proximally advanced.

In terms of nesting during deployment, in various examples, the leaflet frame subcomponent 1200 is proximally advanced relative to the anchor frame subcomponent 1100 until the leaflet frame subcomponent 1200 becomes nested within the anchor frame subcomponent 1100. In various examples, unlike the predeployed and partially deployed configurations, in a nested configuration, the leaflet frame subcomponent inlet end 1202 of the leaflet frame subcomponent 1200 is positioned proximal to the anchor frame subcomponent outlet end 1104 of the anchor frame subcomponent 1100. For reference, FIG. 6G illustrates the leaflet frame subcomponent 1200 nested within the anchor frame subcomponent 1100 such the leaflet frame subcomponent inlet end 1202 (FIG. 2A) of the leaflet frame subcomponent 1200 is positioned proximal to the anchor frame subcomponent outlet end 1104 (FIG. 2A) of the anchor frame subcomponent 1100 (though such an arrangement is not always the case, and partial overlap of the components—such as the leaflet frame subcomponent 1200 projecting from the anchor frame subcomponent 1100 following nested—is contemplated).

FIGS. 6D and 6E illustrate the anterior leaflet (AL) after being cut by the cutting element 1001. As illustrated in FIG. 6F, when the prosthetic valve 1000 is deployed, the anterior leaflet of the mitral valve is deflected toward the left ventricular outflow tract if not cut as shown. In various examples, if not cut as illustrated and described herein, the deflected anterior leaflet (AL) of the mitral valve will extend into the left ventricle to cause a narrowing of, a restriction of, and/or an obstruction of the left ventricular outflow tract (LVOT). This narrowing, restriction, and/or obstruction of the left ventricular outflow tract can lead to a number of health risks and complications as those of skill in the art will appreciate. By providing a prosthetic valve and method of implanting the same that operates to cut at least a portion of the anterior leaflet (AL) of the mitral valve to prevent the anterior leaflet (AL) from obstructing or otherwise interfering with the left ventricular outflow tract (LVOT), the prosthetic valve 1000 of the present application operates to minimize or eliminate the risks associated with a narrowing, restriction, and/or obstruction of the left ventricular outflow tract.

FIG. 6G is an illustration of the prosthetic valve 1000 in a fully deployed configuration wherein the anchor frame subcomponent 1100 and the leaflet frame subcomponent 1200 are nested. As shown, the anterior leaflet (AL) of the mitral valve is at least partially cut by the cutting element 1001 of the transcatheter cutting system 100. In some examples, the prosthetic valve 1000 is fully deployed and operational upon the interlock features 1120 coupling together the anchor frame subcomponent 1100 and the leaflet frame subcomponent 1200. As discussed above, the interlock features 1120 are operable to adopt an engaged configuration wherein they engage the leaflet frame subcomponent 1200 and minimize relative axial translation between the anchor frame subcomponent 1100 and the leaflet frame subcomponent 1200 upon the leaflet frame subcomponent 1200 being proximally advanced a designated amount relative to the anchor frame subcomponent 1100.

Figure 7:
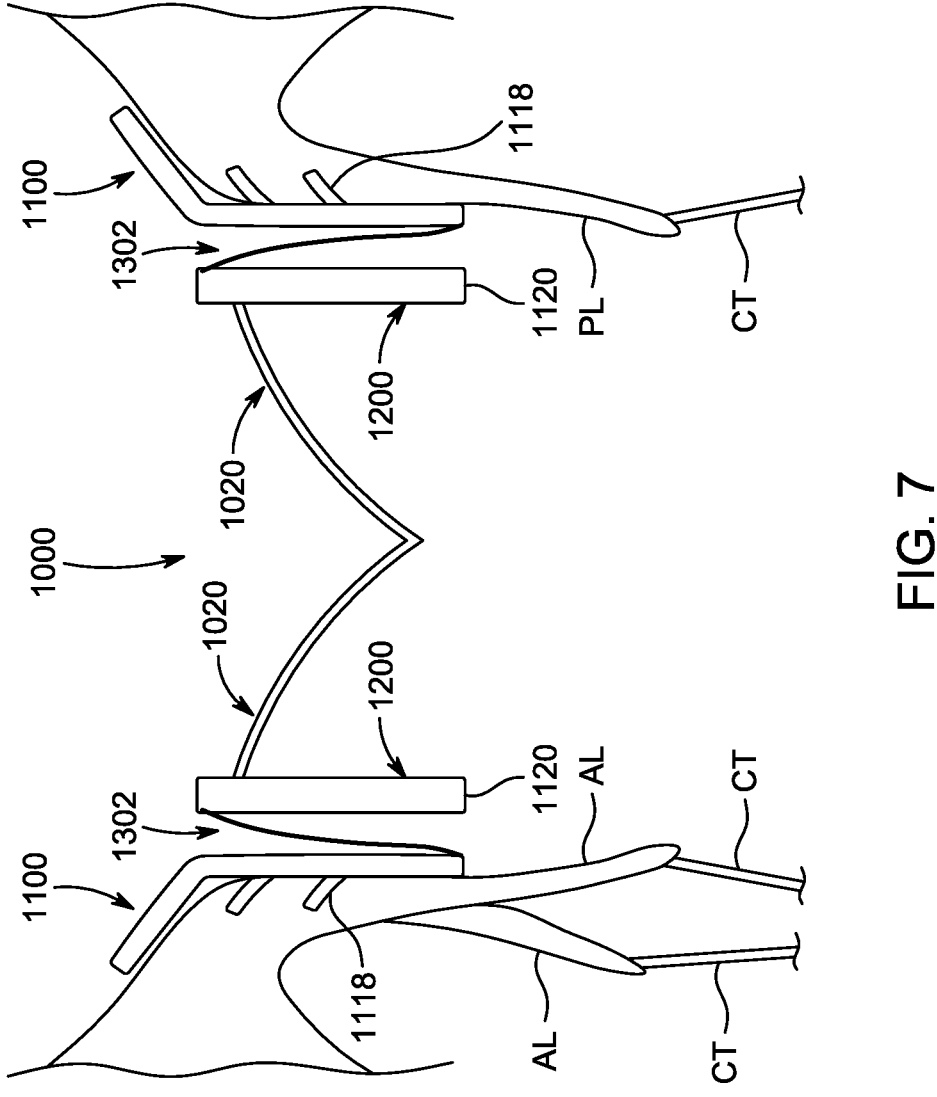
FIG. 7 is a sectional view of a prosthetic valve deployed in a valve orifice, according to some embodiments.

FIG. 7 is a cross-sectional view of the prosthetic valve 1000 as fully deployed (e.g., similar to the configuration shown in FIG. 6G) and in an operational configuration. The posterior and anterior leaflets of the valve are coupled to papillary muscles (PM) within the left ventricle via the chordae tendineae (CT). Generally, the chordae tendineae are inelastic tendons attached at one end to papillary muscles in the left ventricle, and at the other to the valve cusps of the posterior and anterior leaflets. As shown in FIG. 7, the anchor frame subcomponent 1100 and the leaflet frame subcomponent 1200 are nested together such that the leaflet frame subcomponent 1200 is coaxially received within the anchor frame subcomponent interior region 1110 (FIG. 4B) of the anchor frame subcomponent 1100. As shown, the anterior leaflet (AL) of the mitral valve is cut such that the anterior leaflet does not block the left ventricular outflow tract (LVOT) after deployment of the prosthetic valve 1000.

In various examples, the interstage 1300 extends between the anchor frame subcomponent 1100 and the leaflet frame subcomponent 1200 in the nested configuration (e.g., as shown in FIG. 7). In various examples, in addition to coupling the anchor frame subcomponent 1100 with the leaflet frame subcomponent 1200, the interstage 1300 operates to obstruct undesirable retrograde flow through the prosthetic valve 1000. In particular, the film extending between the anchor frame subcomponent 1100 and the leaflet frame subcomponent 1200 in the nested configuration operates to prevent retrograde flow through the annular region defined between the anchor frame subcomponent 1100 and the leaflet frame subcomponent 1200. Thus, while the leaflets of the prosthetic valve 1000 are configured to close and prevent retrograde flow through the prosthetic valve 1000 (and an interior region of the leaflet frame subcomponent in particular), the interstage 1300 extending between the anchor frame subcomponent 1100 and the leaflet frame subcomponent 1200 also operates to minimize or prevent unintended retrograde flow through the prosthetic valve 1000.

Additionally, as shown in FIG. 7, the interlock features 1120 of the anchor frame subcomponent 1100 engage the leaflet frame subcomponent 1200 and operate to maintain a relative position of the leaflet frame subcomponent 1200 with the anchor frame subcomponent 1100. In various examples, the interlock features 1120 of the anchor frame subcomponent 1100 operated to minimize the potential for the leaflet frame subcomponent 1200 to dislodge distally from its nested position within the anchor frame subcomponent 1100. In various examples, the interlock features 1120 extend from the anchor frame subcomponent 1100 to a position distal to one or more of the leaflet frame subcomponent outlet end 1204 of the leaflet frame subcomponent 1200 and the leaflet frame subcomponent inlet end 1202 of the leaflet frame subcomponent 1200. That is, in some examples, the interlock features 1120 extend to and engage a portion of the leaflet frame subcomponent 1200 between the leaflet frame subcomponent inlet end 1202 and the leaflet frame subcomponent outlet end 1204. In other examples, in the nested configuration, the interlock features 1120 extend to a position distal to the leaflet frame subcomponent outlet end 1204 of the leaflet frame subcomponent 1200.

Additionally, as shown in FIG. 7, the tissue engagement features 1118 of the anchor frame subcomponent 1100 extend away from the anchor frame subcomponent 1100 and engage the tissue of the valve orifice surrounding the prosthetic valve 1000. In some examples, the tissue engagement features 1118 are configured to penetrate the tissue or otherwise embed within the tissue. In various examples, this interaction of the tissue engagement features 1118 of the anchor frame subcomponent 1100 with the tissue surrounding the prosthetic valve 1000 operates to secure the anchor frame subcomponent 1100 (and thus the leaflet frame subcomponent 1200) to the tissue (e.g., the valve orifice).

The anchor frame subcomponent inlet end 1102 of the anchor frame subcomponent 1100 illustrated in FIG. 7 is flared radially outward and is situated adjacent to and in abutment with the valve orifice, as shown. In some examples, such a configuration provides that the anchor frame subcomponent inlet end 1102 of the anchor frame subcomponent 1100 obstructs or otherwise limits the extent to which the anchor frame subcomponent 1100 is operable to extend through the valve. For instance, in the case of a mitral valve replacement, such the flared end at the anchor frame subcomponent inlet end 1102 can help limit the extent to which the anchor frame subcomponent 1100 can be advanced through the natural mitral valve orifice and into the left ventricle. In some examples, the flared configuration of the anchor frame subcomponent inlet end 1102 additionally operates to minimize the potential for the anchor frame subcomponent 1100 to migrate distally.

While the embodiments and examples illustrated and described above pertain to trans-septal delivery, it should be appreciated that a variety of additional well-known delivery procedures can be utilized without departing from the spirit or scope of the present application. Additional non-limiting delivery procedures include trans-apical, left atriotomy, and trans-aortic. Generally, regardless of the particular delivery procedure, those of skill should appreciate that after deploying the prosthetic valve 1000, the leaflet frame subcomponent 1200 and the anchor frame subcomponent 1100 are nested by proximally advancing the leaflet frame subcomponent 1200 relative to the anchor frame subcomponent 1100.

In various examples, a prosthetic valve and its associated delivery system is configured to enable continued valve functionality during the deployment procedure. In various examples, during a prosthetic valve deployment procedure to replace a damaged valve, the valve and valve orifice are temporarily obstructed by the prosthetic valve and the delivery device. In some instances, such obstructions occur prior to the prosthetic valve being deployed and becoming operational (e.g., prior to nesting the anchor frame subcomponent and the leaflet frame subcomponent). Accordingly, in various examples, the prosthetic valves of the present disclosure may additionally include one or more features that are configured to permit fluid to flow through or around the prosthetic valve during the implantation procedure, prior to the prosthetic valve becoming fully operational (e.g., prior to nesting the anchor frame subcomponent and the leaflet frame subcomponent).

For example, and with reference to FIGS. 8A and 8B, a prosthetic valve 2000 includes one or more flow enabling features 2350 formed in the interstage 1300 extending between the anchor frame subcomponent 2100 and the leaflet frame subcomponent 2200. As shown in FIGS. 8A and 8B, the flow enabling features 2350 include an aperture 2352 and a flap 2354 that operate to enable antegrade flow through the prosthetic valve 2000 prior to the anchor frame subcomponent 2100 and the leaflet frame subcomponent 2200 being nested together (i.e., while the anchor frame subcomponent 2100 and the leaflet frame subcomponent 2200 are longitudinally offset as illustrated and described herein). The flap 1354 is oversized relative to the aperture 2352 to restrict or minimize retrograde flow through the one or more flow enabling features 2350 while permitting antegrade flow. In some examples, the body 1001*a* of the cutting element 1001 and/or the protective cover 1001*b* may pass through the aperture 2352.

FIG. 8C is another embodiment of the interstage 1300 as shown coupled to the leaflet frame subcomponent 1200 and anchor frame subcomponent 1100. In accordance with this embodiment, the interstage 1300 is a double layer construct (e.g., of film), including an inner layer 1304 that defines an inner surface of the conduit 1302 and an outer layer 1306 that defines an outer surface of the conduit 1302 as viewed in the partially deployed position. The inner layer 1304 and the outer layer 1306 are not coupled at least between one or more inner apertures 1312 and one or more outer apertures 1310 so as to define a flow space 1320 therebetween.

FIG. 6H is a schematic view showing the prosthetic valve 1000 in a constrained state on a delivery catheter 1508, with the anchor frame subcomponent 1100 positioned within the native valve orifice 1342. As shown in FIG. 6H, when the prosthetic valve 1000 is constrained onto a delivery catheter 1508, blood flow is able to pass between the device and the tissue 1340. The cutting element 1001 is not shown in FIG. 6H. As previously referenced, the cutting element 1001 may pass through a portion of the prosthetic valve 1000 as show in FIGS. 6H and 6I for illustrative purposes.

As shown in FIG. 6I, when the anchor frame subcomponent 1100 is deployed against the native valve orifice 1342, blood is permitted to flow through one or more inner apertures 1312, the flow space 1320, and one or more outer apertures 1310, in between the inner layer 1304 and outer layer 1306, in the forward flow direction but is prevented from flowing back in a retrograde direction. When the leaflet frame subcomponent 1200 is unconstrained and expands to the deployed diameter, the blood may continue to flow through the one or more inner apertures 1312, the flow space 1320, and one or more outer apertures 1310 as before.

Figure 6J:
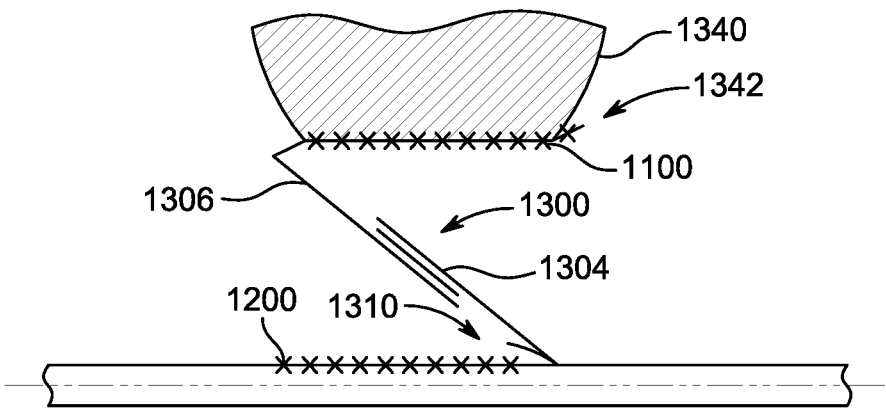
Figure 6K:
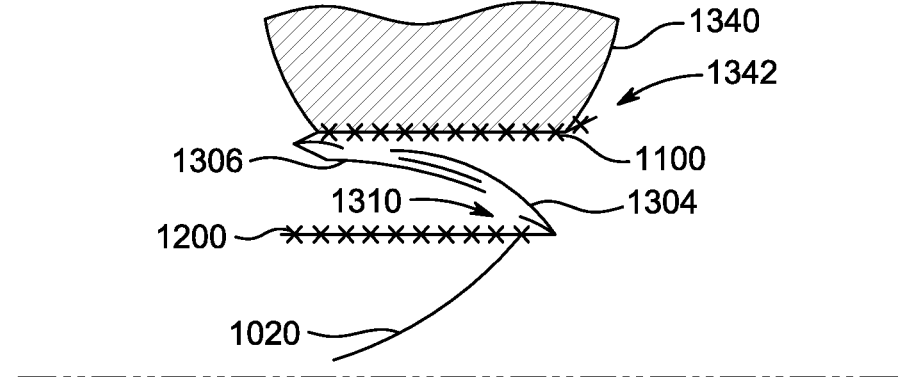

As shown in FIG. 6J, the leaflet frame subcomponent 1200 is translated into the anchor frame subcomponent 1100, and as shown in FIG. 6K with the leaflet frame subcomponent 1200 expanded into its final deployed configuration, whereby everting or folding/rotating the interstage 1300, the inner layer 1304 and the outer layer 1306 are caused to come together under fluid pressure narrowing the flow space 1320 and closing the one or more inner apertures 1312 against the outer layer 1306 and closing the one or more outer apertures 1310 against the inner layer 1304, preventing flow therethrough. In this example, blood profusion may be maintained during substantially the entire deployment process.

Interlock Features

As mentioned above, in various examples, the prosthetic valve 1000 includes interlock features 1120 that operate to maintain a coupling between the leaflet frame subcomponent 1200 and the anchor frame subcomponent 1100. In some examples, the prosthetic valve 1000 additionally or alternatively includes one or more features that extend between the anchor frame subcomponent 1100 and the leaflet frame subcomponent 1200. For example, as shown in FIGS. 9A and 9B, the prosthetic valve 1000 includes a plurality of interconnecting struts 1700 that extend between the anchor frame subcomponent 1100 and the leaflet frame subcomponent 1200.

FIG. 9A shows the prosthetic valve 1000 prior to telescoping or nesting of the anchor frame subcomponent 1100 and the leaflet frame subcomponent 1200. FIG. 9B shows the prosthetic valve 1000 with the anchor frame subcomponent 1100 and the leaflet frame subcomponent 1200 in a nested configuration. As shown in FIGS. 9A and 9B, the interconnecting struts 1700 are configured to evert along with the interstage 1300 as the leaflet frame subcomponent 1200 is telescoped or nested with the anchor frame subcomponent 1100. The interconnecting struts 1700 optionally provide stiffening bias such that, following nesting, the interconnecting struts 1700 resist the movement of the leaflet frame subcomponent 1200 from the nested position.

In accordance with other examples, as shown in FIGS. 9C and 9D, the prosthetic valve 1000 includes one or more nesting retention elements 1330 in the form of a sinuous element 1702 that extends between the anchor frame subcomponent 1100 and the leaflet frame subcomponent 1200 but does not couple directly therewith. The sinuous element 1702 can similarly provide stiffening bias to the interstage 1300. FIG. 9C shows the prosthetic valve 1000 prior to telescoping or nesting of the anchor frame subcomponent 1100 and the leaflet frame subcomponent 1200. FIG. 9D shows the prosthetic valve 1000 with the anchor frame subcomponent 1100 and the leaflet frame subcomponent 1200 in a nested configuration. As shown in FIGS. 9C and 9D, the sinuous element 1702 is configured to evert along with the interstage 1300 as the leaflet frame subcomponent 1200 is telescoped or nested with the anchor frame subcomponent 1100. The sinuous element 1702 optionally provides stiffening bias such that, following nesting, the sinuous element 1702 resists the movement of the leaflet frame subcomponent 1200 from the nested position.

Figures 9E, 9F:
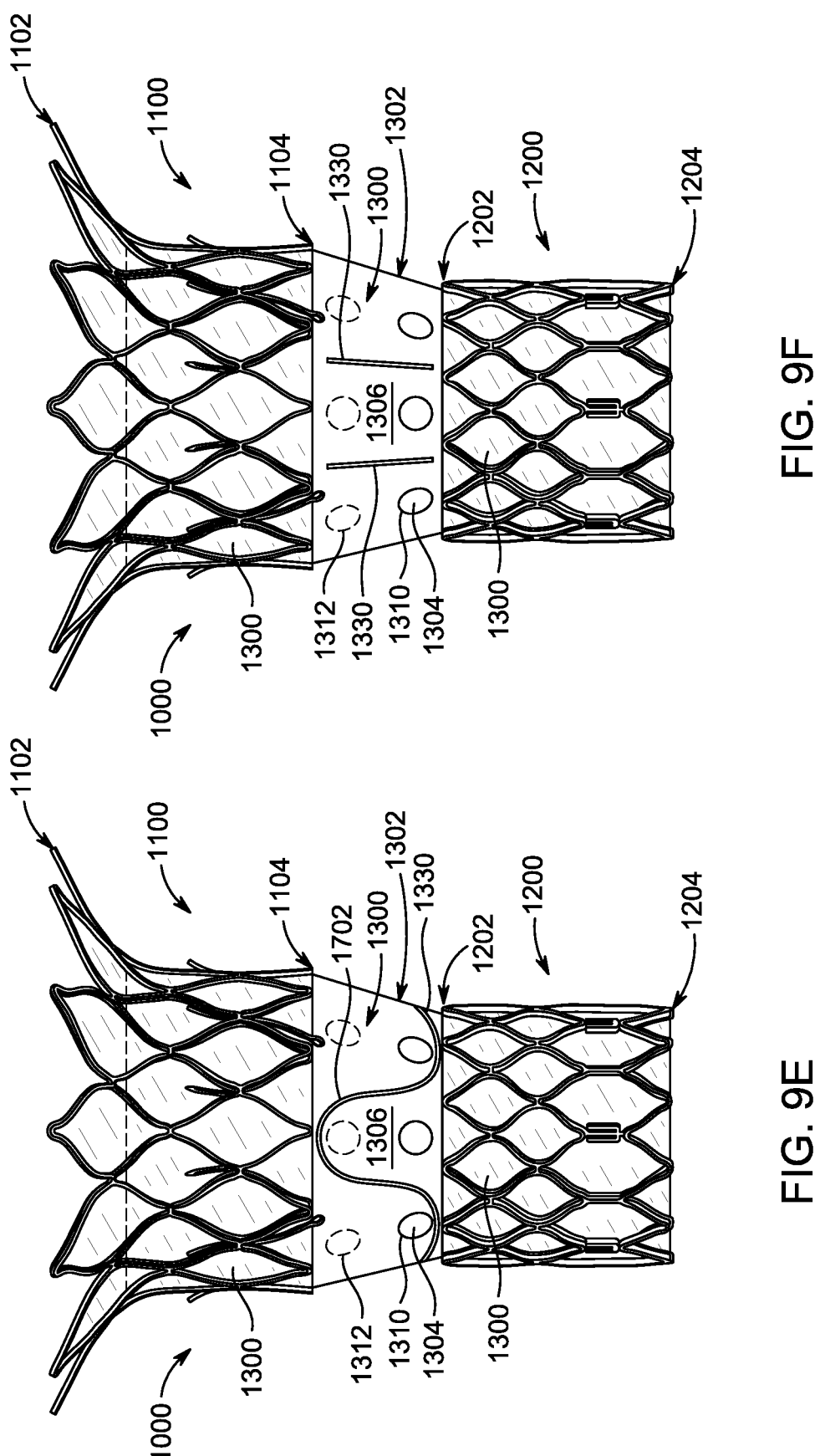
FIGS. 9E and 9F show additional configurations of nesting retention elements and flow enabling features of a prosthetic valve, according to some embodiments.

FIGS. 9E and 9F show of nesting retention elements 1330. In accordance with some examples, the nesting retention elements 1330 may be one or more elongated elements that help retain the interstage 1300 in the nested configuration following nesting. In FIG. 9E, the one or more nesting retention elements 1330 have a serpentine or sinuous configuration, whereas in FIG. 9F, the nesting retention elements 1330 are straight and generally aligned with the longitudinal axis of the prosthetic valve 1000. In some examples, the nesting retention elements 1330 are positioned between the locations of two neighboring apertures of the inner apertures 1312 and/or between two neighboring apertures of the outer apertures 1310 at the interstage 1300.

In accordance with an embodiment, the nesting retention elements 1330 are caused to evert during the deployment process of translating the leaflet frame subcomponent 1200 into the anchor frame subcomponent 1100. The nesting retention elements 1330 are provided with a predetermined stiffness or other property sufficient to permit eversion during deployment but not under normal biological forces. In accordance with some embodiments, the nesting retention elements 1330 are sized such that, when the anchor frame subcomponent 1100 is expanded and the leaflet frame subcomponent is compressed, the nesting retention elements 1330 are able to rotate lengthwise from a forward-facing orientation to a backward facing orientation. When the leaflet frame subcomponent 1200 is expanded, the nesting retention elements 1330 have a profile or length that prevents the nesting retention elements 1330 from rotating or flipping back to a forward-facing orientation under operating conditions.

Leaflets

For simplicity of discussion, when referring to materials from which leaflets are made, it is appreciated that the same material may also be used to make one or more portions or an entirety of a leaflet construct. Therefore, in this context, the description of leaflet materials applies to options that may be employed for one or more individual leaflets, and also one or more portions of a leaflet construct, as well as for an entirety of the leaflet construct. In the examples that follow, the leaflets that are formed with the leaflet materials described are flexible and are comprised of flexible materials.

In some examples, each of the one or more leaflets 1210, such as a plurality of the leaflets 1210 forming the leaflet construct 1211, may be formed of a natural material, such as repurposed tissue, including bovine tissue, porcine tissue, or the like.

In accordance with various embodiments, each leaflet and/or each leaflet of the plurality of leaflets forming a leaflet construct, may be flexible and synthetic in that the leaflets comprise one or more biocompatible materials that are not of a biological source and that are sufficiently compliant and strong for the particular purpose, such as a biocompatible polymer. In some embodiments, the leaflets comprise a membrane, such as ePTFE, that is combined with an elastomer or elastomeric material, such as a fluoroelastomer, to form a composite material, as disclosed herein. It will be appreciated that while various examples are discussed with regard to leaflets 1210 and/or leaflet constructs 1211, the various examples and embodiments discussed herein may be universally applied across each of the leaflet constructs and/or the various components of the leaflet constructs discussed herein.

In some examples, the one or more leaflets 1210 and/or leaflet construct 1211 including one or more leaflets 1210 can be made by starting from a cylinder of polymer and/or composite material that has been cut into a shape like that shown in FIG. 3B. In some other examples, a single or plurality of leaflets 1210 are made from a flat sheet of polymer and/or composite material. In some examples, a plurality of leaflets 1210 are subsequently coupled together into an annular shape. In some other examples, the leaflet construct 1211 and/or the leaflets 1210 may be formed by other methods, such as, but not limited to, compression and injection molding processes.

Suitable leaflet materials include natural materials (e.g., repurposed tissue, including bovine tissue, porcine tissue, or others), synthetic materials (e.g., biocompatible polymers), and combinations of natural and synthetic materials. Suitable leaflet forming processes include, but are not limited to, casting, molding, extruding, wrapping, coating, imbibing, laminating, combinations thereof and others.

Suitable synthetic leaflet materials include urethanes, silicones (e.g., organopolysiloxanes), copolymers of silicon-urethane, styrene/isobutylene copolymers, polyisobutylene, polyethylene, polyethylene-co-poly(vinyl acetate), polyester copolymers, nylon copolymers, fluorinated hydrocarbon polymers, fluoroelastomers (e.g., copolymers of tetrafluoroethylene and perfluoromethyl vinyl ether (TFE/PMVE copolymer) and (per)fluoroalkylvinylethers (PAVE)), and copolymers and/or mixtures of each of the foregoing and composite materials made therewith. Suitable biocompatible polymers, such as one or more of those described above, may exhibit the physical properties of an elastomer, elastomeric, or non-elastomeric material.

Leaflet materials may include composite materials. Suitable composite leaflet materials include, but are not limited to, one or more membranes combined with one or more polymers. In accordance with some examples, the composite material comprises a membrane (e.g., porous synthetic polymer membrane) by weight in a range of about 10% to about 90%. The one or more polymers may be coatings or layers on the one or more membranes and/or may be imbibed into the one or more membranes (e.g., where the one or more membranes include a microporous structures), for example. Composite materials may include additional or alternative components, such as but not limited to, inorganic fillers, therapeutic agents, radiopaque markers, and others. In some examples, composite leaflet material includes at least one porous synthetic polymer membrane layer having a plurality of pores and/or spaces and a polymer that is an elastomer and/or an elastomeric material filling the pores and/or spaces. In other examples, the composite leaflet material further comprises a layer or coating of elastomer and/or elastomeric material and/or non-elastomeric material on one or both sides of the composite leaflet material.

A membrane that is suitable for use in composite leaflet materials includes, but is not limited to, porous synthetic polymer membranes, such as microporous polyethylene and expanded fluoropolymer membranes such as expanded polytetrafluoroethylene (ePTFE). Such membranes can comprise PTFE homopolymer, blends of PTFE, expandable modified PTFE and/or expanded copolymers of PTFE. As referenced, the membranes may have a microporous structures (e.g., such as ePTFE membranes including a matrix of fibrils defining a plurality of spaces within the matrix).

Suitable polymers of composite leaflet materials include polymers that exhibit elastomer, elastomeric, and/or non-elastomeric material properties. Such polymers may include elastomers and elastomeric materials, such as fluoroelastomers. Examples of suitable polymers include TFE-PMVE copolymers, which may exhibit elastomer, elastomeric, and/or non-elastomeric material properties based on the wt % or mol % of the respective polymers. By way of example of a suitable elastomer, TFE/PMVE copolymer is an elastomer when comprising essentially of between 60 and 20 weight percent tetrafluoroethylene and respectively between 40 and 80 weight percent perfluoromethyl vinyl ether. By way of example of a suitable elastomeric material, TFE/PMVE copolymer is an elastomeric material when comprising essentially of between 67 and 61 weight percent tetrafluoroethylene and respectively between 33 and 39 weight percent perfluoromethyl vinyl ether. By way of example of a suitable non-elastomeric material, TFE/PMVE copolymer is a non-elastomeric material when comprising essentially of between 73 and 68 weight percent tetrafluoroethylene and respectively between 27 and 32 weight percent perfluoromethyl vinyl ether. In the foregoing examples, the TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the composite leaflet material includes an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces. In other examples the leaflet is an ePTFE membrane having been imbibed with TFE-PMVE copolymer comprising from about 70 to about 61 weight percent tetrafluoroethylene and respectively from about 33 to about 39 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces. As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer made from porous ePTFE membrane.

The expanded fluoropolymer membrane, used to form some of the composites described, can comprise PTFE homopolymer. In alternative embodiments, blends of PTFE, expandable modified PTFE and/or expanded copolymers of PTFE can be used.

In addition to expanded fluoropolymer, other biocompatible synthetic polymers may be suitable for use as a porous membrane. As provided below, embodiments comprising microporous polyethylene are provided as a biocompatible polymer suitable for the particular purpose.

Tissue Ingrowth

In various embodiments, one or more portions of the prosthetic valve 1000 are configured to promote tissue ingrowth. Any portion of the anchor frame subcomponent 1100, leaflet frame subcomponent 1200, interstage 1300, the leaflets 1210 of the leaflet construct 1211, or any other feature or portion of the prosthetic valve 1000 may be constructed in a manner that promotes tissue ingrowth, whether over the entire surface(s) or portion(s) thereof. Moreover, such ingrowth may be selective in depth in that growth may by promoted only into the surface of materials, without growing entirely through the material forming the above noted-features. A variety of membranes, films, coatings, fabrics, or other material configurations may be implemented. Some nonlimiting examples of materials that can be applied to portions of the prosthetic valve 1000 to promote tissue ingrowth include properly configured expanded polytetrafluoroethylene (ePTFE), such as an ePTFE membrane and/or polyethylene terephthalate fabric (e.g., Dacron fabric).

In various embodiments, one or more portions of the leaflet frame subcomponent 1200 may be suitable for promoting tissue ingrowth. For example, the leaflet frame 1201 can be wrapped, covered, or otherwise coupled to a cover material suitable for promoting tissue ingrowth. In various examples, such tissue ingrowth promoting materials can be applied to leaflet frame entirely, or to less than all of the leaflet frame as desired. Similarly, one or more portions of the anchor frame subcomponent 1100 may be suitable for promoting tissue ingrowth. For example, the anchor frame 1101 can be wrapped, covered, or otherwise coupled to a cover material suitable for promoting tissue ingrowth. In various examples, such tissue ingrowth promoting materials can be applied to leaflet frame entirely, or to less than all of the leaflet frame 1201 and/or the anchor frame 1101 as desired. For example, suitable materials for promoting tissue ingrowth could be coupled to the inner and/or outer surfaces of the leaflet frame 1201 and/or the anchor frame 1101.

In some embodiments, one or more of the leaflets 1210 may be constructed to encourage tissue ingrowth and proliferation across one or more discrete regions, portions, or sections of one or more of the materials forming the one or more leaflets 1210, or alternatively across an entirety of one or more of the materials forming each of the one or more leaflets 1210. Tissue ingrowth and proliferation may be promoted on an outflow side or surface of one or more of the leaflets 1210, and/or on an inflow side or surface of the leaflets 1210, and/or within one or more materials forming the leaflets.

According to some examples, tissue ingrowth is facilitated by incorporating one or more tissue ingrowth layers into the leaflets 1210 to permit selective growth into one or more surfaces of the one or more leaflets 1210. In some examples, one or more non-ingrowth layers are also incorporated to prevent ingrowth through an entire thickness of the leaflet material, or through unwanted portions of the leaflet. In various examples, material underlying the tissue ingrowth material (e.g., one or more layers) may inhibit tissue ingrowth to limit depth of tissue ingrowth into the leaflet material. Similar concepts may be applied to promote selective tissue ingrowth into the other portions of the prosthetic valve 1000 as referenced above. In other words, any portion of the prosthetic valve 1000 may benefit from incorporation of tissue ingrowth layer(s), as well as one or more non-ingrowth layers as desired.

In some examples, selective promotion of tissue ingrowth into tissue ingrowth layers is facilitated by selectively imbibing, such as with one or more fluoroelastomers, one or more portions of the materials forming the one or more leaflets 1210. Reference to "selectively imbibing" is referring to the act of imbibing a porous material with a filling material at selected portions of the porous material or to a lesser degree leaving a degree of porosity of the porous material. Similar concepts may be applied to promote selective tissue ingrowth into the other portions of the prosthetic valve 1000 as referenced above.

In various embodiments, tissue ingrowth layer materials include expanded fluoropolymer membranes, which may comprise a plurality of spaces within a matrix of fibrils, and are suitable for promoting and supporting the ingrowth of tissue. Other nonlimiting example materials include other biocompatible porous materials such as knit PTFE. However, rather than including a membrane or carrier, in some examples tissue ingrowth layers may be realized in the form of one or more coatings applied to an underlying material.

Though in some examples tissue ingrowth layers include expanded fluoropolymer made from porous ePTFE membranes, it is appreciated that tissue ingrowth layers may be formed from a number of different types of membranes, including other fluoropolymer membranes, and other biocompatible porous materials such as knit PTFE. For instance, suitable expandable fluoropolymers can comprise PTFE homopolymer. In some examples, tissue ingrowth layers can be formed from copolymers of hexafluoropropylene and tetrafluoroethylene, such as fluorinated ethylene propylene (FEP). In some examples, blends of PTFE, expandable modified PTFE and/or expanded copolymers of PTFE can be used. It will thus be appreciated that tissue ingrowth layers may be formed from a variety of different polymeric materials, provided they are biocompatible and possess or are modified to include a suitable microstructure suitable for promoting or supporting tissue ingrowth. In various non-limiting examples, the tissue ingrowth layers may range in thickness from between one micron and four hundred microns, for example, depending on the selected material.

In some examples, polymeric materials for tissue ingrowth layers may include one or more naturally occurring and/or one or more artificially created pores, reliefs, channels, and/or predetermined surface topology, suitable for supporting tissue ingrowth. Other biocompatible porous materials which can be suitable for use forming tissue ingrowth layers include but are not limited to groups of urethanes, fluoropolymers, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

While the above-discussed tissue ingrowth layers may generally include membranes, films, knits, or other structures that are bonded, applied, or otherwise attached to underlying layers, in some examples the tissue ingrowth layers may be applied to underlying layers in the form of one or more coatings. In some such examples, coherent irregular networks are distributed or deposited onto one or more portions, regions, sections, areas, or zones of underlying layers. In some examples, such coherent irregular networks are applied to one or more portions of one or more underlying layers to create a surface texture suitable for supporting the ingrowth and proliferation of tissue, as those of skill will appreciate.

In some examples, coherent irregular networks may be selectively applied to one or more discrete or designated sections, portions, or regions of underlying material. In some such examples, the coherent irregular network is applied to the designated areas by masking or otherwise covering those portions of the underlying material where ingrowth of tissue is undesirable.

In various examples, to achieve layers that promotes or otherwise accommodates ingrowth and proliferation of tissue, expanded fluoropolymer membranes may be selectively imbibed, such as with one or more fluoroelastomers, such that the expanded fluoropolymer membrane includes one or more discrete portions, regions, sections, zones, or areas that are free of or are not otherwise imbibed with the elastomeric filler material (or at least are not filled to the extent that the elastomeric filler material operates to prevent tissue ingrowth).

While the above discussed embodiments and examples include applying tissue ingrowth layers to one or more portions of one or more surfaces of an underlying material, or selectively imbibing one or more portions of one or more sides of a membrane of an underlying material with a filler material, it is appreciated that, in various examples, tissue ingrowth layers may be constructed by both imbibing one or more portions of a membrane forming an underlying material and applying a tissue ingrowth layers to the selectively imbibed underlying material. In various examples, the imbibing material, or filler material, may be varied within tissue ingrowth layers. That is, in some examples, a first portion, area, region, section, or zone of membrane may be imbibed with a first filler material while a second portion, area, region, section, or zone of the membrane may be imbibed with a second filler material.

Delivery Device

As discussed above, in various examples, the prosthetic valve 1000 is loaded on a delivery device 1500 in a pre-deployed configuration with the anchor frame subcomponent 1100 and the leaflet frame subcomponent 1200 being longitudinally offset from one another (e.g., arranged in series). In various examples, as mentioned above, one or more constraining members releasably and independently couple the leaflet frame subcomponent 1200 and the anchor frame subcomponent 1100 to the delivery device 1500. In various examples, as discussed in greater detail below, the one or more constraining members can be selectively released from the leaflet frame subcomponent 1200 and the anchor frame subcomponent 1100 to facilitate in-situ nesting of the anchor frame subcomponent 1100 and the leaflet frame subcomponent 1200. In some examples, one or more of the constraining members include one or more portions that may be woven through the film(s) disposed about the leaflet frame subcomponent 1200 and the anchor frame subcomponent 1100, such that a longitudinal actuation of the delivery device 1500 is transferrable to one or more of the leaflet frame subcomponent 1200 and the anchor frame subcomponent 1100 via the one or more constraining members.

Figure 10:
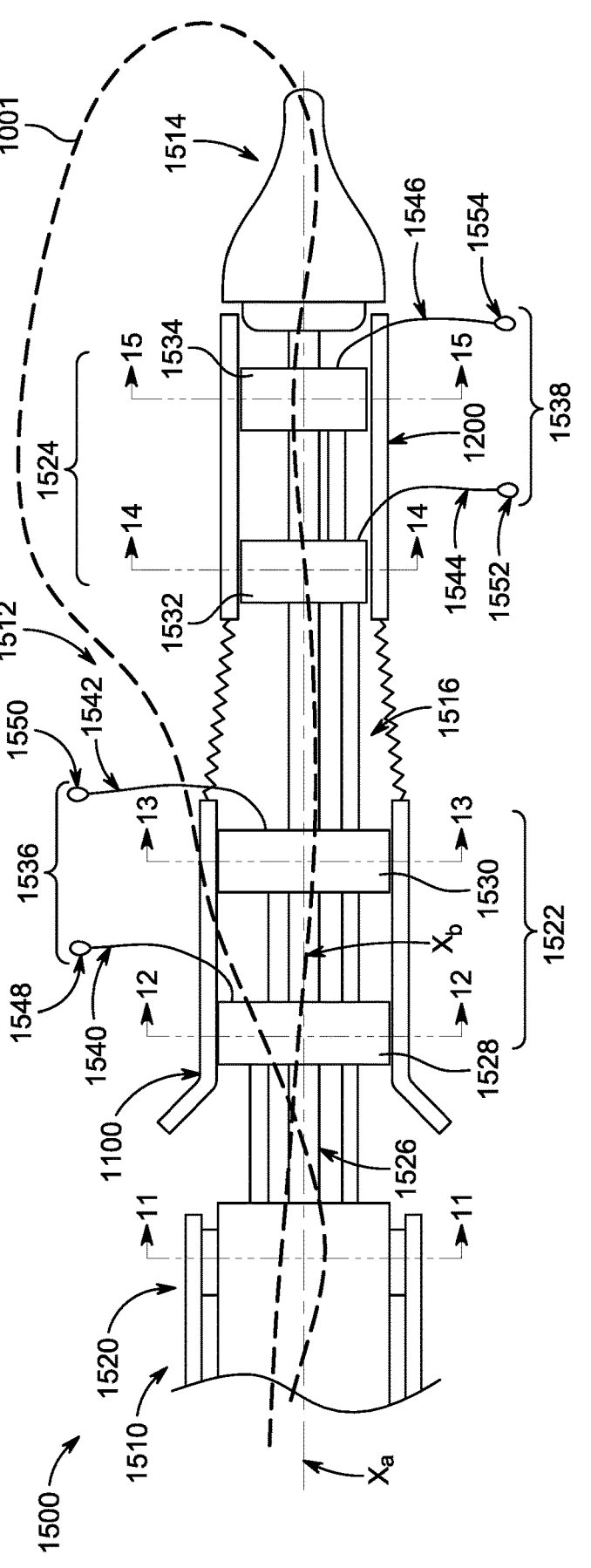
FIG. 10 shows a longitudinal section of a delivery device coupled to a prosthetic valve, according to some embodiments.

FIG. 10 is a side view of a delivery device 1500, according to some embodiments. As shown, the delivery device 1500 includes a body portion 1510, a support portion 1512, a tip portion 1514, a plurality of constraints 1516. In various examples, the delivery device 1500 further includes a plurality of locking members 1518 (see, e.g., FIG. 16). The body portion 1510 defines a central longitudinal axis Xa and has a proximal section (not shown) and a distal section 1520. The body portion 1510 is of suitable length for a user (not shown) to manipulate the delivery device 1500 from a location outside the body of a patient into which the prosthetic valve 1000 is being implanted. Generally, the body portion 1510 is of sufficient flexibility, length, and column strength such that it is suitable for traversing the vasculature or other bodily lumens and conduits within a patient (not shown). As shown, the cutting element 1001 may pass through the delivery device 1500 and/or the prosthetic valve 1000, sch that the cutting element 1001 is coupled to the respective delivery device 1500 and/or prosthetic valve 1000.

Figures 11, 12, 13, 14, 15:
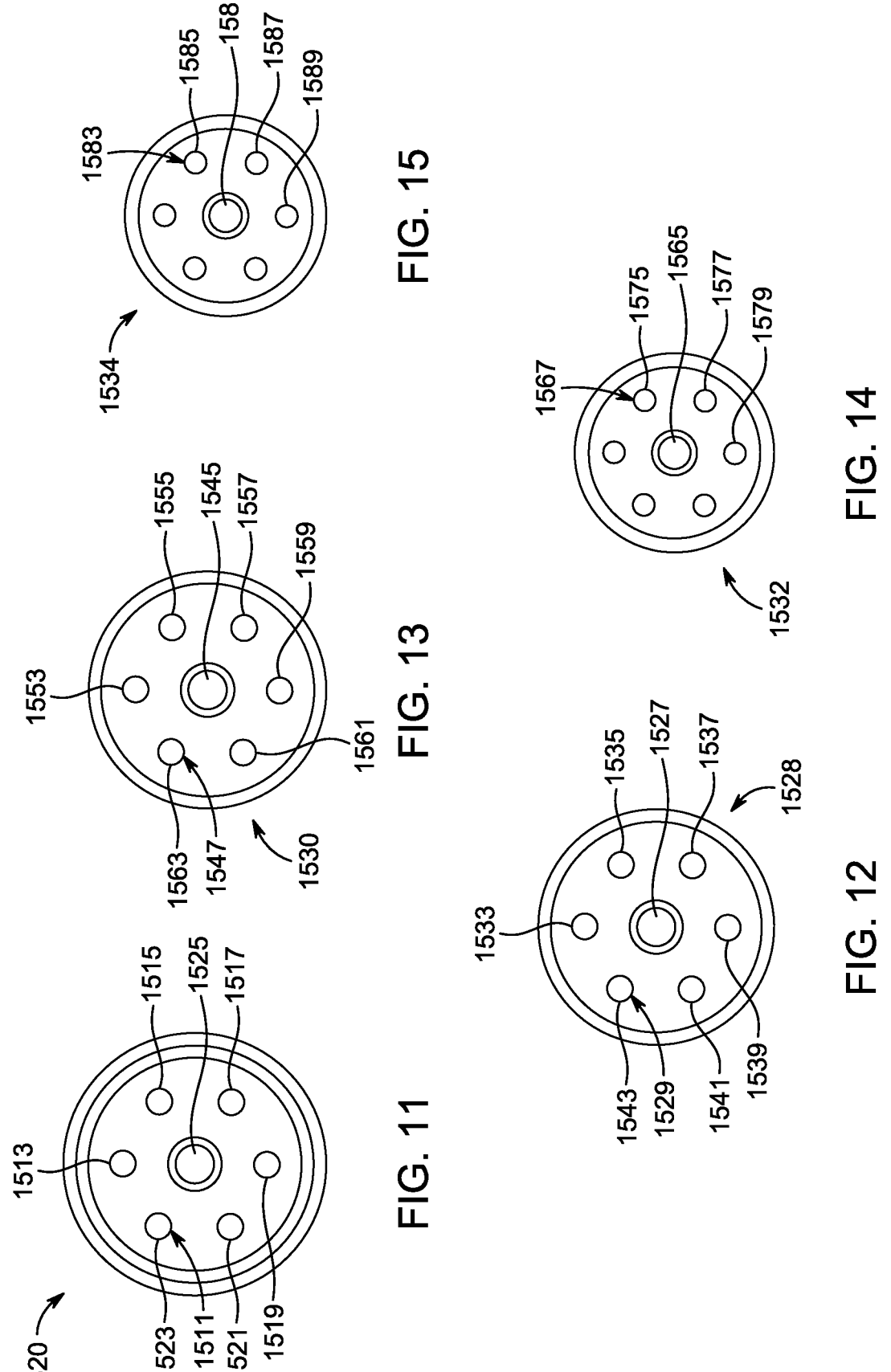
FIG. 11 shows a transverse section taken along line 11-11 in FIG. 10, according to some embodiments.
FIG. 12 shows a transverse section taken along line 12-12 in FIG. 10, according to some embodiments.
FIG. 13 shows a transverse section taken along line 13-13 in FIG. 10, according to some embodiments.
FIG. 14 shows a transverse section taken along line 14-14 in FIG. 10, according to some embodiments.
FIG. 15 shows a transverse section taken along line 15-15 in FIG. 10, according to some embodiments.

FIG. 11 is a sectional view taken along line 11-11 in FIG. 10, according to some embodiments. As shown in FIG. 11, the body portion 1510 has a plurality of passages or lumens 1511 extending within the body portion 1510, which can also be described as passages or channels. In various examples, the plurality of lumens 1511 extend the length of the body portion 1510 through the proximal and distal sections. In some embodiments, the plurality of lumens 1511 include a plurality of locking member lumens, such as first locking member lumen 1513 and second locking member lumen 1515. Additionally, in some embodiments the plurality of lumens 1511 include a first constraint lumen 1517, a second constraint lumen 1519, a third constraint lumen 1521, and a fourth constraint lumen 1523, although a number of additional lumens (e.g., eight, ten, twelve, etc.), are contemplated. In some embodiments, the plurality of lumens 1511 further includes a central lumen 1525. In various examples, the first locking member lumen 1513 and the second locking member lumen 1515, as well as the first constraint lumen 1517, the second constraint lumen 1519, the third constraint lumen 1521, and the fourth constraint lumen 1523 are each optionally located at a desired angular position about the central longitudinal axis Xa of the body portion 1510.

The support portion 1512 is generally configured to be received in the prosthetic valve 1000 and to support the prosthetic valve 1000 through delivery to, and deployment at a desired treatment location in a body of a patient (not shown). As shown, the support portion 1512 extends from the distal section 1520 of the body portion 1510 and has a central longitudinal axis Xb. In various examples, the central longitudinal axis Xb of the support portion 1512 is parallel with the central longitudinal axis Xa of the body portion 1510. In some examples, the central longitudinal axis Xb is coaxial with the central longitudinal axis Xa. The support portion 1512 includes a shaft 1526. In some examples, the shaft 1526 supports the one or more constraints of the plurality of constraints 1516.

In various examples, the support portion 1512 further includes a first pair of guide elements 1522 and a second pair of guide elements 1524, as discussed further below.

In various embodiments, the shaft 1526 is formed as a hollow tube (e.g., hypotube), for example using nitinol, stainless steel, or other metallic or polymeric materials. In various examples, the shaft 1526 is configured to receive a guidewire (not shown) for guiding the delivery device 1500 to a desired treatment location within the patient's anatomy. If desired, however, the shaft 1526 may also be formed as a solid member without any internal lumen.

In various examples, each pair of guide elements 1522 and 1524 is adapted and arranged to interface with one or more of the constraints 1516. The first pair of guide elements 1522 generally includes a proximal guide element 1528 and a distal guide element 1530. It will be appreciated that the first pair of guide elements 1522 may additionally include an intermediate guide element situated between the proximal guide element 1528 and the distal guide element 1530, as desired, though one is not illustrated. In some examples, the second pair of guide elements 1524 generally includes a proximal guide element 1532 and a distal guide element 1534.

It will be appreciated that the second pair of guide element may likewise additionally include an intermediate guide element situated between the proximal guide element 1532 and the distal guide element 1534, as desired, though one is not illustrated. In some examples the proximal guide element 1528 and the distal guide element 1530 are configured to support the leaflet frame subcomponent 1200 In various examples, each of the proximal guide element 1528 and the distal guide element 1530 of the first pair of guide elements 1522 defines a central longitudinal axis (not separately labeled) that is coaxial with the central longitudinal axis Xa of the support portion 1512 and by transitive theory, the central longitudinal axis of the shaft 1526, according to some examples.

As shown in FIG. 12, in some embodiments, the proximal guide element 1528 includes a central lumen 1527 through which the shaft 1526 is received, for coupling the proximal guide element 1528 to the shaft 1526. As shown, the proximal guide element 1528 also includes a plurality of passages or lumens 1529, also described as channels or lumens. In various examples, the plurality of lumens 1529 include a plurality of locking member passages, such as first locking member passage 1533 and second locking member passage 1535. Additionally, in some embodiments the plurality of lumens 1529 include a first constraint passage 1537, a second constraint passage 1539, a third constraint passage 1541, and a fourth constraint passage 1543, although a number of additional passages (e.g., eight, ten, twelve, etc.), are contemplated. In various examples, the first locking member passage 1533 and the second locking member passage 1535, as well as the first constraint passage 1537, the second constraint passage 1539, the third constraint passage 1541, and the fourth constraint passage 1543 are each optionally located at a desired angular position about the central longitudinal axis Xb of the support portion 1512.

As shown, the locking member passages and the constraint member passages correspond in angle and in offset with the locking member lumens and the constraint member lumens of the body portion 1510, discussed above. For example, the first locking member passage 1533 corresponds with the first locking member lumen 1513 in that the first locking member passage 1533 is at an angular position corresponding to 12 o'clock or 0 degrees.

As seen with reference between FIGS. 12 and 13, the distal guide element 1530 is substantially similar to the proximal guide element 1528. In some examples, the distal guide element 1530 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide element 1530 also defines a central longitudinal axis (not separately labeled) that is coaxial with the central longitudinal axis Xa of the support portion 1512 and by transitive theory, the central longitudinal axis of the shaft 1526 (as well as the proximal guide element 1528), according to some examples.

As shown in FIG. 13, in some embodiments, the distal guide element 1530 includes a central lumen 1545 through which the shaft 1526 is received, for coupling the distal guide element 1530 to the shaft 1526. As shown, the distal guide element 1530 also includes a plurality of passages or lumens 1547, also described as channels or lumens. In various examples, the plurality of lumens 1547 include a plurality of locking member passages, such as first locking member passage 1553 and second locking member passage 1555. Additionally, in some embodiments the plurality of lumens 1547 include a first constraint passage 1557, a second constraint passage 1559, a third constraint passage 1561, and a fourth constraint passage 1563, although a number of additional passages (e.g., eight, ten, twelve, etc.), are contemplated. In various examples, the first locking member passage 1553 and the second locking member passage 1555, as well as the first constraint passage 1557, the second constraint passage 1559, the third constraint passage 1561, and the fourth constraint passage 1563 are each optionally located at a desired angular position about the central longitudinal axis Xb of the support portion 1512.

As shown, the locking member passages and the constraint member passages correspond in angle and in offset with the locking member lumens and the constraint member passages of the proximal guide element 1528, discussed above. For example, the first locking member passage 1553 corresponds with the first locking member passage 1533 in that the first locking member passage 1553 is at an angular position corresponding to 12 o'clock or 0 degrees.

In various embodiments, each of the plurality of lumens 1529 of the proximal guide element 1528 is aligned with a correspond passage of the plurality of lumens 1547 of the distal guide element 1530. In other words, the first locking member passage 1533 is angularly aligned with the first locking member passage 1553, and the first constraint passage 1537 with the first constraint passage 1557, etc., as mentioned above. It will be appreciated, however, that one or more of the plurality of lumens 1529 and the plurality of lumens 1547 may be angularly misaligned, or out of alignment with one another without departing from the spirit or scope of the present disclosure. Moreover, it should be readily appreciated that the distal guide element 1530 need not have the same number of passages as the proximal guide element 1528, as discussed below.

As shown in FIGS. 14 and 15, the proximal guide element 1532 and the distal guide element 1534 of the second pair of guide elements 1524 are generally cylindrical overall, having transverse outer profiles that are cylindrical, which also corresponds to a transverse outer profile that is circular in transverse cross-section. It will be appreciated that although cylindrical profiles are contemplated, any of a variety of tapers, steps, chamfers and other features is also contemplated. In some examples, a diameter of the proximal guide element 1532 and the distal guide element 1534 of the second pair of guide elements 1524 is generally less than a diameter of the proximal guide element 1528 and the distal guide element 1530 of the second pair of guide elements 1524. In some examples such a configuration provides that the leaflet frame subcomponent 1200 can be proximally retracted (e.g., telescoped) into an interior region defined by the anchor frame subcomponent 1100. That is, by providing the proximal guide element 1532 and the distal guide element 1534 with smaller diameters, the leaflet frame subcomponent 1200 can be reduced to a smaller cross sections suitable for being received within the anchor frame subcomponent 1100. In some examples the proximal guide element 1532 and the distal guide element 1534 are configured to support the leaflet frame subcomponent 1200.

In various examples, each of the proximal guide element 1532 and the distal guide element 1534 of the second pair of guide elements 1524 defines a central longitudinal axis (not separately labeled) that is coaxial with the central longitudinal axis Xa of the support portion 1512 and by transitive theory, the central longitudinal axis of the shaft 1526, according to some examples.

As shown in FIG. 14, in some embodiments, the proximal guide element 1532 includes a central lumen 1565 through which the shaft 1526 is received, for coupling the proximal guide element 1532 to the shaft 1526. As shown, the proximal guide element 1532 also includes a plurality of passages or lumens 1567, also described as channels or lumens. In various examples, the plurality of passages or lumens 1567 include second locking member passage 1575, a first constraint passage 1577, and a second constraint passage 1579, although a number of additional passages (e.g., eight, ten, twelve, etc.), are contemplated. In various examples, the second locking member passage 1575, as well as the first constraint passage 1577 and the second constraint passage 1579, are each optionally located at a desired angular position about the central longitudinal axis Xb of the support portion 1512.

As shown, the locking member passage and the constraint member passages correspond in angle and in offset with the locking member passages and the constraint member passages of the distal guide element 1530, discussed above. For example, the second locking member passage 1575 corresponds with the second locking member passage 1555 in that the second locking member passage 1575 is at an angular position corresponding to 2 o'clock or 60 degrees.

As seen with reference between FIGS. 14 and 15, the distal guide element 1534 is substantially similar to the proximal guide element 1532. In some examples, the distal guide element 1534 is also cylindrical overall, having a transverse outer profile that is cylindrical, which also corresponds to a transverse outer profile that is circular in transverse cross-section, although any of a variety of tapers, steps, chamfers and other features are also contemplated, as mentioned above.

The distal guide element 1534 also defines a central longitudinal axis (not separately labeled) that is coaxial with the central longitudinal axis Xa of the support portion 1512 and by transitive theory, the central longitudinal axis of the shaft 1526 (as well as the proximal guide element 1532), according to some examples.

As shown in FIG. 15, in some embodiments, the distal guide element 1534 includes a central lumen 1581 through which the shaft 1526 is received, for coupling the distal guide element 1534 to the shaft 1526. As shown, the distal guide element 1534 also includes a plurality of passages 1583, also described as channels or lumens. In various examples, the plurality of passages 1583 include second locking member passage 1585, a first constraint passage 1587, and a second constraint passage 1589, although a number of additional passages (e.g., eight, ten, twelve, etc.), are contemplated. In various examples, the second locking member passage 1585, as well as the first constraint passage 1587 and the second constraint passage 1589, are each optionally located at a desired angular position about the central longitudinal axis Xb of the support portion 1512. It is to be understood that the central lumen 1525, 1527, 1545, 1565, and 1581 as well as any one of the plurality of lumens 1511, 1529, 1547, 1567, or 1583 as shown in FIGS. 11 through 15 may be used to receive the cutting element 1001.

As shown, the locking member passage and the constraint member passages correspond in angle and in offset with the locking member passages and the constraint member passages of the proximal guide element 1532, discussed above. For example, the second locking member passage 1585 corresponds with the second locking member passage 1575 in that the second locking member passage 1585 is at an angular position corresponding to 2 o'clock or 60 degrees.

As shown in FIG. 10, the plurality of constraints 1516 comprise a first pair of constraints 1536 and a second pair of constraints 1538, wherein the first pair of constraints 1536 are associated with the first pair of guide elements 1522 and wherein the second pair of constraints 1538 are associated with the second pair of guide elements 1524. In various examples, each pair of constraints is adapted and arranged to interface with a respective one of the anchor frame subcomponent 1100 and the leaflet frame subcomponent 1200. The first pair of constraints 1536 generally includes a proximal constraint 1540 and a distal constraint 1542. It will be appreciated that the first pair of constraints 1536 may additionally include an intermediate constraint situated between the proximal constraint 1540 and the distal constraint 1542, as desired, though one is not illustrated. The second pair of constraints 1538 generally includes a proximal constraint 1544 and a distal constraint 1546. It will be appreciated that the second pair of constraints 1538 may likewise additionally include an intermediate constraint situated between the proximal constraint 1544 and the distal constraint 1546, as desired, though one is not illustrated.

In some embodiments, each of the plurality of constraints 1516 is formed as a fiber, strand, wire, combinations thereof or the like, and may be braided, wound, extruded, or otherwise formed of metallic or polymeric materials. For example, each of the constraints 1516 may be formed from braided strands of material, such as UHMWPE or ePTFE. Although three are shown, any number of constraints 28 (e.g., one, two, four, nine, etc.) are contemplated. In some embodiments, the proximal constraint 1540 includes a catch 1548 in the form of a terminal, closed loop or eyelet, for example. The catch 1548 is optionally formed using braiding methods (e.g., by twisting the braid into itself or through a continuous braiding method that forks a single strand into two separates strands and then rebraids them into a single strand to form an eyelet). The distal constraint 1542 similarly includes a catch 1550, as does the proximal constraint 1544, which includes catch 1552. Distal constraint 1546 includes a catch 1554.

Figure 16:
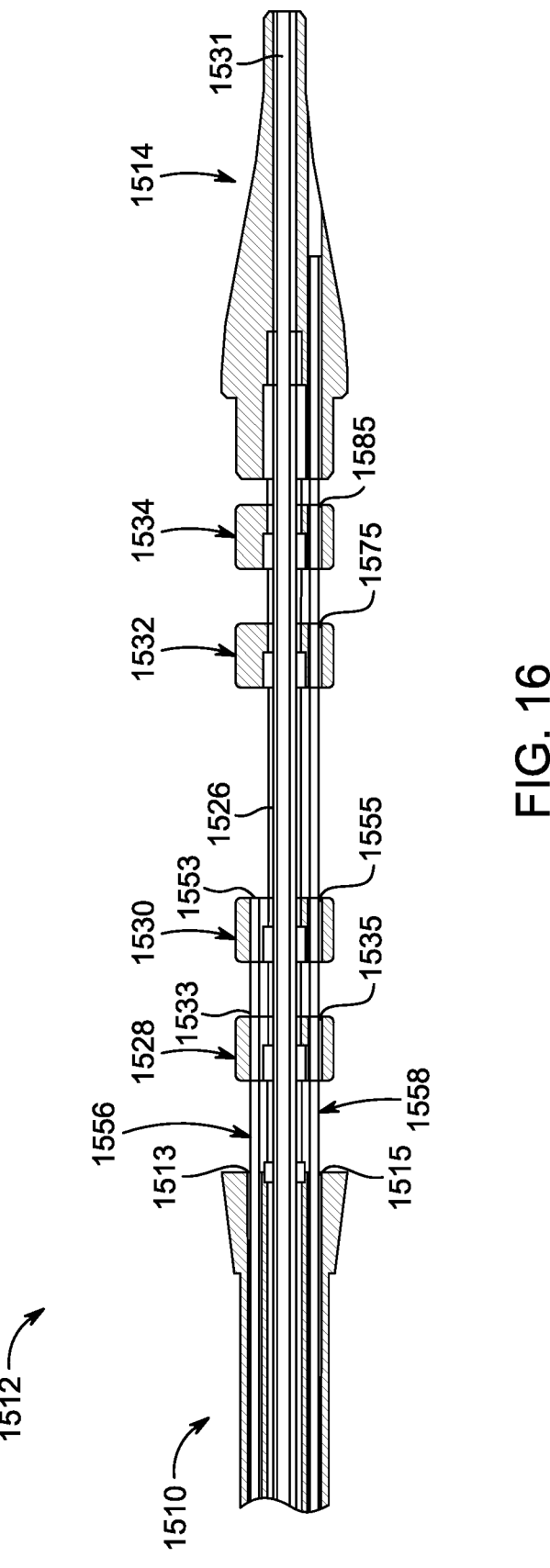
FIG. 16 is a longitudinal section of a delivery device, according to some embodiments.

In various examples, the plurality of locking members 1518 include a first locking member 1556 and a second locking member 1558. The first locking member 1556 is generally associated with securing or otherwise engaging with the first pair of constraints 1536 and the first pair of guide elements 1522, while the second locking member 1558 is generally associated with securing or otherwise engaging with the second pair of constraints 1538 and the second pair of guide elements 1524. For example, as shown in FIG. 16, the first locking member 1556 extends through first locking member lumen 1513 of the body portion 1510 and into the first locking member passage 1533 and the second locking member passage 1555 of the proximal guide element 1528 and the distal guide element 1530 of the first pair of guide elements 1522. Likewise, as shown in FIG. 16, the second locking member 1558 extends through second locking member lumen 1515 of the body portion 1510, through the second locking member passage 1535 and the second locking member passage 1555 of the proximal guide element 1528 and the distal guide element 1530 of the first pair of guide elements 1522, and into the second locking member passage 1575 and the second locking member passage 1585 of the proximal guide element 1532 and the distal guide element 1534 of the second pair of guide elements 1524. It will be appreciated that the second locking element lumens and passages are shown in FIG. 16 as rotated approximately 120 degrees for clarity.

In various examples, the first locking member 1556 and the second locking member 1558 are each formed as a wire, strand, fiber or the like, and may be braided, wound, extruded, or otherwise formed of metallic or polymeric materials. In some examples, the first locking member 1556 and the second locking member 1558 are wires formed of stainless steel, nitinol, or other material. It should be appreciated that while the second locking member 1558 is illustrated as extending into the tip portion 1514, the second locking member 1558 may terminate proximal to the tip portion 1514. In some such examples, the second locking member 1558 terminates in the distal guide element 1534 of the second pair of guide elements 1524. In various examples, each of the first locking member 1556 and the second locking member 1558 is slidably received in the respective locking member lumens and passages discussed above such that the first locking member 1556 and the second locking member 1558 are retractable from the respective guide elements into and/or through which they extend.

In various embodiments, the first locking member 1556 and the second locking member 1558 and the plurality of constraints 1516 extend through the body portion 1510 to the support portion 1512. In some examples, the first locking member 1556 and the second locking member 1558 and the plurality of constraints 1516 extend from an actuation portion (not shown) coupled to the inlet end of the body portion 1510. In various examples, the actuation portion includes a handle (not shown) that is operable to manipulate the first locking member 1556 and the second locking member 1558 and the plurality of constraints 1516. In some examples, the handle includes one or more spindles or other mechanisms that are each able to be rotated to proximally retracted or distally advance the respective constraint or locking member. In some examples, one or more of the spindles may be optionally rotationally coupled to one another and/or are independently rotatable as desired. Additionally, various forms of clutches, gears, or other means for controlling relative rotational speed, timing, or other interactions between the spindles are contemplated. The spindles may be configured to be used to wind up, or tension, and let out, or de-tension, the constraints 1516 and locking members (e.g., 1556 and 1558).

Additionally, those of skill should appreciate that the actuation portion is operable to actuate (e.g., proximally retract and/or distally advance) the first locking member 1556 and the second locking member 1558 independent of one another. Similarly, it should be appreciated that the actuation portion is operable to actuate one or more of the constraints of the plurality of constraints 1516 independent of each of the other constraints of the plurality of constraints. That is, in some examples each of the constraints can be independently actuated. Alternatively, in some examples, two or more constraints of the plurality of constraints 1516 may be operated in conjunction with one another, as those of skill will appreciate.

In some examples, the plurality of constraints 1516 and the first locking member 1556 and the second locking member 1558 extend through body portion. In some examples the plurality of constraints 1516 and the first locking member 1556 and the second locking member 1558 then extend through one or more of the guide elements of the first and/or second pairs of guide elements 1522 and 1524. For example, the plurality of constraints 1516 and the first locking member 1556 and the second locking member 1558 extend through the respective constraint passages and locking member passages, respectively, of the proximal guide element 1528 discussed above.

Figure 17:
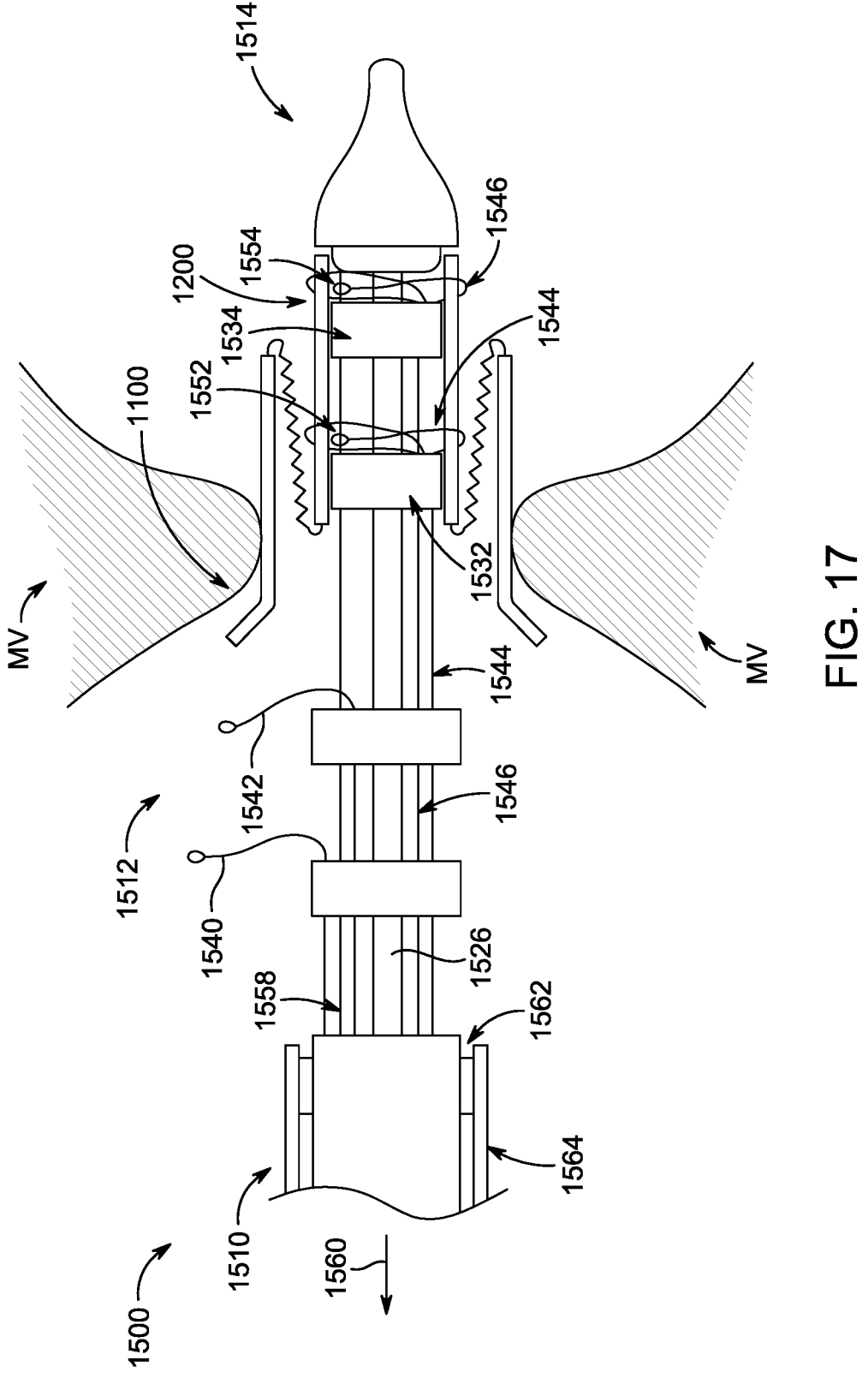
FIG. 17 is a side view of a delivery device partially coupled to a portion of a prosthetic valve, with the prosthetic valve in a partially deployed state, according to some embodiments.

In various embodiments, that the plurality of constraints 1516 are operable to extend distally out of a respective one of the plurality of passages and then radially away from the central longitudinal axis Xa of the support portion 1512. In various embodiments, each constraint (e.g., 1540, 1542, 1544, 1546) is then routed around a respective portion (e.g., leaflet frame subcomponent 1200 or anchor frame subcomponent 1100) of the prosthetic valve 1000. In various examples, the constraint is secured to the one of the first locking member 1556 and the second locking member 1558. In particular, the proximal constraint 1540 and the distal constraint 1542 of the first pair of constraints 1536 are secured by the first locking member 1556, while the proximal constraint 1544 and the distal constraint 1546 of the second pair of constraints 1538 are secured by the second locking member 1558, as discussed herein. In some examples, the constraint is routed such that the constraint forms loop and crosses back over itself (see, e.g., FIG. 17) before being secured to a respective locking member. In various examples, and as shown in FIG. 17, the constraints are secured to a respective one of the first locking member 1556 and the second locking member 1558 by receiving the respective locking member through the catch of the constraint. As shown in FIG. 17, each of the proximal constraint 1544 and the distal constraint 1546 are looped around the leaflet frame subcomponent 1200 and secured to the second locking member 1558, wherein the second locking member 1558 is received by the catch 1552 and the catch 1554 of the proximal constraint 1544 and the distal constraint 1546, respectively.

As mentioned above, in some examples, the constraints are looped around the prosthetic valve 1000 (e.g., around a respective one of the leaflet frame subcomponent 1200 or the anchor frame subcomponent 1100). In various examples, one or more of the constraints 1516 is operable to be woven through one or more apertures formed in one or the other of the leaflet frame subcomponent 1200 and the anchor frame subcomponent 1100. For instance, it will be appreciated that the proximal constraint 1544 and the distal constraint 1546 are operable to be woven through one or more apertures of the leaflet frame subcomponent 1200, while the proximal constraint 1540 and the distal constraint 1542 are operable to be woven through one or more apertures of the anchor frame subcomponent 1100, as mentioned above. In some examples, the apertures are formed in a film, membrane, or other construct covering the leaflet frame subcomponent 1200 and the anchor frame subcomponent 1100. In some examples, the constraints pass exterior to the frame members 1212 of the leaflet frame subcomponent 1200 and exterior to the frame members 1112 of the anchor frame subcomponent 1100. It will be appreciated that with the constraints woven through the apertures of the respective frames (e.g., the leaflet frame subcomponent 1200 or the anchor frame subcomponent 1100), the constraints can operate to retain the leaflet frame subcomponent 1200 and the anchor frame subcomponent in a compacted delivery profile. Additionally, with the constraints woven through the apertures of the respective frames (e.g., the leaflet frame subcomponent 1200 or the anchor frame subcomponent 1100), the constraints can operate to transfer translational movement of the delivery device 1500 to the leaflet frame subcomponent 1200 and/or the anchor frame subcomponent 1100. Such a configuration provides that the delivery device 1500 and the leaflet frame subcomponent 1200 can be proximally retracted relative to the anchor frame subcomponent 1100 after the anchor frame subcomponent 1100 is deployed from the delivery system as discussed above.

Moreover, it will be appreciated that such a configuration provides that proximally tensioning the constraints 1516 causes the constraints to constrict, thereby operating to reduce a diameter (or at least maintain a diameter) of the looped portion of the constraints, which results in looped portion of the constraint being operable to deliver a collapsing or constraining force to the prosthetic valve for example. Conversely, release of the tension permits has the opposing effect (e.g., expanding the diameter of the looped portion of the constraints 1516).

Examples of suitable attachment methods and constraining methods similar to those described above can be found in, entitled "TRANSCATHETER DEPLOYMENT SYSTEMS AND ASSOCIATED METHODS," filed by Applicant hereof on even date herewith.

Turing now to FIG. 17, a nonlimiting delivery operation in accordance with the above discussed examples and embodiments is illustrated and described. As shown, the first pair of constraints 1536 (e.g., the proximal constraint 1540 and the distal constraint 1542) has been released from the first locking member 1556 such that the anchor frame subcomponent 1100 is operable to expand and engage a valve annulus of a mitral valve, for example. However, as shown, the proximal constraint 1544 and the distal constraint 1546 remain coupled with second locking member 1558 and the leaflet frame subcomponent 1200.

Though not illustrated as such in FIG. 17, it will be understood that in actuality, each of the proximal constraint 1544 and the distal constraint 1546 are woven through one or more portions of the leaflet frame subcomponent 1200 as discussed above.

Accordingly, with the anchor frame subcomponent 1100 unconstrained and the leaflet frame subcomponent 1200 at least partially constrained by one or more of the proximal constraint 1544 and the distal constraint 1546, the delivery device 1500 can be proximally withdrawn in the direction of arrow 1560 (e.g., proximally translated) relative to the valve annulus and the anchor frame subcomponent 1100 such that the leaflet frame subcomponent 1200 is proximally withdrawn into the interior region defined by the anchor frame subcomponent 1100, as discussed herein. In various examples, the delivery device 1500 is proximally withdrawn until the leaflet frame subcomponent 1200 becomes nested within the anchor frame subcomponent 1100, as discussed herein.

In some examples, after releasing the first pair of constraints 1536 from the first locking member 1556 and the anchor frame subcomponent 1100, and before proximally withdrawing the delivery device 1500 and the leaflet frame subcomponent 1200, a tension in one or more of the proximal constraint 1544 and the distal constraint 1546 may be reduced, thereby enabling one or more of the leaflet frame subcomponent 1200 to partially deploy. Thus, in such examples, the delivery device 1500 is operable to partially deploy the leaflet frame subcomponent 1200 prior to proximally withdrawing the delivery device 1500 and the leaflet frame subcomponent 1200.

It should be appreciated that while the above discussed examples and embodiments include a delivery system including a plurality of locking members, the delivery system may be operable with a single locking member. For instance, in some examples the locking member may engage and retain each of a first constraint extending about the anchor frame subcomponent 1100 and a second constraint extending about the leaflet frame subcomponent 1200. In such examples the locking member is generally routed through one or more guide elements such that proximally retracting inlet end of the locking element results in an outlet end of the locking element advancing at least initially distally along the support portion of the delivery system such that the constraint extending about the anchor frame subcomponent 1100 can be released prior to releasing the constraint extending about the leaflet frame subcomponent 1200.

Figure 18:
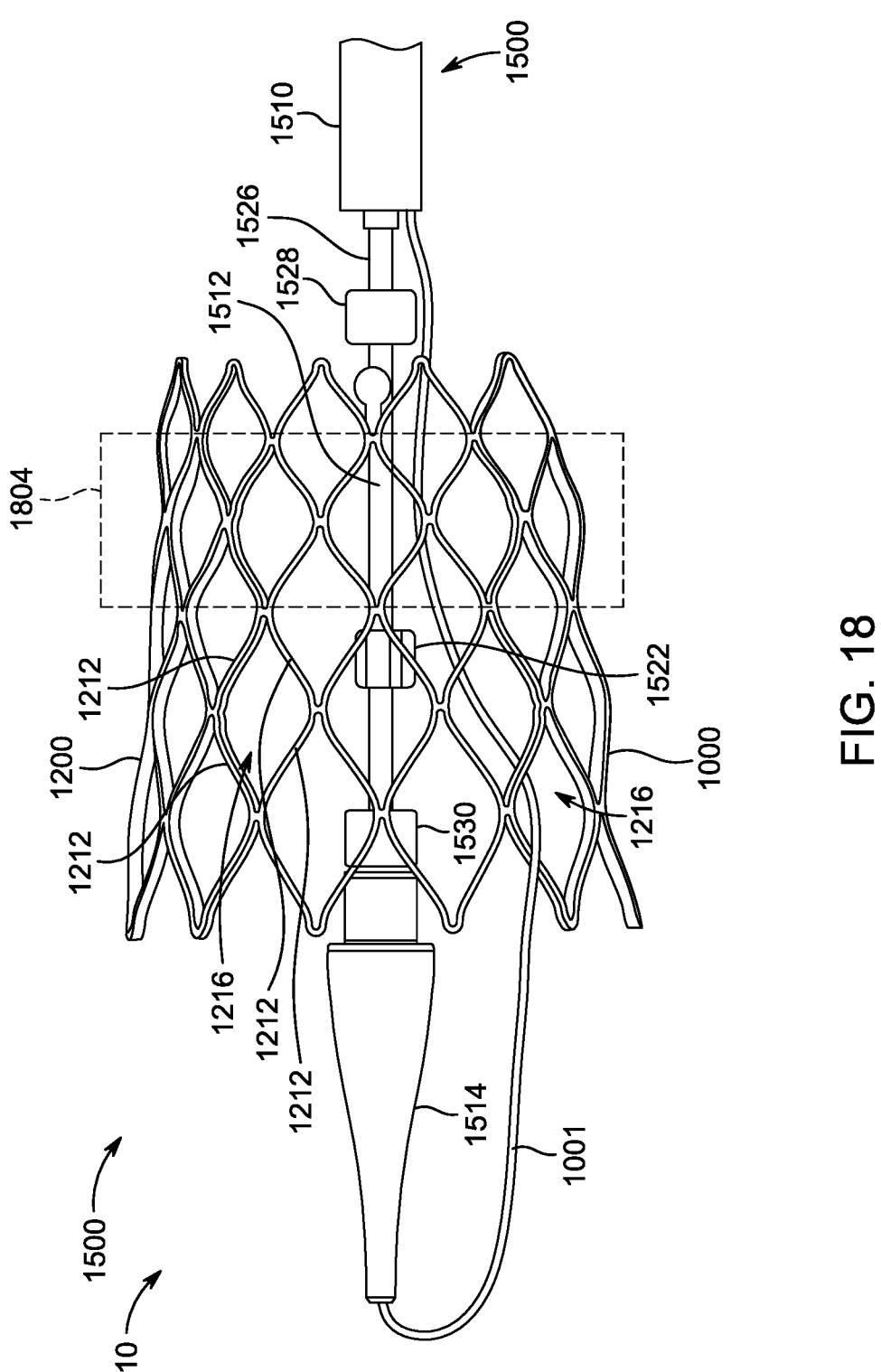
FIG. 18 is a side view of a delivery system with certain portions removed for ease of visualization, according to some embodiments.

FIG. 18 shows another example transcatheter delivery device 1500, according to some embodiments. The delivery device 1500 (which may be a delivery catheter) includes a body portion 1510, a support portion 1512, a tip portion 1514, and a plurality of constraints (not shown). As shown, the prosthetic valve 1000 includes a single-frame support structure design (e.g., the leaflet frame subcomponent 1200, without the anchor frame subcomponent 1100 or the interstage 1300). For reference, any of a variety of other single-frame support structure implants may be implemented with the transcatheter delivery system 10, including stents, stent grafts, endovascular filters, occluders and the like. As shown, the prosthetic valve 1000 includes a leaflet construct (not shown) located inside, and supported by the support portion 1512 within the bounds of a leaflet region 1804. In some embodiments, the leaflet region 1804 is positioned along the support portion 1512 between the proximal guide element 1528 and the distal guide element 1530 positioned along a shaft 1526. For example, in some embodiments, the leaflet region 1804 does not extend longitudinally beyond the proximal guide element 1528 and the distal guide element 1530. In some embodiments, the indicated leaflet region 1804 can be located between one or more guide elements 1522, which may reduce or eliminate volume of the guide(s) in the leaflet region 1804 when the prosthetic valve 1000 is compacted into the delivery state onto the support portion 1512. As referenced, the prosthetic valve 1000 as shown does not comprise of a plurality of subcomponents. In some examples, the cutting element 1001 is coupled with the prosthetic valve 1000 through one of the apertures 1216 formed from the leaflet frame subcomponent 1200. As shown, the cutting element 1001 passes through, and is therefore coupled to, the leaflet frame subcomponent 1200 relative near the inflow end of the prosthetic valve 1000. In various examples, the cutting element 1001 passes through, and is therefore coupled to, the leaflet frame subcomponent 1200 at an intermediate location, between the inflow and outflow ends, or at a location proximate the outflow end of the prosthetic valve 1000 as desired.

Delivery and Deployment Method Including Tissue Cutting

In general terms, a method for treating a human patient with a diagnosed condition or disease associated with valve insufficiency or valve failure of a native valve, may include implanting the implant of any of the previously described designs, for example with the implant being a prosthetic valve and the prosthetic valve being implanted at or adjacent to a location associated with the native valve.

In various examples, a method of delivering an implant, such as the prosthetic valve 1000, to a treatment site, such as a native valve orifice, includes positioning the implant at the treatment site with a delivery device, such as delivery device 1500, and cutting tissue, such as a native valve leaflet (e.g., anterior mitral valve leaflet) at the treatment site with a cutting element, such as cutting element 1001, the cutting element being coupled to the delivery device and/or the implant. Thus, in some methods the cutting element defines a loop portion, the method further comprising adjusting a size of the loop portion prior to cutting the tissue. The method may also include uncoupling the cutting element from the implant after the tissue is cut, and removing the cutting element from the treatment site. For example, the cutting element may be decoupled from the implant by tensioning, or pulling on the cutting element remotely and then retracting the cutting element through the delivery device (e.g., delivery device 1500). The implant may be deployed at the treatment site with the tissue being cut at least one of prior to, during, or following deploying the implant.

Figures 19, 20:
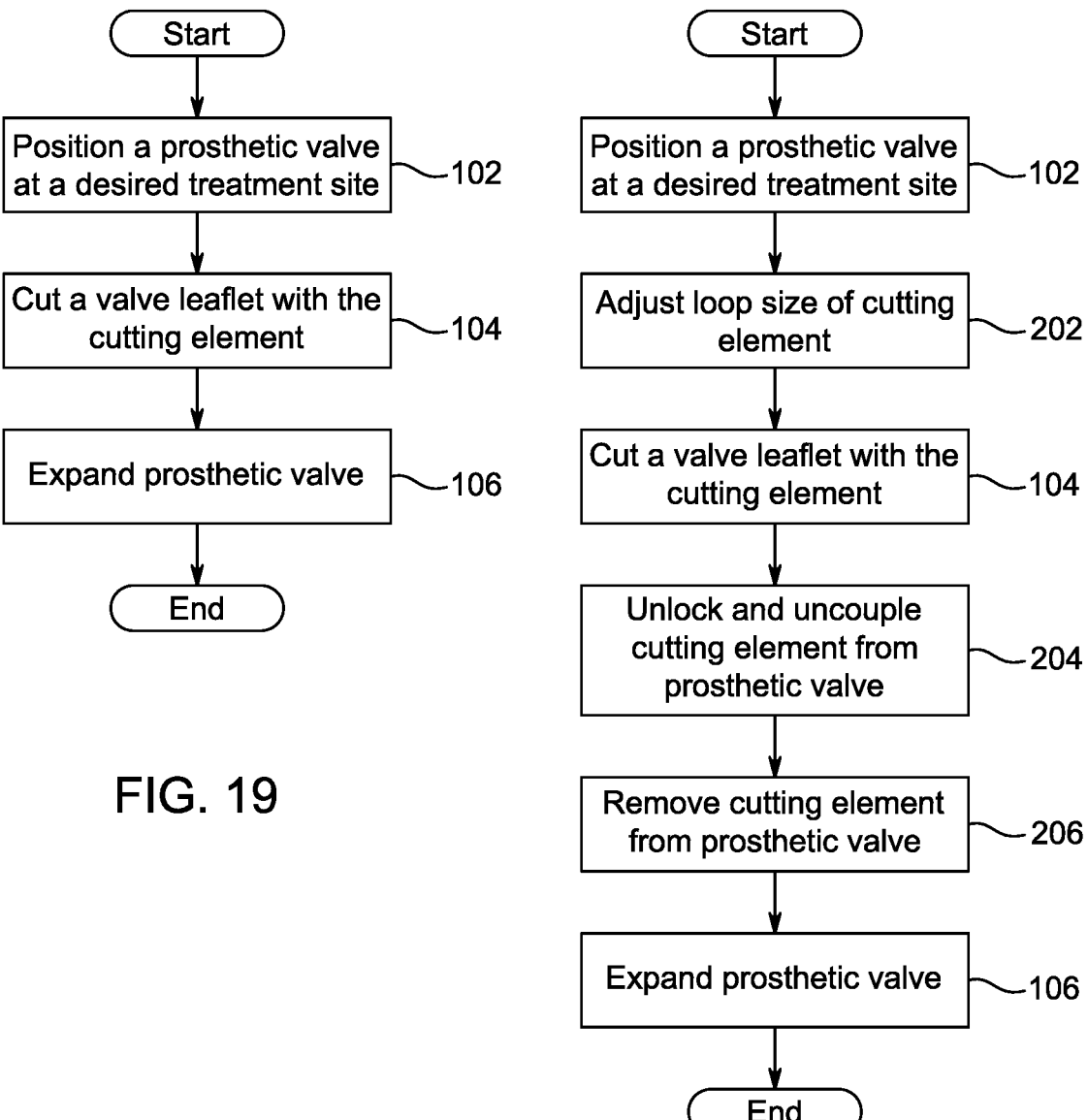
FIGS. 19 and 20 are flow diagrams of delivery methods, according to some embodiments.

FIG. 19 shows a method of delivering a prosthetic valve to a treatment site, such as the prosthetic valve 1000 of any of the prior examples. The prosthetic valve is positioned at a desired treatment site; 102. A valve leaflet is cut with a cutting element coupled with the prosthetic valve; 104. As previously explained, the valve leaflet may be an anterior mitral leaflet in some examples, and cutting the valve leaflet prevents the valve leaflet from deflecting toward the left ventricular outflow tract (LVOT) and possibly causing obstructions in the left ventricular outflow tract (LVOT) in the future. The tissue to be cut, and in this case the anterior leaflet (AL), may be cut either prior to or after the prosthetic valve is expanded, thereby permitting the prosthetic valve to be deployed at the treatment site without the valve leaflet deflecting to block, or otherwise blocking the left ventricular outflow tract (LVOT); 106.

FIG. 20 shows another method of delivering a prosthetic valve to a treatment site, such as any prior embodiment of the prosthetic valve 1000 provided in the foregoing description. After the previously mentioned block 102 to position the prosthetic valve at the desired location or treatment site, the loop size of the cutting element is adjusted; 202. In some example, the loop size adjustment is performed by distally advancing or proximally retracting one end of the cutting element 1001. For example, the loop size may be adjusted to be smaller for situations where a more precise, or smaller cut is required, and alternatively the loop size may be adjusted to be larger for situations where a larger section of tissue is to be cut. This step is followed by block 104 in which the valve leaflet is cut with the cutting element. Thereafter, the cutting element is unlocked and uncoupled from the prosthetic valve; 204. In some examples, the unlocking is achieved by deactivating a locking mechanism that locks one or both ends of the cutting element, thus allowing the cutting element to be freely movable with respect to the prosthetic valve. Then, the cutting element is removed from the body, for example by proximally pulling on one end of the cutting element until the entire cutting element is pulled out of the prosthetic valve, and in some examples out of the body; 206. The prosthetic valve can then be expanded at the treatment site according to block 106 as previously explained.

Bio-Active Agents

In some embodiment, all or a part of the prosthetic valve, including the leaflets, may be provided with a biologically active (bio-active) agent. Bio-active agents can be coated onto a portion or the entirety of the prosthetic valve, including the leaflet and/or leaflet construct, for controlled release of the agents once the prosthetic valve is implanted.

Such bio-active agents can include, but are not limited to, anti-thrombogenic agents such as, but not limited to, heparin. Bio-active agents can also include, but are not limited to agents such as anti-proliferative/antimitotic agents including natural products such as vinca alkaloids (e.g., vinblastine, vincristine, and vinorelbine), paclitaxel, epidipodophyllo-toxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin) and mitomycin, enzymes (e.g., L-asparaginase which systemically metabolizes L-aspara-gine and deprives cells which do not have the capacity to synthesize their own asparagine); antiplatelet agents such as G(GP) IIb/IIIa inhibitors and vitronectin receptor antago-nists; anti-proliferative/antimitotic alkylating agents such as nitrogen mustards (e.g., mechlorethamine, cyclophosph-amide and analogs, melphalan, chlorambucil), ethylen-imines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC); anti-proliferative/antimitotic antime-tabolites such as folic acid analogs (e.g., methotrexate), pyrimidine analogs (e.g., fluorouracil, floxuridine, and cyt-arabine), purine analogs and related inhibitors (e.g., mer-captopurine, thioguanine, pentostatin and 2-chlorodeoxy-adenosine {cladribine}); platinum coordination complexes (e.g., cisplatin and carboplatin), procarbazine, hydroxyurea, mitotane, am inoglutethimide; hormones (e.g., estrogen); anti-coagulants (e.g., heparin, synthetic heparin salts and other inhibitors of thrombin); anti-platelet agents (e.g., aspi-rin, clopidogrel, prasugrel, and ticagrelor); vasodilators (e.g., heparin, aspirin); fibrinolytic agents (e.g., plasminogen activator, streptokinase, and urokinase), aspirin, dipyrida-mole, ticlopidine, clopidogrel, abciximab; antimigratory agents; antisecretory agents (e.g., breveldin); anti-inflam-matory agents, such as adrenocortical steroids (e.g., cortisol, cortisone, fludrocortisone, prednisone, prednisolone, 6α-methylprednisolone, triamcinolone, betamethasone, and dexamethasone), non-steroidal agents (e.g., salicylic acid derivatives, such as aspirin); para-aminophenol derivatives (e.g., acetaminophen); indole and indene acetic acids (e.g., indomethacin, sulindac, and etodalac), heteroaryl acetic acids (e.g., tolmetin, diclofenac, and ketorolac), arylpropi-onic acids (e.g., ibuprofen and derivatives), anthranilic acids (e.g., mefenamic acid and meclofenamic acid), enolic acids (e.g., piroxicam, tenoxicam, phenylbutazone, and oxyphen-thatrazone), nabumetone, gold compounds (e.g., auranofin, aurothioglucose, and gold sodium thiomalate); immunosup-pressives (e.g., cyclosporine, tacrolimus (FK-506), siroli-mus (rapamycin), azathioprine, and mycophenolate mofetil); angiogenic agents (e.g., vascular endothelial growth factor (VEGF)), fibroblast growth factor (FGF); angiotensin receptor blockers; nitric oxide donors; anti-sense oligonucleotides and combinations thereof; cell cycle inhibitors, mTOR inhibitors, growth factor receptor signal transduction kinase inhibitors; retinoids; cyclin/CDK inhibitors; HMG co-enzyme reductase inhibitors (statins); and protease inhibitors.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications. The scope of the concepts addressed in this disclosure has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the scope.

What is claimed is:

1. A delivery system comprising:
a delivery device;
an implant having a support structure, the implant being releasably coupled to the delivery device; and
a tissue cutting system coupled to the delivery device and the implant, the tissue cutting system including a cutting element comprising a wire formed of a conductive material electrically connected to a current source and configured to cut tissue, wherein the wire comprises a first portion and a second portion extending from the first portion,
wherein the first portion of the wire extends through a lumen of the delivery device and the implant and outwardly from a distal tip portion of the delivery device in a distal direction, and
wherein the second portion of the wire extends from a distal end of the first portion of the wire in a proximal direction alongside the delivery device and the implant and then back into the delivery device at a location proximal the distal tip portion of the delivery device.

2. The delivery system of claim 1, wherein the first and second portions of the wire form a loop portion that extends radially outward relative to the delivery device, and wherein the loop portion is configured to be adjusted in size by a user.

3. The delivery system of claim 1, wherein the cutting element comprises a protective cover extending partially over the wire and rendering at least a portion of the wire inoperable for cutting tissue.

4. The delivery system of claim 1, further comprising an outer sheath retractably disposed over at least a portion of the cutting element.

5. The delivery system of claim 4, wherein the outer sheath comprises a thermally insulating material.

6. The delivery system of claim 4, wherein the outer sheath comprises an electrically insulating material.

7. The delivery system of claim 4, wherein the outer sheath comprises an abrasion-resistant material.

8. The delivery system of claim 1, wherein the support structure comprises a leaflet frame subcomponent and an anchor frame subcomponent.

9. The delivery system of claim 8, wherein the support structure further comprises an interstage flexibly coupling the leaflet frame subcomponent and the anchor frame subcomponent.

10. The delivery system of claim 9, wherein the cutting element is coupled to the interstage.

11. The delivery system of claim 8, wherein the cutting element extends through a framework of the leaflet frame subcomponent or the anchor frame subcomponent.

12. The delivery system of claim 1, wherein the support structure is configured to be self-expanding.

13. The delivery system of claim 1, wherein the support structure is configured to assume a collapsed, delivery configuration and an expanded, deployed configuration.

14. The delivery system of claim 1, wherein the cutting element is configured to cut tissue when the implant is in a deployed configuration.

15. The delivery system of claim 14, wherein the cutting element is configured to be uncoupled from the delivery system or the implant.

16. The delivery system of claim 1, wherein the delivery device comprises shaft defining the lumen through which the first portion of the wire extends, wherein the implant is mounted around the shaft such that the first portion and the second portion of the wire form a loop that extends through and alongside the implant.

17. A method of delivering an implant to a treatment site, the method comprising:
positioning the implant at the treatment site with a delivery device; and
cutting tissue at the treatment site with a cutting element that is coupled to the delivery device and the implant, wherein the cutting element comprises a first portion and a second portion extending from the first portion, wherein the first portion of the cutting element extends through a lumen of the delivery device and the implant and then distally from an opening in a distal tip portion of the delivery device, and
wherein the second portion of the cutting element curves from a distal end of the first portion of the cutting element in a proximal direction alongside the delivery device and the implant and back into the delivery device.

18. The method of claim 17, wherein the first and second portions of the cutting element define a loop portion, and wherein the method further comprises adjusting a size of the loop portion prior to cutting the tissue.

19. The method of claim 17, further comprising:
uncoupling the cutting element from the implant after the tissue is cut, and removing the cutting element from the treatment site.

20. The method of claim 17, further comprising:
deploying the implant at the treatment site, wherein the tissue is cut at least one of prior to, during, or following deploying the implant.

21. A method for treating a human patient with a diagnosed condition or disease associated with valve insufficiency or valve failure of a native valve, the method comprising implanting the implant of claim 1, the implant being a prosthetic valve, the prosthetic valve being implanted at or adjacent to a location associated with the native valve.

*     *     *     *     *